United States Patent
Edmunds et al.

(12) 
(10) Patent No.: US 6,838,564 B2
(45) Date of Patent: Jan. 4, 2005

(54) SUBSTITUTED PYRIDINE HERBICIDES

(75) Inventors: Andrew Edmunds, Basel (CH); Alain De Mesmaeker, Kaenerkinden (CH); Christoph Lüthy, Münchenstein (CH); Jürgen Schaetzer, Rheinfelden (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 76 days.

(21) Appl. No.: 10/297,685

(22) PCT Filed: Jun. 7, 2001

(86) PCT No.: PCT/EP01/06430

§ 371 (c)(1),
(2), (4) Date: Dec. 6, 2002

(87) PCT Pub. No.: WO01/94339

PCT Pub. Date: Dec. 13, 2001

(65) Prior Publication Data

US 2004/0097729 A1 May 20, 2004

(30) Foreign Application Priority Data

Jun. 9, 2000 (CH) .............................................. 115100

(51) Int. Cl.$^7$ ............................................. C07D 213/02

(52) U.S. Cl. .................... 546/340; 546/276.4; 546/193; 544/124; 544/60

(58) Field of Search ................................ 546/340, 193, 546/276.4; 504/130; 544/60, 124

(56) References Cited

U.S. PATENT DOCUMENTS 5,260,262 A   11/1993   Lee et al. ................... 504/562

FOREIGN PATENT DOCUMENTS

| WO | 00/15615 | 3/2000 |
| WO | 00/39094 | 7/2000 |

*Primary Examiner*—Zinna Northington Davis
(74) *Attorney, Agent, or Firm*—Thomas Hamilton

(57) ABSTRACT

Compounds of the formula (I) in which the substituents are as defined in claim 1 are suitable for use as herbicides (I)

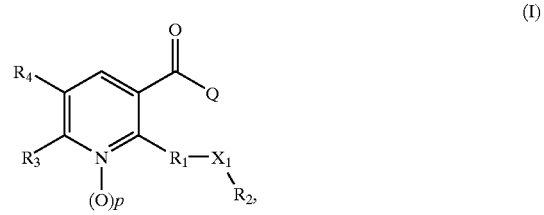

5 Claims, No Drawings

SUBSTITUTED PYRIDINE HERBICIDES

This application is a 371 of International Application No. PCT/EP01/06430, filed Jun. 7, 2001, the contents of which are incorporated herein by reference.

The present invention relates to novel herbicidally active pyridine ketones, to processes for their preparation, to compositions which comprise these compounds, and to their use for controlling weeds, in particular in crops of useful plants, or for inhibiting plant growth.

Pyridine ketones having herbicidal action are described, for example, in WO 00/15615 and WO/0039094.

We have now found novel pyridine ketones having herbicidal and growth-inhibiting properties.

The present invention thus provides compounds of the formula I

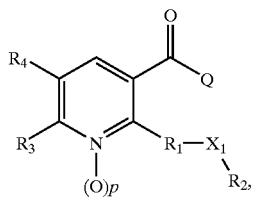

(I)

in which p is 0 or 1;

$R_1$ is a $C_1$–$C_6$alkylene, $C_3$–$C_6$alkenylene or $C_3$–$C_6$alkynylene chain which may be mono- or polysubstituted by halogen or $R_5$, where the unsaturated bonds of the chain are not attached directly to the substituent $X_1$;

$X_1$ is oxygen, —O(CO)—, —(CO)O—, —O(CO)O—, —N($R_6$)—O—, —O—N$R_{51}$—, thio, sulfinyl, sulfonyl, —SO$_2$N$R_7$—, —N$R_{52}$SO$_2$— or —N$R_8$;

$R_2$ is a $C_1$–$C_8$alkyl, $C_3$–$C_6$alkenyl or $C_3$–$C_6$alkyny group which is mono- or polysubstituted by halogen, hydroxyl, amino, formyl, nitro, cyano, mercapto, carbamoyl, $C_1$–$C_6$alkoxy, $C_1$–$C_6$alkoxycarbonyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, by halogen-substiuted $C_3$–$C_6$cycloalkyl, or by $C_3$–$C_6$alkenyloxy, $C_3$–$C_6$alkynyloxy, $C_1$–$C_6$haloalkoxy, $C_3$–$C_6$haloalkenyloxy, cyano-$C_1$–$C_6$alkoxy, $C_1$–$C_6$alkoxy-$C_1$–$C_6$alkoxy, $C_1$–$C_6$alkoxy-$C_1$–$C_6$alkoxy-$C_1$–$C_6$alkoxy, $C_1$–$C_6$alkylthio-$C_1$–$C_6$alkoxy, $C_1$–$C_6$alkyl-sulfinyl-$C_1$–$C_6$alkoxy, $C_1$–$C_6$alkylsulfonyl-$C_1$–$C_6$alkoxy, $C_1$–$C_6$alkoxycarbonyl-$C_1$–$C_6$alkoxy, $C_1$–$C_6$alkoxycarbonyl, $C_1$–$C_6$alkylcarbonyl, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, oxiranyl, which for its part may be substituted by $C_1$–$C_6$alkyl, or by (3-oxetanyl)oxy, which for its part may be substituted by $C_1$–$C_6$alkyl, or by benzylthio, benzylsulfinyl, benzylsulfonyl, $C_1$–$C_6$alkylamino, di($C_1$–$C_6$alkyl)amino, $R_9$S(O)$_2$O, $R_{10}$N($R_{11}$)SO$_2$—, thiocyanato, phenyl, phenoxy, phenylthio, phenylsulfinyl or phenylsulfonyl;

where the phenyl- or benzyl-containing groups for their part may be substituted by one or more $C_1$–$C_6$alkyl, $C_1$–$C_6$haloalkyl, $C_1$–$C_6$alkoxy, $C_1$–$C_6$haloalkoxy, halogen, cyano, hydroxyl or nitro groups, or $R_2$ is phenyl which may be mono- or polysubstituted by $C_1$–$C_6$alkyl, $C_1$–$C_6$haloalkyl, $C_1$–$C_6$alkoxy, $C_1$–$C_6$haloalkoxy, halogen, cyano, hydroxyl or nitro; or $R_2$ is $C_3$–$C_6$cycloalkyl, $C_1$–$C_6$alkoxy- or $C_1$–$C_6$alkyl-substituted $C_3$–$C_6$cycloalkyl, 3-oxetanyl or $C_1$–$C_6$alkyl-substituted 3-oxetanyl;

or, if Q is $Q_2$ or $Q_3$, or is $Q_1$ in which $R_{14}$ and $R_{22}$ are a $C_2$–$C_3$alkylene chain, $R_2$ is additionally also a five- to ten-membered monocyclic or fused bicyclic ring system which may be aromatic, saturated or partially saturated and may contain 1 to 4 heteroatoms selected from the group consisting of nitrogen, oxygen and sulfur, where the ring system is attached directly or via a $C_1$–$C_4$alkylene, $C_2$–$C_4$alkenyl-$C_1$–$C_4$alkylene, $C_2$–$C_4$alkynyl-$C_1$–$C_4$alkylene, —N($R_{12}$)—$C_1$–$C_4$alkylene, —SO—$C_1$–$C_4$alkylene or —SO$_2$—$C_1$–$C_4$alkylene group to the substituent $X_1$ and where each ring system may not contain more than two oxygen atoms and not more than two sulfur atoms and the ring system for its part may be mono-, di- or trisubstituted by $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_1$–$C_6$alkoxy, hydroxyl, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di($C_1$–$C_2$alkyl)aminosulfonyl, di($C_1$–$C_4$alkyl)amino, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where the substituents on the nitrogen in the heterocyclic ring are different from halogen; or $R_2$ is hydrogen or unsubstituted $C_1$–$C_8$alkyl if
a) $R_1$ is substituted by the group $R_5$, or
b) Q is the group $Q_2$, or
c) Q is the group $Q_3$ in which $X_1$ is —O(CO)—, —(CO)O—, —N($R_6$)—O—, —O—N$R_{51}$—, —SO$_2$N$R_7$—, —N$R_{52}$SO$_2$— or —N$R_8$—; or
d) Q is the group $Q_1$ in which $X_1$ is —N($R_6$)—O—, —O—N$R_{51}$—, —SO$_2$N$R_7$—, —N$R_{52}$SO$_2$— or —N$R_8$—, or
e) Q is the group $Q_1$ in which $R_{14}$ and $R_{22}$ in $Q_1$ are a $C_2$–$C_3$alkylene chain and $X_1$ is —O(CO)— or —(CO)O—, $R_3$ is $C_1$–$C_3$haloalkyl;

$R_4$ is hydrogen, halogen, $C_1$–$C_3$alkyl, $C_1$–$C_3$haloalkyl, $C_1$–$C_3$alkoxy, $C_1$–$C_3$alkoxy-$C_1$–$C_3$alkyl or $C_1$–$C_3$alkoxy-$C_1$–$C_3$alkoxy;

$R_5$ is hydroxyl, $C_1$–$C_6$alkoxy, $C_3$–$C_6$cycloalkyloxy, $C_1$–$C_6$alkoxy-$C_1$–$C_6$alkoxy, $C_1$–$C_6$alkoxy-$C_1$–$C_6$alkoxy-$C_1$–$C_6$alkoxy or $C_1$–$C_2$alkylsulfonyloxy;

$R_6$, $R_7$, $R_8$, $R_9$, $R_{10}$, $R_{11}$, $R_{12}$, $R_{51}$ and $R_{52}$ independently of one another are hydrogen, $C_1$–$C_6$alkyl, $C_1$–$C_6$haloalkyl, $C_1$–$C_6$alkoxycarbonyl, $C_1$–$C_6$alkylcarbonyl, $C_1$–$C_6$alkoxy-$C_1$–$C_6$alkyl, $C_1$–$C_6$-alkoxy-$C_1$–$C_6$alkyl substituted by $C_1$–$C_6$alkoxy, benzyl or phenyl, where phenyl and benzyl for their part may be mono- or polysubstituted by $C_1$–$C_6$alkyl, $C_1$–$C_6$haloalkyl, $C_1$–$C_6$alkoxy, $C_1$–$C_6$haloalkoxy, halogen, cyano, hydroxyl or nitro;

where $R_6$ and $R_9$ are not simultaneously hydrogen and hydrogen, $C_1$–$C_6$alkoxycarbonyl or $C_1$–$C_6$alkylcarbonyl, respectively;

Q is $Q_1$

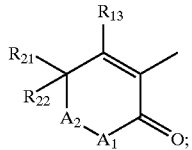

(Q₁)

in which $A_1$ is $C(R_{14}R_{15})$, $NR_{16}$ or oxygen;

$A_2$ is $C(R_{17}R_{18})$, $C(O)$, —C=N—O—$R_{19}$, oxygen, thio, sulfinyl, sulfonyl, —$NR_{20}$ or ethylene; with the provisos that $A_1$ is different from oxygen if $A_2$ is oxygen, $C(O)$, thio, sulfinyl, —C=N—O—$R_{19}$, $NR_{20}$ or $C(R_{17}R_{18})$, where $R_{17}$ and $R_{18}$ independently of one another are $C_1$–$C_4$alkoxy, $C_1$–$C_4$alkylthio, $C_1$–$C_4$alkylsulfinyl, $C_1$–$C_4$alkylsulfonyl; and $A_1$ is different from $NR_{16}$ if $A_2$ is thio, sulfinyl or $C(R_{17}R_{18})$, where $R_{17}$ and $R_{18}$ independently of one another are $C_1$–$C_4$alkoxy, $C_1$–$C_4$alkylthio, $C_1$–$C_4$alkylsulfinyl, $C_1$–$C_4$alkylsulfonyl; $R_{14}$ and $R_{22}$ independently of one another are hydrogen, $C_1$–$C_4$alkyl, $C_1$–$C_4$haloalkyl, $C_3$–$C_4$alkenyl, $C_3$–$C_4$alkynyl, $C_1$–$C_4$alkylthio, $C_1$–$C_4$alkylsulfinyl, $C_1$–$C_4$alkylsulfonyl, $C_1$–$C_4$alkylsulfonyloxy, $C_1$–$C_4$alkoxy, $C_1$–$C_4$alkoxycarbonyl or $C_1$–$C_4$alkylcarbonyl;

$R_{15}$ and $R_{21}$ independently of one another are hydrogen, $C_1$–$C_4$alkyl, $C_1$–$C_4$haloalkyl, $C_3$–$C_4$alkenyl or $C_3$–$C_4$alkynyl;

$R_{17}$ is hydrogen, $C_1$–$C_4$alkyl, $C_1$–$C_4$haloalkyl, $C_1$–$C_4$alkoxy, $C_1$–$C_4$alkylthio, $C_1$–$C_4$alkylsulfinyl or $C_1$–$C_4$alkylsulfonyl;

$R_{18}$ is hydrogen, $C_1$–$C_4$alkyl, $C_1$–$C_4$haloalkyl, ₃–$C_4$alkenyl, $C_3$–$C_4$alkynyl, $C_1$–$C_4$alkoxy, $C_1$–$C_4$alkylthio, $C_1$–$C_4$alkylsulfinyl, $C_1$–$C_4$alkylsulfonyl or $C_1$–$C_4$dialkoxyalkyl-$C_1$–$C_4$alkyl;

$R_{20}$ is $C_1$–$C_4$alkyl, $C_3$–$C_6$cycloalkyl, $C_3$–$C_4$alkenyl, $C_3$–$C_4$alkynyl, $C_1$–$C_4$alkylcarbonyl, $C_1$–$C_4$alkylcarbonyloxy, di($C_1$–$C_4$alkyl)aminocarbonyl or benzyl, where the phenyt group may be mono- or polysubstduted by $C_1$–$C_6$alkyl, $C_1$–$C_6$haloalkyl, $C_1$–$C_6$alkoxy, $C_1$–$C_6$haloalkoxy, halogen, cyano, hydroxyl or nitro;

$R_{19}$ and $R_{16}$ independently of one another are hydrogen, $C_1$–$C_4$alkyl, $C_3$–$C_6$cycloalkyl, $C_3$–$C_4$alkenyl, $C_3$–$C_4$alkynyl, benzyl or phenyl, where phenyl and benzyl for their part may be mono- or polysubstituted by $C_1$–$C_6$alkyl, $C_1$–$C_6$haloalkyl, $C_1$–$C_6$alkoxy, $C_1$–$C_6$haloalkoxy, halogen, cyano, hydroxyl or nitro;

or $R_{14}$ and $R_{22}$ together form a $C_2$–$C_3$alkylene chain;

or $R_{14}$ and $R_{15}$ together and/or $R_{17}$ and $R_{18}$ together and/or $R_{21}$ and $R_{22}$ together form a $C_2$–$C_4$alkylene chain which mayebe interrupted by oxygen and/or carbonyl and/or sulfur, with the proviso that the oxygen and sulfur atoms are separated by at least one methylene group;

or $R_{14}$ and $R_{18}$ together form a $C_2$–$C_4$alkylene chain; or $R_{22}$ and $R_{18}$ together form a $C_2$–$C_4$alkylene chain;

or $R_{18}$ together with $R_{22}$ or $R_{14}$ forms a direct bond;

or $R_{16}$ and $R_{18}$ together form a $C_2$–$C_4$alkylene chain;

$R_{13}$ is hydroxyl, $O^-M^+$, where $M^+$ is an alkali metal cation or ammonium cation, halogen, $C_1$–$C_{12}$alkylsulfonyloxy, amino, $C_1$–$C_4$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_3$–$C_{12}$alkenylthio, $C_3$–$C_{12}$alkenylsulfinyl, $C_3$–$C_{12}$alkenylsulfonyl, $C_3$–$C_{12}$alkynylthio, $C_3$–$C_{12}$alkynylsulfinyl, $C_3$–$C_{12}$alkynylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, $(C_1$–$C_4$alkoxy$)_2$P(O)O, $C_1$–$C_4$alkyl-$(C_1$–$C_4$alkoxy)P(O)O, H$(C_1$–$C_4$alkoxy)P(O)O, $R_{23}R_{24}$N, $R_{25}R_{26}$NNH, $R_{27}R_{28}$NC(O)O—, $R_{29}R_{30}$NC(O)NH—, $C_1$–$C_{18}$alkylcarbonyloxy, $C_2$–$C_{18}$alkenylcarbonyloxy, $C_2$–$C_{18}$alkynylcarbonyloxy, $C_3$–$C_6$cycloalkylcarbonyloxy, $C_1$–$C_{12}$alkoxycarbonyloxy, $C_1$–$C_{12}$alkylthiocarbonyloxy, $C_1$–$C_{12}$alkylthiocarbamoyl, where the alkyl, alkenyl and alkynyl groups may be substituted by halogen, $C_1$–$C_6$alkoxy, $C_1$–$C_6$alkylthio, $C_1$–$C_6$alkylsulfinyl, $C_1$–$C_6$alkylsulfonyl or cyano;

or $R_{13}$ is phenoxy, phenylthio, phenylsulfinyl, phenylsulfonyl, phenylsulfonylamino, phenylsulfonyloxy or benzoyloxy, where the phenyl groups for their part may be substituted by one or more halogen, nitro, cyano, $C_1$–$C_4$alkyl, $C_1$–$C_4$haloalkyl, $C_1$–$C_4$alkoxy or $C_1$–$C_4$haloalkoxy groups;

or $R_{13}$ is a group $Het_1$-thio, $Het_2$-sulfinyl, $Het_3$-sulfonyl, $Het_4$—(CO)O or $Het_5$-N($R_{33}$); in which $Het_1$, $Het_2$, $Het_3$, Het4 and $Het_5$ independently of one another are a five- to ten-membered monocyclic or fused bicyclic ring system which may be aromatic or partially saturated and may contain 1 to 4 heteroatoms selected from the group consisting of nitrogen, oxygen and sulfur, and where each ring system may not contain more than 2 oxygen atoms and not more than 2 sulfur atoms, and where the ring system itself can be substituted by $C_1$–$C_6$alkyl, $C_1$–$C_6$haloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, di($C_1$–$C_4$alkyl)aminosulfonyl, di($C_1$–$C_4$alkyl)amino, halogen, cyano, nitro or phenyl, and where the substituents on the nitrogen in the heterocyclic ring are different from halogen;

$R_{23}$, $R_{24}$, $R_{25}$, $R_{26}$, $R_{27}$, $R_{28}$, $R_{29}$, $R_{30}$ and $R_{33}$ independently of one another are hydrogen $C_1$–$C_6$alkyl;

or $R_{23}$ and $R_{24}$ together or $R_{25}$ and $R_{26}$ together or $R_{27}$ and $R_{28}$ together or $R_{29}$ and $R_{30}$ together are pyrolidino, piperidino, morpholino, thiomorpholino, which may be mono- or polysubstituted by methyl groups; or Q is $Q_2$

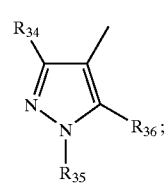

(Q₂)

in which $R_{34}$ is hydrogen, $C_1$–$C_4$alkyl, $C_1$–$C_4$haloalkyl, $C_3$–$C_6$cycloalkyl, $C_2$–$C_4$alkenyl, $C_2$–$C_4$alkynyl or benzyl, where the phenyl group may be mono- or polysubstituted by $C_1$–$C_6$alkyl, $C_1$–$C_6$haloalky, $C_1$–$C_6$alkoxy, $C_1$–$C_6$haloalkoxy, halogen, cyano, hydroxyl or nitro; $R_{35}$ is hydrogen, $C_1$–$C_4$alkyl, $C_1$–$C_4$haloalkyl, $C_3$–$C_8$cycloalkyl, $C_3$–$C_4$alkenyl, $C_3$–$C_4$alkynyl or benzyl, where the phenyl group may be mono- or polysubstituted by $C_1$–$C_6$alkyl, $C_1$–$C_6$haloalkyl, $C_1$–$C_6$alkoxy, $C_1$–$C_6$haloalkoxy, halogen, cyano, hydroxyl or nitro;

$R_{36}$ is hydroxyl, $O^-M^+$, where $M^+$ is an alkali metal cation or ammonium cation, halogen, $C_1$–$C_{12}$alkylsulfonyloxy, amino, $C_1$–$C_4$alkylthio, $C_1$–$C_{12}$alkylsulfinyl, $C_1$–$C_2$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_3$–$C_{12}$alkenylthio, $C_3$–$C_{12}$alkenylsulfinyl, $C_3$–$C_{12}$alkenylsulfonyl, $C_3$–$C_{12}$alkynylthio, $C_3$–$C_{12}$alkynylsulfinyl, $C_3$–$C_{12}$alkynylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, $(C_1$–$C_4$alkoxy$)_2$P(O)O, $C_1$–$C_4$alkyl-$(C_1$–$C_4$alkoxy)P(O)O, H$(C_1$–$C_4$alkoxy)P(O)O, $R_{37}R_{38}$N, $R_{39}R_{40}$NNH, $R_{41}R_{42}$NC(O)O—, $R_{43}R_{44}$NC(O)NH—, $C_1$–$C_{18}$alkylcarbonyloxy, $C_2$–$C_{18}$alkenylcarbonyloxy, $C_2$–$C_{18}$alkynylcarbonyloxy, $C_3$–$C_6$cycloalkylcarbonyloxy, $C_1$–$C_{12}$alkoxycarbonyloxy, $C_1$–$C_{12}$alkylthiocarbonyloxy or $C_1$–$C_{12}$alkylthiocarbamoyl, where the alkyl, alkenyl and alkynyl groups may be substituted by halogen, $C_1$–$C_6$alkoxy, $C_1$–$C_6$alkylthio, $C_1$–$C_6$alkylsulfinyl, $C_1$–$C_6$alkylsulfonyl or cyano; or $R_{36}$ is phenoxy, phenylthio, phenylsulfinyl, phenylsulfonyl, phenylsulfonylamino, phenylsulfonyloxy or benzoyloxy, where the phenyl groups for their part may be mono- or polysubstituted by halogen, nitro, cyano, $C_1$–$C_4$alkyl, $C_1$–$C_4$haloalkyl, $C_1$–$C_4$alkoxy, $C_1$–$C_4$haloalkoxy, or $R_{36}$ is a group Het$_7$-thio, Het$_8$-sulfinyl, Het$_9$-sulfonyl, Het$_{10}$-(CO)O or Het$_{11}$-N(R$_{47}$); in which Het$_7$, Het$_8$, Het$_9$, Het$_{10}$ and Het$_{11}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and where each ring system may not contain more than 2 oxygen atoms and not more than 2 sulfur atoms, and where the ring system for its part may be substituted by $C_1$–$C_6$alkyl, $C_1$–$C_6$haloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, di($C_1$–$C_4$alkyl)aminosulfonyl, di($C_1$–$C_4$alkyl)amino, halogen, cyano, nitro or phenyl, and where the substituents on the nitrogen in the heterocyclic ring are different from halogen;

$R_{37}$, $R_{38}$, $R_{39}$, $R_{40}$, $R_{41}$, $R_{42}$, $R_{43}$, $R_{44}$ and $R_{47}$ independently of one another are hydrogen or $C_1$–$C_6$alkyl; or $R_{37}$ and $R_{38}$ together or $R_{39}$ and $R_{40}$ together or $R_4$, and $R_{42}$ together or $R_{43}$ and $R_{44}$ together are pyrolidino, piperidino, morpholino, thiomorpholino, which may be mono- or polysubstituted by methyl groups;

or Q is $Q_3$

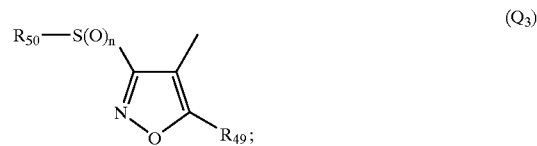

(Q$_3$)

in which $R_{49}$ is $C_1$–$C_4$alkyl, $C_1$–$C_4$haloalkyl, $C_3$–$C_6$cycloalkyl or halogen-substituted $C_3$–$C_6$cycloalkyl;

$R_{50}$ is $C_1$–$C_3$alkylene which may be substituted by halogen, hydroxyl, $C_1$–$C_6$alkoxy, $C_2$–$C_6$alkenyl, $C_2$–$C_6$alkynyl, $C_3$–$C_6$cycloalkyl, $C_1$–$C_6$alkoxy-$C_1$–$C_6$alkoxy, $C_1$–$C_6$alkoxy-$C_1$–$C_6$alkoxy-$C_1$–$C_6$alkoxy, (3oxetanyl)oxy, or by $C_1$–$C_6$alkyl-substituted (3-oxetanyl)oxy, or by benzylthio, benzylsulfinyl, benzylsulfonyl, phenyl, phenoxy, phenylthio, phenylsulfinyl or phenylsulfonyl, where the phenyl- and benzyl-containing groups for their part may be substituted by one or more $C_1$–$C_6$alkyl, $C_1$–$C_6$haloalkyl, $C_1$–$C_8$alkoxy, $C_1$–$C_6$haloalkoxy, halogen, cyano, hydroxyl or nitro groups;

or $R_{50}$ is phenyl, where the phenyl-containing group for its part may be substituted by one or more $C_1$–$C_6$alkyl, $C_1$–$C_6$haloalkyl, $C_1$–$C_6$alkoxy, $C_1$–$C_6$haloalkoxy, halogen, cyano, hydroxyl or nitro, or $R_{50}$ is $C_3$–$C_6$cycloalkyl, $C_1$–$C_6$alkoxy- or $C_1$–$C_6$alkyl-substituted $C_3$–$C_6$cycloalkyl, 3oxetanyl or $C_1$–$C_6$alkyl-substituted 3oxetanyl; and n is 0, 1 or 2; and agronomically acceptable salts/N-oxideslisomers/enantiomers of these compounds.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, heptyl, octyl, nonyl, decyl, undecyl and dodecyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine, preferably fluorine and chlorine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$–$C_{20}$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having a chain length of from 3 to 5 carbon atoms.

In the context of the present invention, the alkali metal cation $M^+$ (for example in the definition of $R_{13}$) is preferably the sodium cation or the potassium cation.

Alkoxy groups preferably have a chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 8 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 8 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsultinyl and ethylsulfinyl.

Alkylsufonyl is, for example, methylsulfonyl, ethylsulfonyl, propylsufonyl, isopropylsulfonyl, n-butylsulfonyl, isobutylsulfonyl, sec-butylsulfonyl or tert-butylsulfonyl; preferably methylsulfonyl or ethylsulfonyl. Alkoxyalkoxy groups preferably have a chain length of from 1 to 8 carbon atoms. Examples of alkoxyalkoxy groups are: methoxymethoxy, methoxyethoxy, methoxypmpoxy, ethoxymethoxy, ethoxyethoxy, propoxymethoxy or butoxybutoxy. Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms. Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. The cycloalkyl groups preferably have from 3 to 8 ring carbon atoms, for example cyclopropyl, cyclobutyl, cyclopentyl, cyclohexyl, cycloheptyl and cyclooctyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

The compounds of the formula I may occur in different tautomeric forms, for example, it $R_{13}$ is hydroxyl, in the preferred formulae I'and I''''

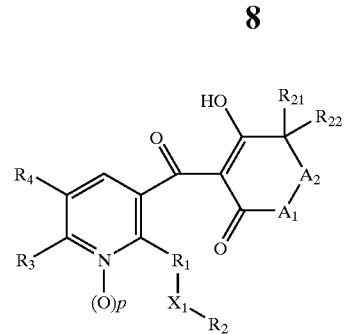

The invention also embraces the salts which can be formed by compounds of the formula I, preferably with amines, alkali metal and alkaline earth metal bases or quarternary ammonium bases. Suitable salt formers are described, for example, in WO 98141089.

The invention also embraces the salts which can be formed by the compounds of the formula I with amines, alkali metal and alkaline earth metal bases or quarternary ammonium bases. Among the alkali metal and alkaline earth metal hydroxides, the hydroxides of lithium, sodium, potassium, magnesium or calcium, in particular those of sodium or potassium, may be emphasized as salt formers.

Examples of amines suitable for ammonium salt formation are both ammonia and primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o,m,p-toluidines, phenylenediamines, benzidines, naphthylamines and o,m,p-chloroanilines; but in particular triethylamine, isopropylamine and diisopropylamine.

Preferred quarternary ammonium bases which are suitable for salt formation correspond, for example, to the formula $[N(R_aR_bR_cR_d)]OH$, in which $R_a$, $R_b$, $R_c$ and $R_d$ independently of one another are $C_1$–$C_4$alkyl. Other suitable tetraalkylammonium bases with other anions can be obtained, for example, by anion exchange reactions.

Compounds of formula I, wherein p is 0, are preferred.

Preferred compounds of the formula I are those in which $R_1$ is —$CH_2$—, —$CH_2CH_2$—, —$CF_2$, —CH=$CHCH_2$—, —CH($CH_3$)— or —C≡$CCH_2$—, but particularly preferably —$CH_2$— where in each case the free valences on the left are attached to the pyridine ring.

Preference is furthermore given to those compounds of the formula I, in which $X_1$ is oxygen, sulfonyl or a group —$NR_{52}SO_2$—, in particular oxygen.

Of particular interest are compounds of the formula I, in which $R_2$ is —$CH_2OCH_3$, —$CH_2OCH_2CH_3$, —$CH_2CH_2OCH_3$, —$CH_2CH_2SO_2CH_3$ or —$CH_2CH_2OCH_2CH_2OCH_3$, preferably —$CH_2CH_2OCH_3$, those compounds standing out in which $X_1$ is oxygen and $R_1$ is —$CH_2$—.

Among this group, preference is given to those compounds in which Q is $Q_1$ and $R_{13}$ is hydroxyl.

Emphasis is furthermore given to the compounds of the formula I in which $R_2$

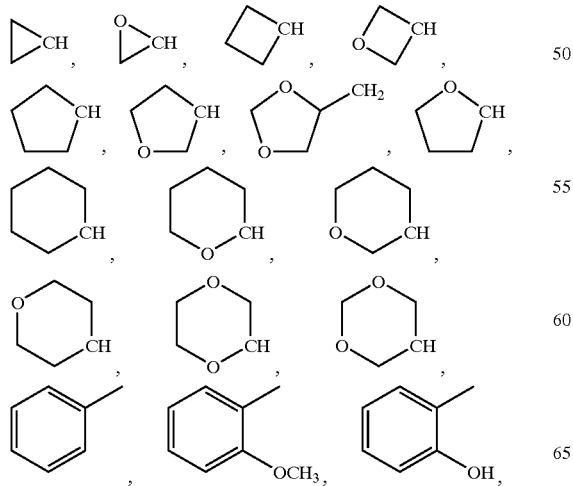

-continued

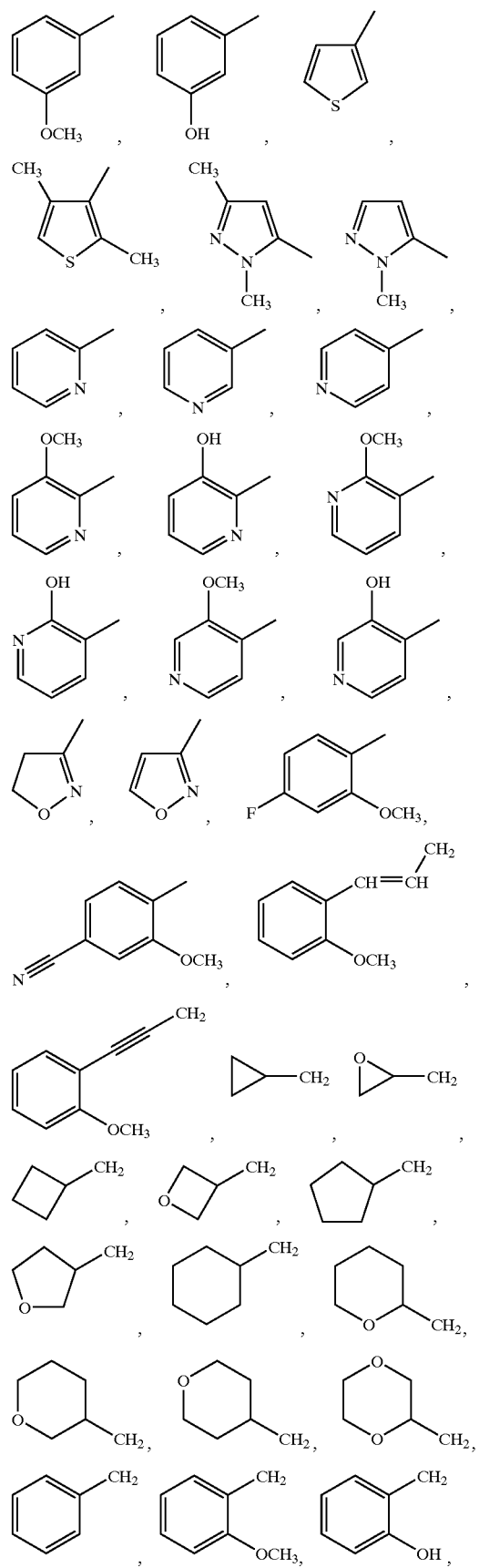

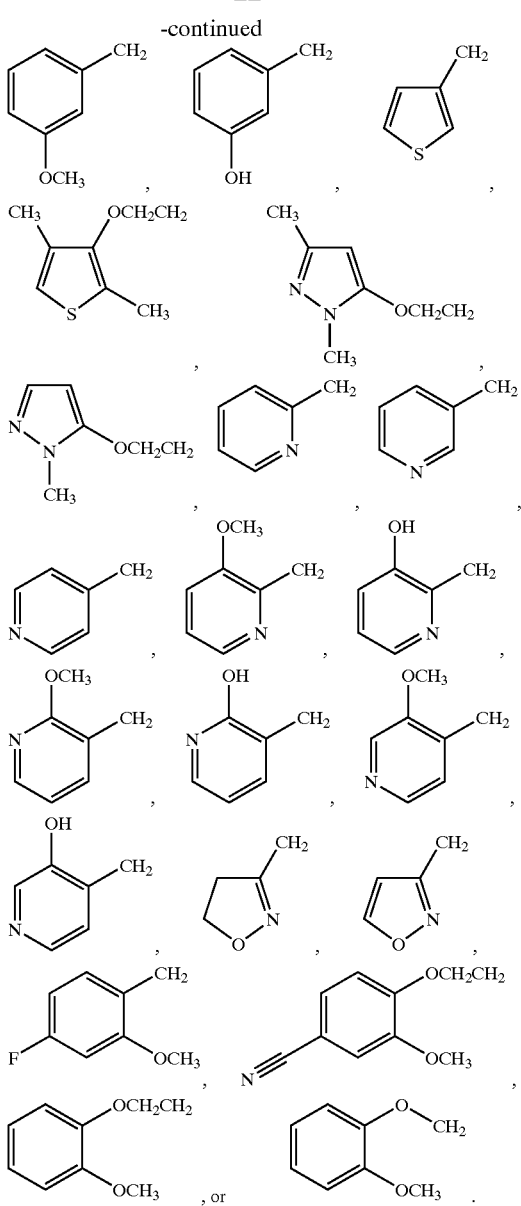

if, in these preferred meanings of $R_2$, no free valency is indicated, as, for example, in the case of

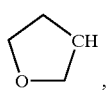

the point of attachment is the carbon atom indicated by "CH".

In a further preferred group of compounds of the formula I, $R_3$ is $CF_3$, $CF_2CF_3$, $CF_2Cl$, $CF_2H$ or $CCl_3$, particularly preferably $CF_3$, where $R_4$ is preferably hydrogen or methyl, particularly preferably hydrogen.

$R_6$, $R_7$, $R_8$, $R_9$, $R_{10}$, $R_{11}$, $R_{12}$, $R_{51}$ and $R_{52}$ independently of one another are in particular hydrogen, $C_1$–$C_4$alkyl, $C_2$–$C_6$alkoxy-$C_1$–$C_6$alkyl or $C_1$–$C_6$alkoxy-$C_1$–$C_6$alkyl which is substituted by $C_1$–$C_6$alkoxy, where in a preferred group of compounds of the formula I additionally Q is $Q_2$ and $R_1$ is methylene.

Very particularly preferably, Q is $Q_1$ and $R_{13}$ is hydroxyl or halogen, in particular hydroxyl. Among this group, emphasis is given to those compounds in which a) $A_1$ is $C(R_{14}R_{15})$ or $NR_{16}$ and $A_2$ is $C(R_{17}R_{18})$, $C(O)$ or oxygen, or b) $A_1$ is $C(R_{14}R_{15})$ and $A_2$ is $C(R_{17}R_{18})$ and $R_{14}$ and $R_{22}$ together form a $C_2$–$C_3$alkylene chain, preferably an ethylene chain, where $R_{15}$, $R_{17}$, $R_{18}$ and $R_{21}$ are particularly preferably hydrogen; or c) $A_2$ is $C(O)$ or $C(R_{17}R_{18})$, $A_1$ is $C(R_4R_{15})$ and $R_{14}$, $R_{15}$, $R_{17}$ and $R_{18}$ independently of one another are hydrogen, methyl, ethyl, methoxycarbonyl or ethoxycarbonyl; or d) $R_{14}$ and $R_{15}$ or $R_2$, and $R_{22}$ together form a $C_2$alkylene chain (cyclopropyl ring), $A_2$ is $CH_2$ and $R_{21}$ and $R_{22}$ or $R_{14}$ and $R_{15}$ independently of one another are hydrogen, $C_1$–$C_4$alkyl, methoxycarbonyl or ethoxycarbonyl; or e) $A_2$ is $C(R_{17}R_{18})$ and $A_1$ is $C(R_{14}R_{15})$ and $R_{18}$ and $R_{14}$ together form a $C_2$–$C_3$alkylene chain.

In a further outstanding group of compounds of the formula I, Q is $Q_3$, $R_{49}$ is cyclopropyl and $R_{50}$—$S(O)_n$ is methylthio, ethylthio, methylsulfinyl, ethylsulfinyl, methylsulfonyl or ethylsulfonyl.

The compounds of the formula I can be prepared by processes known per se, for example those described in WO 97/46530 or WO 00/15615 or WO/0039094, for example in the case of compounds of the formula I,

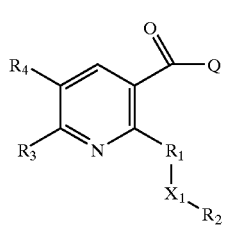

(I)

in which $R_1$, $R_2$, $R_3$, $R_4$ and $X_1$ are as defined under formula I and Q is a group (I),

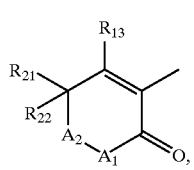

(Q₁)

by, for example, either a) reacting a compound of the formula Ia

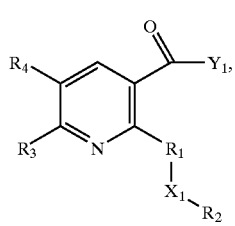

(Ia)

in which $R_1$, $R_2$, $R_3$, $R_4$ and $X_1$ are as defined under formula I and $Y_1$ is a leaving group, for example halogen or cyano, in an inert organic solvent in the presence of a base with a compound of the formula II

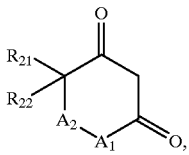

in which $R_{22}$, $R_{21}$, $A_2$ and $A_1$ are as defined under formula I, to give the compounds of the formulae IIIa and IIIb

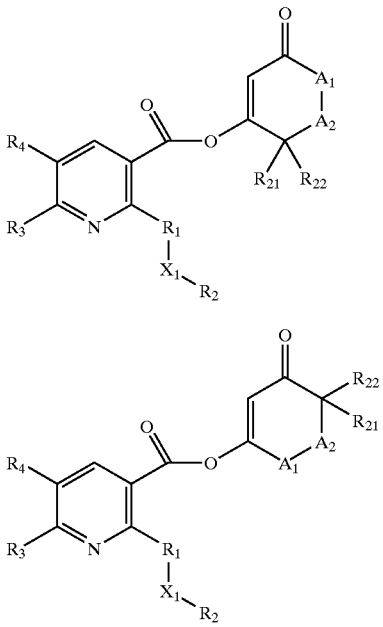

and then isomerizing these for example in the presence of a base and a catalytic amount of dimethylaminopyridine (DMAP) or a source of cyanide, for example acetone cyanohydrin; or b) reacting a compound of the formula Ib

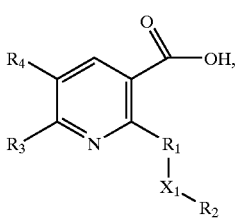

in which $R_1$, $R_2$, $R_3$, $R_4$ and $X_1$ are as defined under formula I, with a compound of the formula II

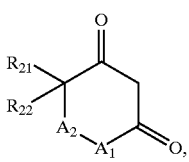

in which $R_{22}$, $R_{21}$, $A_1$ and $A_2$ are as defined under formula I, in an inert organic solvent in the presence of a base and a coupling agent to give the compounds of the formula IIIa or IIIb

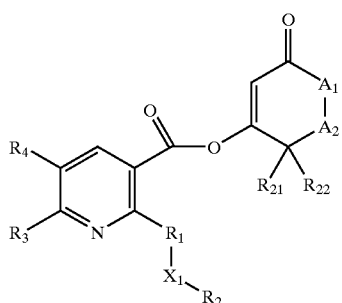

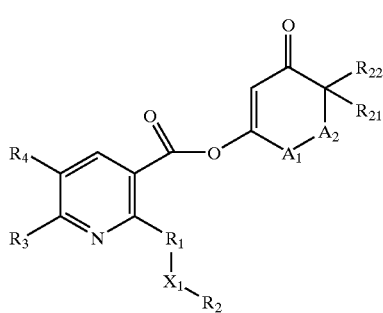

and then isomerizing these, for example as described under route a).

Compounds of the formula I, in which Q is a group

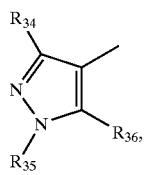

are prepared similarly to a known process (for example WO 97/46530), wherein either a) a compound of the formula Ia

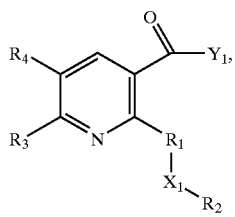

in which $R_1$, $R_2$, $R_3$, $R_4$ and $X_1$ are as defined under formula I and $Y_1$ is a leaving group, for example halogen or cyano, is reacted with a compound of the formula IIa

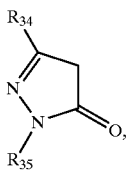
(IIa)

in which $R_{34}$ and $R_{35}$ are as defined, in an inert organic solvent in the presence of a base to give the compound of the formula IIIc

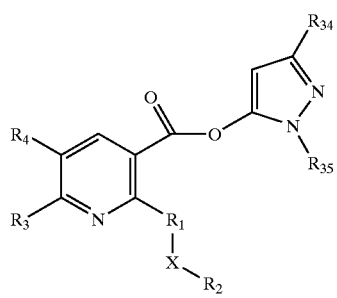
IIIc in which $R_1$, $R_2$, $R_3$, $R_4$, $R_{34}$, $R_{35}$ and $X_1$ are as defined under formula I, and this compound is then isomerized, for example in the presence of a base and a catalytic amount of a source of cyanide; or b) a compound of the formula Ib

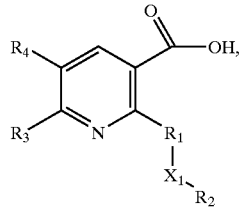
(Ib)

in which $R_1$, $R_2$, $R_3$, $R_4$ and $X_1$ are as defined under formula I, is reacted with a compound of the formula IIa

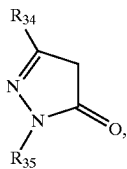
(IIa)

in which $R_{34}$ and $R_{35}$ are as defined above, in an inert organic solvent in the presence of a base and a coupling agent to give the compound of the formula IIIc

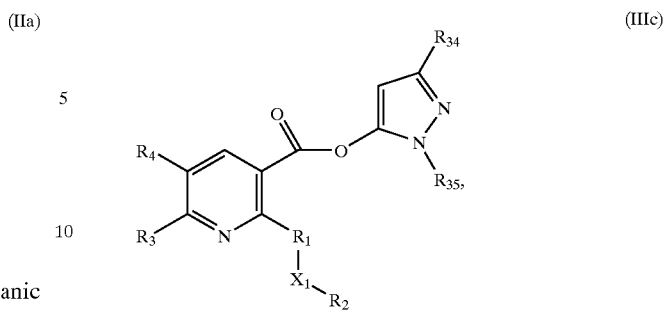
(IIIc)

and this compound is then isomerized as described under route a).

The compounds of the formula I, in which Q is a group

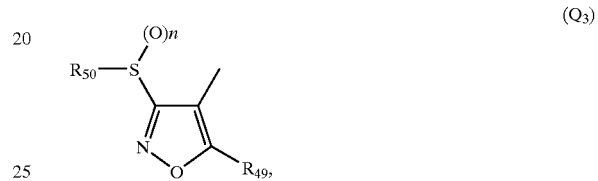
(Q3)

In which n is 0 and $R_{50}$ and $R_{49}$ are as defined above, are prepared similarly to known processes (for example those described in WO 00/1 5615, WO/0039094 or WO 97/43270), wherein either a) a compound of the formula IV

(IV)

in which $X_1$, $R_1$, $R_2$, $R_3$, $R_4$ and $R_{49}$ are as defined above, is converted in the presence of a base, carbon disulfide and an alkylating agent of the formula V $$R_{50}-Y_2 \quad (V),$$

in which $R_{50}$ is as defined under formula I, and $Y_2$ is a leaving group, for example halogen or sulfonate, into the compound of the formula VI

(VI)

in which $R_1$, $R_2$, $R_3$, $R_4$, $R_{50}$, $X_1$ and $R_{49}$ are as defined above, and this compound is then cyclized with hydroxylamine hydrochloride, if appropriate in a solvent, in the presence of a base, for example sodium acetate, to give the isomeric compounds of the formulae Ic and Id

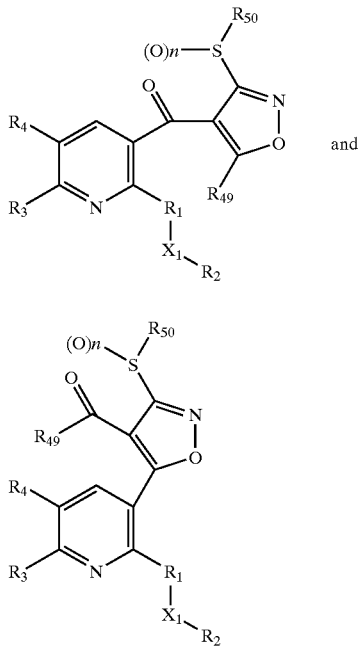

and these compounds are then oxidized with an oxidizing agent, for example with peracids, for example meta-chloroperbenzoic acid (m-CPBA) or peracetic acid, to give the corresponding sufloxides (n=1) and sulfones (n=2) of the formulae Ie and If, respectively. Isomers of the formulae Ic and Id (in which n=0) or Ie and If (in which n=1 or 2) can be separated and purified by column chromatography, using a suitable mobile phase.

The intermediates of the formulae Ia, Ib, IV and VI are novel and were developed specifically for the preparation of the compounds of the formula I. Accordingly, they also form part of the subject-matter of the present invention. Together, the novel intermediates of the formulae Ia, Ib, IV and VI correspond to formula XX

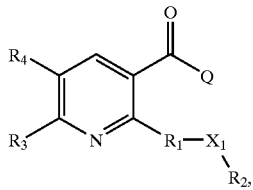

in which

Q is hydroxyl, halogen, cyano or $C_1$–$C_6$alkoxy, or is a group of the formula

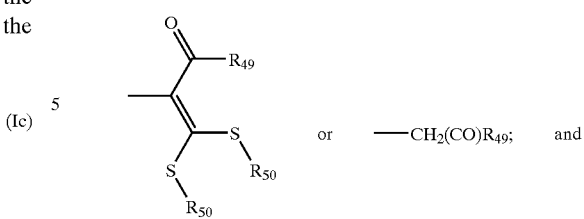

$R_1$, $R_3$, $R_4$, $R_{49}$, $R_{50}$, $X_1$ and p are as defined under formula I and $R_2$ is a $C_1$–$C_6$alkyl, $C_3$–$C_6$alkenyl or $C_3$–$C_6$alkynyl group which is mono- or polysubstituted by halogen, hydroxyl, amino, formyl, nitro, cyano, mercapto, carbamoyl, $C_1$–$C_6$alkoxy, $C_1$–$C_6$alkoxycarbonyl, $C_2$–$C_6$alkenyl, $C_2$–$C_6$haloalkenyl, $C_2$–$C_6$alkynyl, $C_2$–$C_6$haloalkynyl, $C_3$–$C_6$cycloalkyl, by halogen-substituted $C_3$–$C_6$cycloalkyl, or by $C_3$–$C_6$alkenyloxy, $C_3$–$C_6$alkynyloxy, $C_1$–$C_6$haloalkoxy, $C_3C_6$haloalkenyloxy, cyano-$C_1$–$C_6$alkoxy, $C_1$–$C_6$alkoxy-$C_1$–$C_6$alkoxy, $C_1$–$C_6$alkoxy-$C_1$–$C_6$alkoxy-$C_1$–$C_6$alkoxy, $C_1$–$C_6$alkylthio-$C_1$–$C_6$alkoxy, $C_1$–$C_6$alkylsulfinyl-$C_1$–$C_6$alkoxy, $C_1$–$C_6$alkylsulfonyl-$C_1$–$C_6$alkoxy, $C_1$–$C_6$alkoxycarbonyl-$C_1$–$C_6$alkoxy, $C_1$–$C_6$alkoxycarbonyl, $C_1$–$C_6$alkylcarbonyl, $C_1$–$C_6$alkylthio, $C_1$–$C_6$alkylsulfinyl, $C_1$–$C_6$alkylsulfonyl, $C_1$–$C_6$haloalkylthio, $C_1$–$C_8$haloalkylsulfinyl, $C_1$–$C_6$haloalkylsulfonyl, oxiranyl, which for its part may be substituted by $C_1$–$C_8$alkyl, or by (3-oxetanyl)oxy, which for its part may be substituted by $C_1$–$C_6$alkyl, or by benzylthio, benzylsulfinyl, benzylsulfonyl, $C_1$–$C_6$alkylamino, di($C_1$–$C_6$alkyl)amino, $R_9S(O)_2O$, $R_{10}N(R_{11})SO_2$—, thiocyanato, phenyl, phenoxy, phenylthio, phenylsulfinyl or phenylsulfonyl; where the phenyl- or benzyl-containing groups for their part may be substituted by one or more $C_1$–$C_6$alkyl, $C_1$–$C_6$haloalkyl, $C_1$–$C_6$alkoxy, $C_1$–$C_6$haloalkoxy, halogen, cyano, hydroxyl or nitro groups, or $R_2$ is phenyl which may be mono- or polysubstituted by $C_1$–$C_6$alkyl, $C_1$–$C_6$haloalkyl, $C_1$–$C_6$alkoxy, $C_1$–$C_6$haloalkoxy, halogen, cyano, hydroxyl or nitro; or $R_2$ is $C_3$–$C_6$cycloalkyl, $C_1$–$C_6$alkoxy- or $C_1$–$C_6$alkyl-substituted $C_3$–$C_6$cycloalkyl, 3oxetanyl or $C_1$–$C_6$alkyl-substituted 3oxetanyl;

or if $X_1$ is —N($R_6$)—O—, —O—$NR_{51}$, $SO_2NR_7$— or —$NR_{52}SO_2$— and $R_6$, $R_7$, $R_{51}$ and $R_{52}$ are as defined under formula I, $R_2$ may additionally be hydrogen, unsubstituted $C_1$–$C_6$alkyl, or a five- to ten-membered monocyclic or fused bicyclic ring system which may be aromatic, saturated or partially saturated and may contain 1 to 4 heteroatoms selected from the group consisting of nitrogen, oxygen and sulfur, where the ring system is attached directly or via a $C_1$–$C_4$alkylene, $C_2$–$C_4$alkenyl-$C_1$–$C_4$alkylene, $C_2$–$C_4$alkynyl-$C_1$–$C_4$alkylene, —N($R_{12}$)-$C_1$–$C_4$alkylene, —SO—$C_1$–$C_4$alkylene or —$SO_2$—$C_1$–$C_4$alkylene group to the substituent $X_1$, and where each ring system may not contain more than 2 oxygen atoms and not more than two sulfur atoms, and where the ring system for its part may be mono-, di- or trisubstituted by $C_1$–$C_6$alkyl, $C_1$–$C_6$haloalkyl, $C_2$–$C_6$alkenyl, $C_2$–$C_6$haloalkenyl, $C_2$–$C_6$alkynyl, $C_2$–$C_6$haloalkynyl, $C_1$–$C_6$alkoxy, hydroxyl, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$-haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, di($C_1$–$C_2$alkyl)aminosulfonyl, di($C_1$–$_4$alkyl)amino, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where the substituents on the nitrogen in the heterocyclic ring are different from halogen.

The preparation of the compounds of the formula I is illustrated in more detail in reaction schemes 1 and 2 below.

Reaction scheme 1

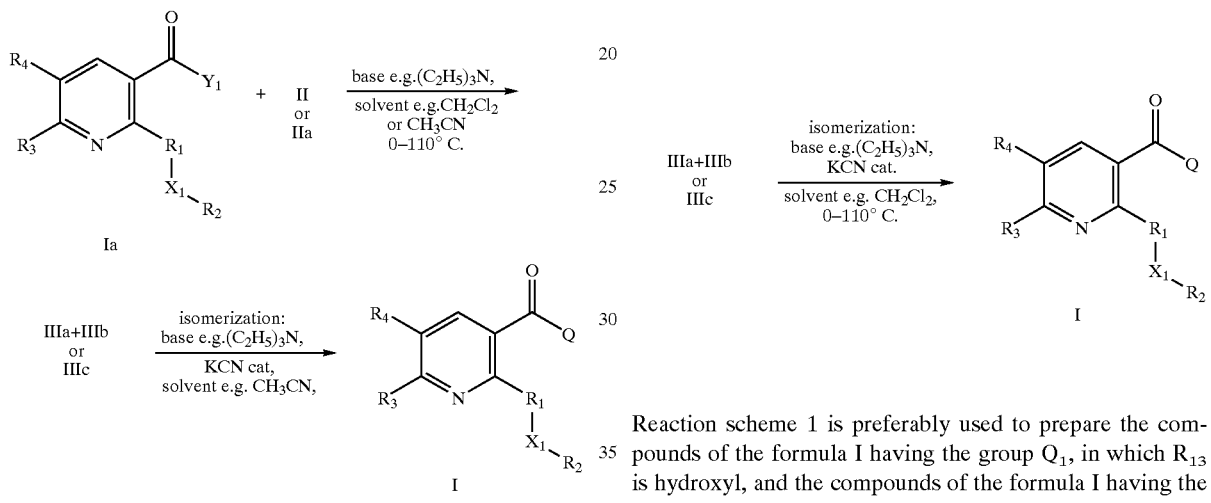

Reaction scheme 1 is preferably used to prepare the compounds of the formula I having the group $Q_1$, in which $R_{13}$ is hydroxyl, and the compounds of the formula I having the group $Q_2$, in which $R_{36}$ is hydroxyl.

Reaction scheme 2

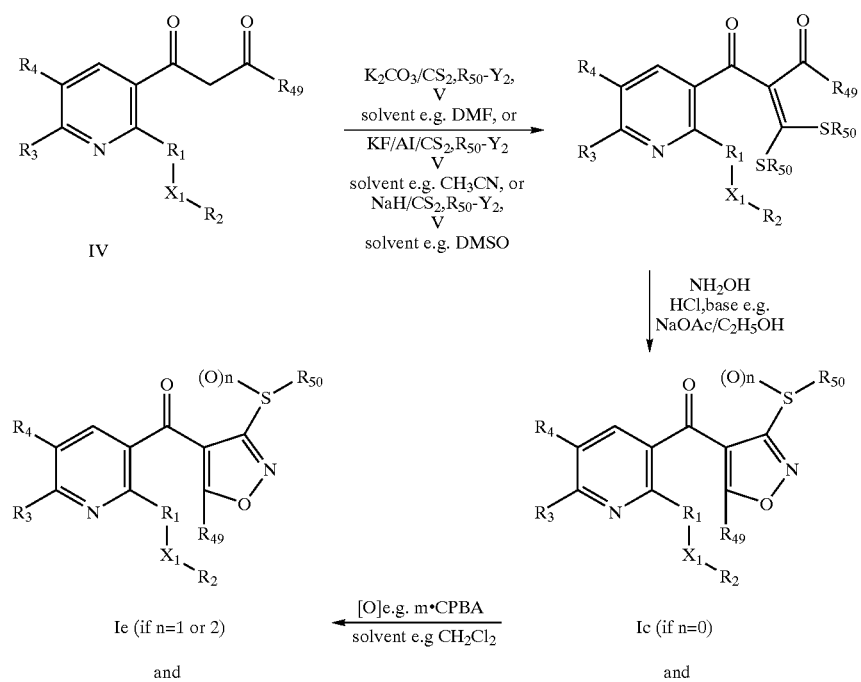

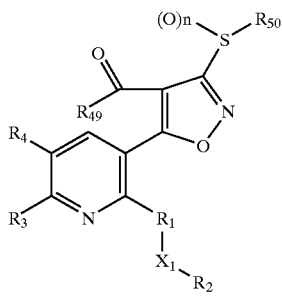

If (if n=1 or 2)

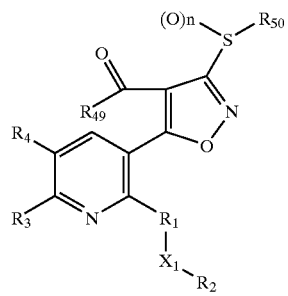

Id (if n=0)

Compounds of the formula I, in which p is 1, i.e. the corresponding N-oxides of the formula I, can be prepared by reacting a compound of the formula I, in which p is 0, with a suitable oxidizing agent, for example the $H_2O_2$/urea adduct in the presence of an acid anhydride, e.g. trifluoroacetic anhydride. Such oxidations are known from the literature, for example from *J. Med. Chem.*, 32 (12), 2561-73,1989 or WO 00/15615.

According to reaction scheme 1, route a), the carboxylic acid derivatives of the formula Ia in which $Y_1$ is a leaving group such as halogen, for example iodine, bromine, and in particular chlorine, N-oxyphthalimide or N,O-dimethylhydroxylamino or part of an activated ester, for example

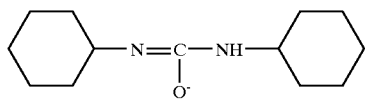

(formed from dicyclohexylcarbodiimide (DCC) and the corresponding carboxylic acid) or

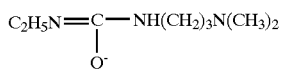

(formed from N-ethyl N'-(3-dimethylaminopropyl) carbodiimide (EDC) and the corresponding carboxylic acid) are used as starting materials for preparing the compounds of the formula I in which Q denotes the groups $Q_1$ and $Q_2$ and $R_{13}$ and $R_{36}$ are hydroxyl. The starting materials are reacted in an inert organic solvent such as a halogenated hydrocarbon, for example dichloromethane, a nitrile, for example acetonitrile, or an aromatic hydrocarbon, for example toluene, and in the presence of a base such as an alkylamine, for example triethylamine, an aromatic amine, for example pyridine or 4-dimethylaminopyridine (DMAP) with the dione derivatives of the formula II or pyrazoles of the formula IIa, to give the isomeric enol ethers of the formula IIIa, IIIb or IIIc. This esterification can be carried out at temperatures of from 0° C. to 110° C.

The isomerization of the ester derivatives of the formulae IIIa, IIIb and IIIc to derivatives of the formula I (in which $R_{13}$ and $R_{36}$ are hydroxyl) can be carried out, for example, similarly to EP-A0 353 187, EP-A-0 316 491 or WO 97146530 in the presence of a base such as an alkylamine, for example triethylamine, a carbonate, for example potassium carbonate, and a catalytic amount of DMAP or a source of cyanide, such as acetone cyanohydrin or potassium cyanide. In particular if a cyanide compound of the formula Ia ($Y_1$=cyano) is used, or in the presence of a catalytic amount of acetone cyanohydrin or potassium cyanide, the two reaction steps can be carried out in situ without isolating the intermediates III.

According to reaction scheme 1, route b), the desired derivatives of the formula I (in which $R_{13}$ and $R_{36}$ are hydroxyl) can be obtained, for example, similarly to E. Haslem, *Tetrahedron*, 2409–2433, 36, 1980, by esterifying the carboxylic acids of the formula Ib with the dione derivatives of the formula II or pyrazoles of the formula IIa in an inert solvent such as a halogenated hydrocarbon, for example dichloromethane, a nitrile, for example acetonitrile, or an aromatic hydrocarbon, for example toluene, in the presence of a base such as an alkylamine, for example triethylamine, and a coupling agent such as 2-chloro-1-methylpyridinium iodide. Depending on the solvent used, this esterification is carried out at temperatures of from 0° C. to 110° C., giving initially, as described under route a), the isomeric ester of the formula IIIa, IIIb or IIIc, which can be isomerized as described under route a), for example in the presence of a base and a catalytic amount of DMAP, or a source of cyanide, for example acetone cyanohydrin, to give the desired derivative of the formula I ($R_{13}$ and $R_{36}$= hydroxyl). The activated carboxylic acid derivatives of the formula Ia in reaction scheme 1 (route a), in which $Y_1$ is a leaving group such as halogen, for example bromine, iodine or, in particular, chlorine, can be prepared by known standard processes, for example those described in C. Ferri "Reaktionen der organischen Synthese" [Reactions of organic sythesis], Georg Thieme Verlag, Stuttgart, 1978, page 460 ff. Such reactions are generally known and described in the literature in different variations with respect to the leaving group $Y_1$.

The preparation of the compounds of the formula I, in which Q denotes the group $Q_3$, can be carried out according to reaction scheme 2 by reacting the β-diketone derivative of the formula IV for example similarly to *Synthesis* 1991, 301; ibid. 1988, 793; or *Tetrahedron* 32, 3055, 1976, with carbon disulfide in the presence of a base such as a carbonate, for example potassium carbonate, a metal hydride, for example sodium hydride, or potassium fluoride on aluminum, and an alkylating agent of the formula V, in which $Y_2$ is a leaving group such as halogen, for example iodine, bromine and, in particular, chlorine, $CH_3SO_2O$— or

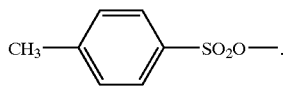

This reaction is expediently carried out in a solvent such as an amide, for example N,N-dimethylformamide (DMF), a sulfoxide, for example dimethyl sulfoxide (DMSO), or a nitrile, for example acetonitrile. The ketene thioacetal of the formula VI that is formed is cyclized with the aid of hydroxylamine hydrochloride in the presence of a base such as sodium acetate in a solvent such as an alcohol, for example ethanol, or an ether, for example tetrahydrofuran, to give the isomeric compounds of the formulae Ic and Id (in which n is 0). This cyclization reaction is carried out at temperatures of from 0° C. to 100° C. If appropriate, the compounds of the formulae Ic and Id in which n is 0 can be oxidized similarly to known standard processes as described, for example, in H. O. House, "Modern Synthetic Reactions", W. A. Benjamin, Inc., Menlo Park, Calif., 1972, pages 334–335 and 353–354, to give the corresponding sulfones and sulfoxides of the formulae Ie and if (n=1 or 2).

The compounds of the formula IV in reaction scheme 2 can be obtained by standard processes for example from the corresponding compounds of the formula Ia

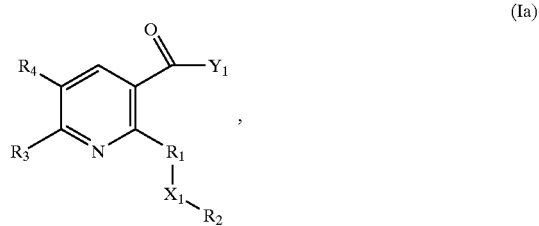

in which $R_1$, $R_2$, $R_3$, $R_4$, and $X_1$ are as defined above and $Y_1$ is a leaving group, for example halogen, for example by Claisen condensation, or from the compounds of the formula Ia by reaction with a ketocarboxylic acid salt of the formula VII

in which $R_{49}$ is as defined under formula I and $M^+$ is an alkali metal ion (cf., for example, WO 96/26192).

Compounds of the formula I, in which $R_1$ is, in particular $C_1$–$C_2$alkyl, can, for example, also be prepared by heating an N-oxide of the formula IX under known reaction conditions in the presence of an acid anhydride (see, for example, Konno, K.; Hashimoto, K.; Shirahama, H.; Matsumoto, T.; *Heterocycles* 1986, 24, 2169, or WO 00/15615) and hydrolyzing the resulting products (Ig) in a protic solvent, for example water or a water/methanol mixture, if appropriate in the presence of a base (for example lithium hydroxide or sodium hydroxide), and then converting the resulting alcohol X in the presence of a base, for example sodium hydride or potassium hydroxide, it appropriate in the presence of a phase-transfer catalyst or a crown ether, and an alkylating agent $R_2$—$Y_3$, in which $R_2$ is as defined under formula I and $Y_3$ is a leaving group, for example halogen or methyl sulfonate, in an aprotic solvent, for example, tetrahydrofuran or dimethylformamide, into the corresponding derivatives of the formula Ih (in which $X_1$ is oxygen). Compounds of the formula I, in which $R_2$ is $C_1$–$C_6$alkoxymethyl or 2-tetrahydropyranyl or 2-tetrahydrofuryl, can be prepared, for example, by treating an alcohol of the formula X with a vinyl ether of the formula $VE_1$, in which $R_{03}$, $R_{04}$, and $R_{05}$ are $C_1$–$C_6$alkyl or $R_{03}$ together with $R_{05}$ forms a $C_2$–$C_3$alkylene chain, in the presence of an acidic catalyst, for example para-toluenesulphonic acid, in an inert solvent, for example methylene chloride. Such reactions are generally known in the literature (see, for example, *Synthesis*, p. 169,1973). The two reaction sequences are demonstrated using the example below:

Reaction scheme 3

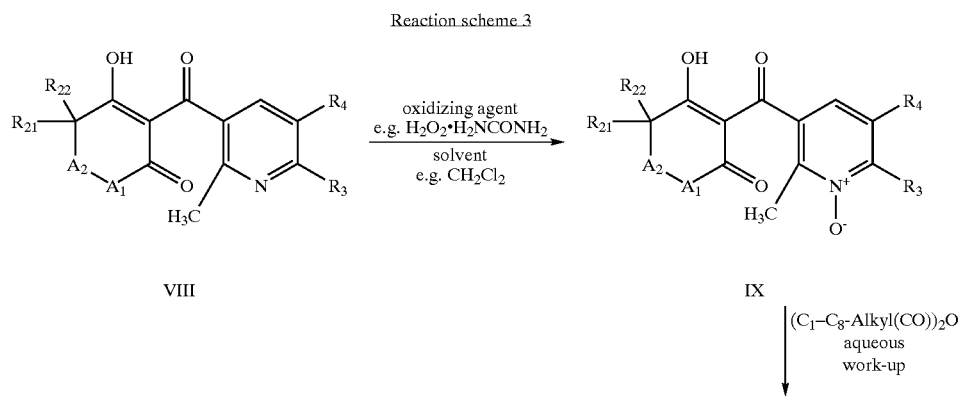

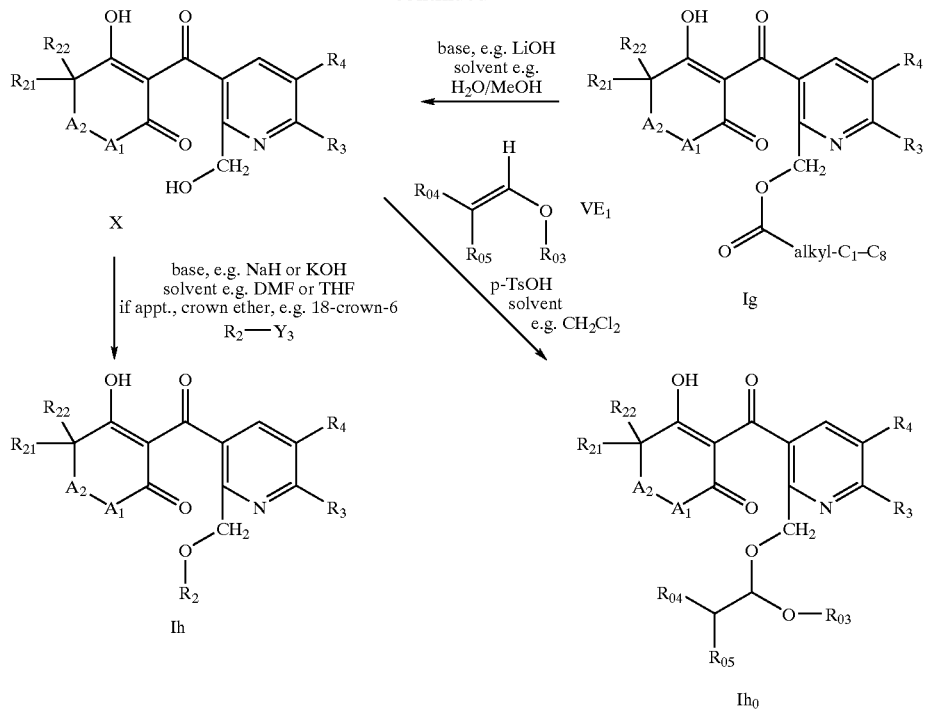

Compounds of the formula I, in which $R_1$ is, in particular, $C_1$—$C_2$alkyl or $C_1$–$C_2$haloalkyl, can, for example, also be prepared by oxidzing a compound of the formula XI, in which $R_{13}$ is in particular chlorine, $C_1$–$C_4$alkoxycarbonyloxy or benzoylcarbonyloxy (prepared similarly to WO 00/15615 or WO/0039094), under known halogenation conditions using, for example, N-bromosuccinimide or N-chlorosuccinimide in the presence of light and a free-radical initiator such as benzoyl peroxide to give the 1-bromo or 1-chloro, 1,1-dibromo or 1,1-dichloro compound and then refunctonalizing these compounds into the corresponding derivatives of the formula I, for example by reaction with a nucleophile $R_2$—Z, in which Z is, for example, —SH, —OH, —C(O)OH, —O—N(Rs,)H, —N($R_6$)—OH, —$SO_2$N($R_{52}$)H or —N($R_8$)H and $R_2$, $R_{52}$, $R_8$, $R_6$ and $R_{51}$ are as defined under formula I, in the presence of a base, for example sodium hydride, potassium hydroxide or potassium carbonate, followed by aqueous work-up. These reaction sequences, too, are demonstrated by the example below.

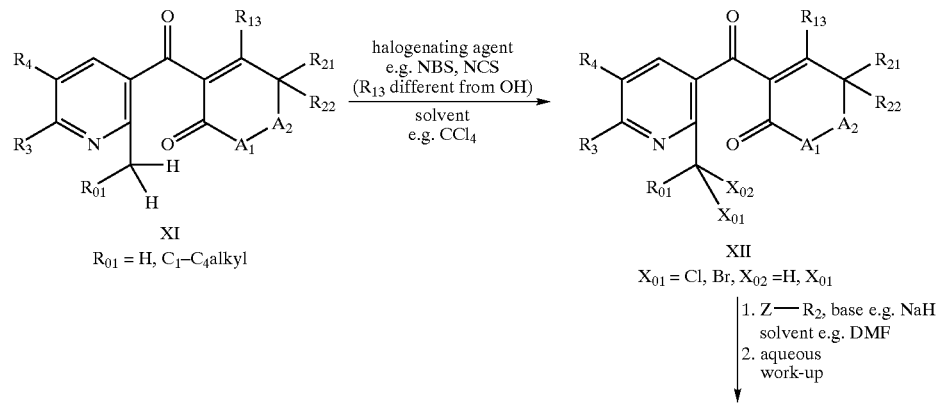

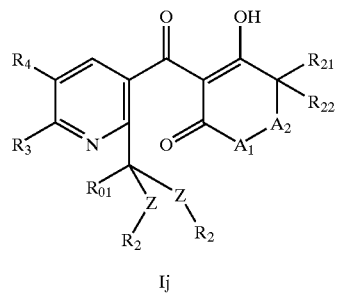

Ij

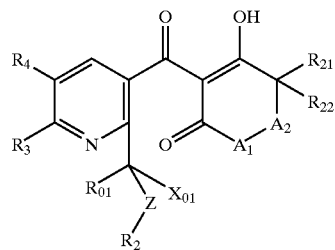

Ii $X_{01}$ = H, Cl, Br
$R_{01}$ = H, $C_1$–$C_4$alkyl
Z = S, O, $N(R_8)$, $N(R_{52})SO_2$, $N(R_8)O$, $ON(R_{51})$, $O(CO)$ Compounds of the formula I, in which Q denotes $Q_1$ or $Q_2$ and in which $R_{13}$ or $R_{36}$ are different from hydroxyl or halogen, can be prepared by conversion processes generally known from the literature, for example acylations or carbamoylations with appropriate acid chlorides from compounds of the formula I, in which $R_{13}$ or $R_{36}$ is hydroxyl, in the presence of a suitable base, or they can be prepared by nucleophilic substitution reactions on chlorides of the formula I, in which $R_{13}$ and $R_{36}$ are chlorine, the chlorides likewise being obtainable according to known processes by reaction with a chlorinating agent, such as phosgene, thionyl chloride or oxalyl chloride. The starting materials used are, for example, appropriately substituted amines, or hydroxylamines directly, or alkylsulfonamides, mercaptans, thiophenols, phenols, heterocyclic amines or heterocyclic thiols in the presence of a base, for example 5ethyl-2-methylpyridine, diisopropylethylamine, triethylamine, sodium bicarbonate, sodium acetate or potassium carbonate.

Compounds of the formula I, in which $R_{13}$ and $R_{36}$ contain thio groups, can be oxidized similarly to known standard processes using, for example, peracids, for example meta-chloroperbenzoic acid (m-CPBA) or peracetic acid, to give the corresponding sulfones and sulfoxides of the formula I. The degree of oxidation at the sulfur atom (SO— or $SO_2$—) can be controlled by the amount of oxidizing agent.

The resulting derivatives of the formula I, in which $R_{13}$ and $R_{36}$ are different from hydroxyl, can likewise occur in different isomeric forms which, it appropriate, can be isolated in pure form. Accordingly, the invention also embraces all of these stereoisomeric forms. Examples of these isomeric forms are the formulae I', I" and I''' below in which Q denotes the group $Q_1$.

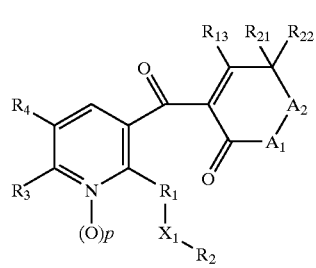

I'

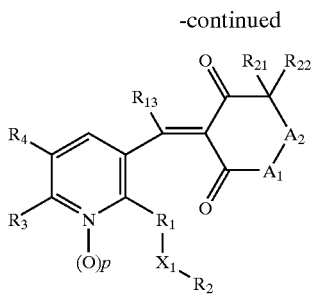

I"

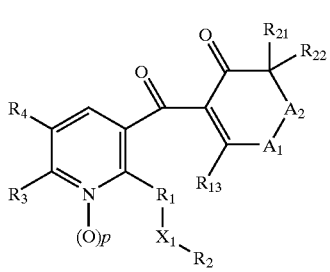

I'''

The compounds of the formulae II and IIa are known and can be prepared similarly as described, for example, in WO 92/07837, JP 10265441, DE-A-3818958, EP-A-0 338 992, DE-A-3902818, EP-A-0 278 742, WO 98129412, JP 02059566, US-A-5,089,046, GB-A-2205316, WO 00/27821 or EP-A-0 384 736.

The required intermediates of the formula Ib (or Ik, Il or Im) are synthesized similarly to known processes as described, for example, in WO 00/15615, WO/00/39094 or WO 97/46530, or they can be prepared for example, according to generally known conversion methods such as the Stille (see, for example *Angew. Chem.* 1986, 98(6), 504–19), Heck (see, for example, *Angew. Chem.* 1994, 106 (23124), 2473–506), Sonogashira (see, for example, "*Comprehensive Organometallic Synthesis*", Pergamon Verlag, Oxford, Vol 3, 1991, page 521 ff.) or Wittig (for example C. Ferri "*Reaktionen der organischen Synthese*", Georg Thieme Verlag, Stuttgart, 1978, p. 354 ff.) reactions, starting from halogen derivatives of the formula XIV (preparation as described in WO 00/15615 or WO0039094) or XVll (preparation similar to EP 522392) (reaction scheme 5):

Reaction scheme 5
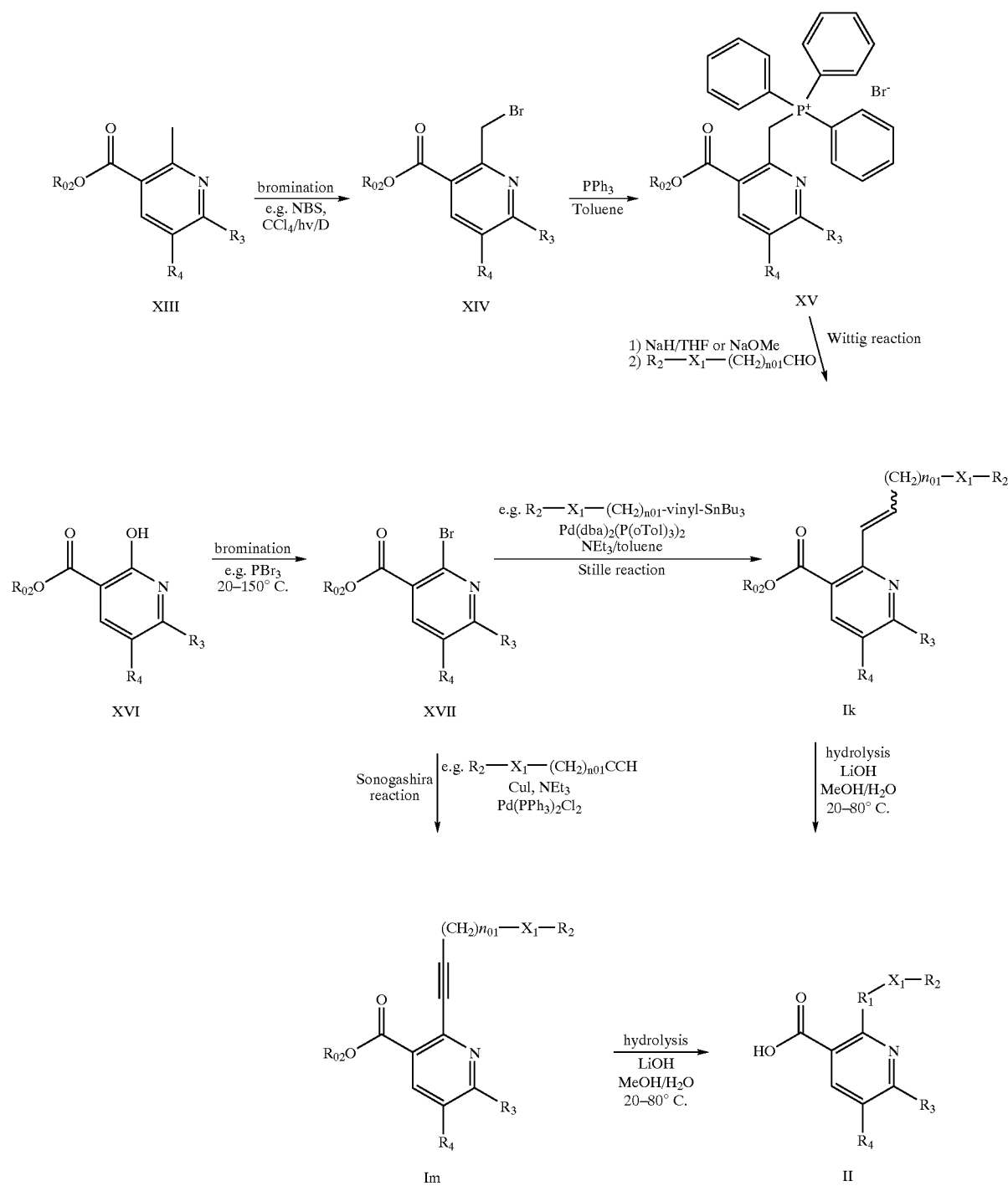
$R_{02}$ = $C_1$–$C_6$alkyl, hydrogen
$n_{01}$ = 1 to 4
Intermediates of the formula Ib, in which $R_1$, $R_2$, $R_3$, $R_4$ and $X_1$ are as defined under formula I, can also be prepared by the method according to reaction scheme 6:

Reaction scheme 6
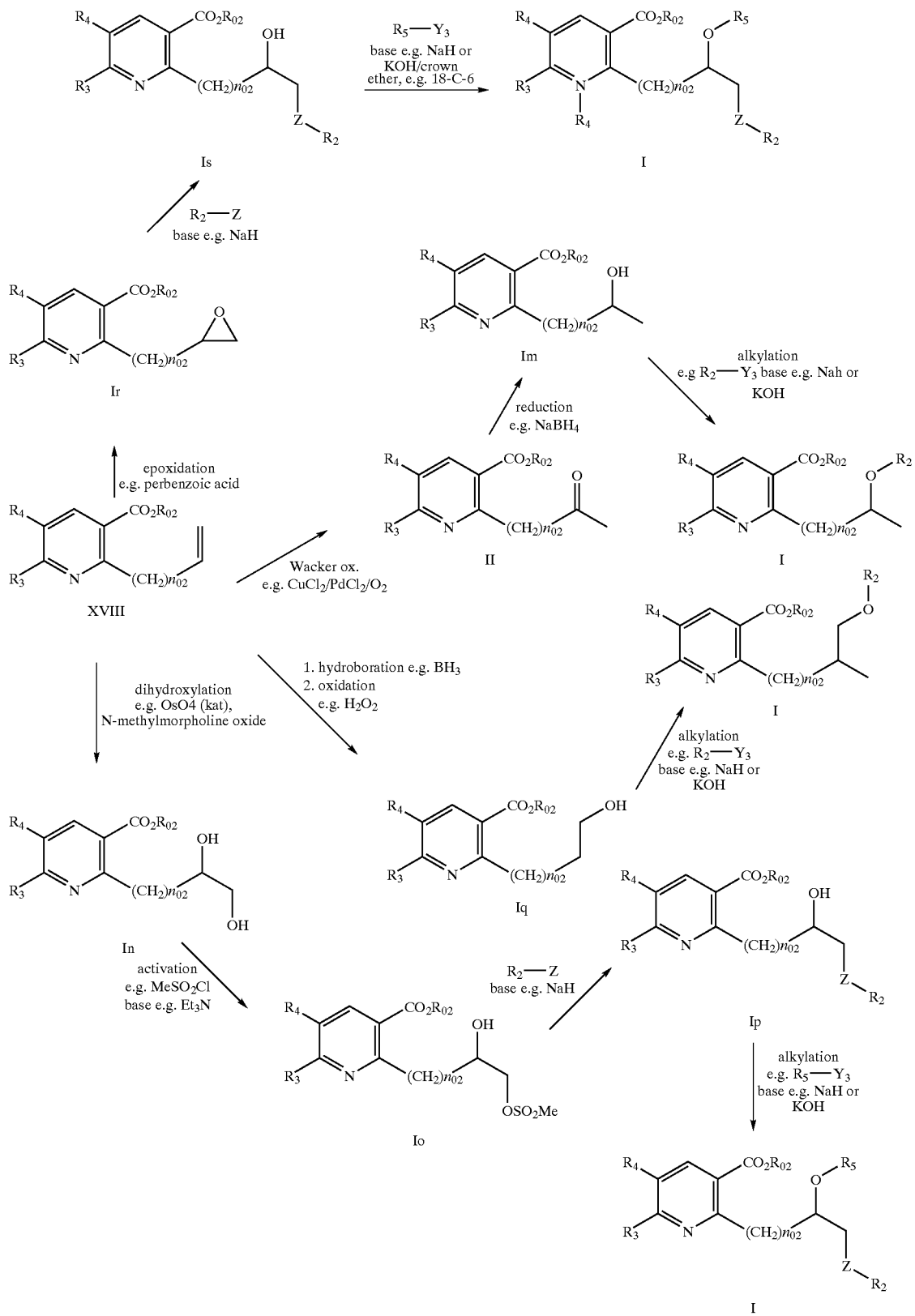
$n_{02}$ = 0 to 4
$R_{02}$ = $C_1$–$C_6$alkyl, hydrogen Using generally known oxidation methods such as dihydroxylation, Wacker oxidation, epoxidation, hydroboration with subsequent oxidation, starting with vinyl or allyl compounds of the formula XVIII (preparation as described in WO 00/15615 or WO/0039094), intermediates of the formulae Il, In, Iq and Ir are obtained which can be converted by conversion processes known to the person skilled in the art (for example alcohol activation, for example as sulfonate, alkylation, for example using an alkylating agent $R_2$—$Y_3$ or $R_5$—$Y_3$, in which $R_2$ and $R_5$ are as defined under formula I and $Y_3$ is a leaving group, for example halogen), in the presence of a base, or using nucleophile reactions, for example with a nucleophile Z—$R_2$, in which Z and $R_2$ are as defined above, into compounds of the formula I.

Intermediates of the formula Ib, in which $R_1$ is $C_1$–$C_2$alkyl and $R_2$, $R_3$, $R_4$ and $X_1$ are as defined under formula I, can also be prepared by reacting a compound of the formula XIVa, in which $R_3$ and $R_4$ are as defined above under formula I and $Y_4$ is halogen, with a nucleophile $R_2$—Z, in which Z is —SH, —OH, —C(O)OH, —O—N($R_{51}$)H, —N($R_6$)—OH —SO$_2$N($R_{52}$)H or —N($R_8$)H and $R_2$, $R_{52}$, $R_8$, $R_6$, $R_{51}$ are as defined above under formula I, in the presence of a base such as sodium hydride or an alkaline earth metal oxide or carbonate in an inert solvent such as dimethylformamide or THF at temperatures between −5 and 160° C., or, to prepare the corresponding sulfinyl or sulfonyl derivatives of the formula Iu, by reacting with an oxidizing agent such as m-chloroperbenzoic acid or sodium periodate, or sodium perborate, with, depending on the degree of oxidation, temperature control known to the person skilled in the art (for example −30° C.–+50° C. for n=1 and −20° C.–+100° C. for n=2 respectively), in an inert solvent such as dichloromethane, to give compound of the formula Iv. In reaction scheme 7 below, this is illustrated in more detail for the case Z=OH, SH, SO$_2$N($R_{52}$)H and N($R_8$)H:

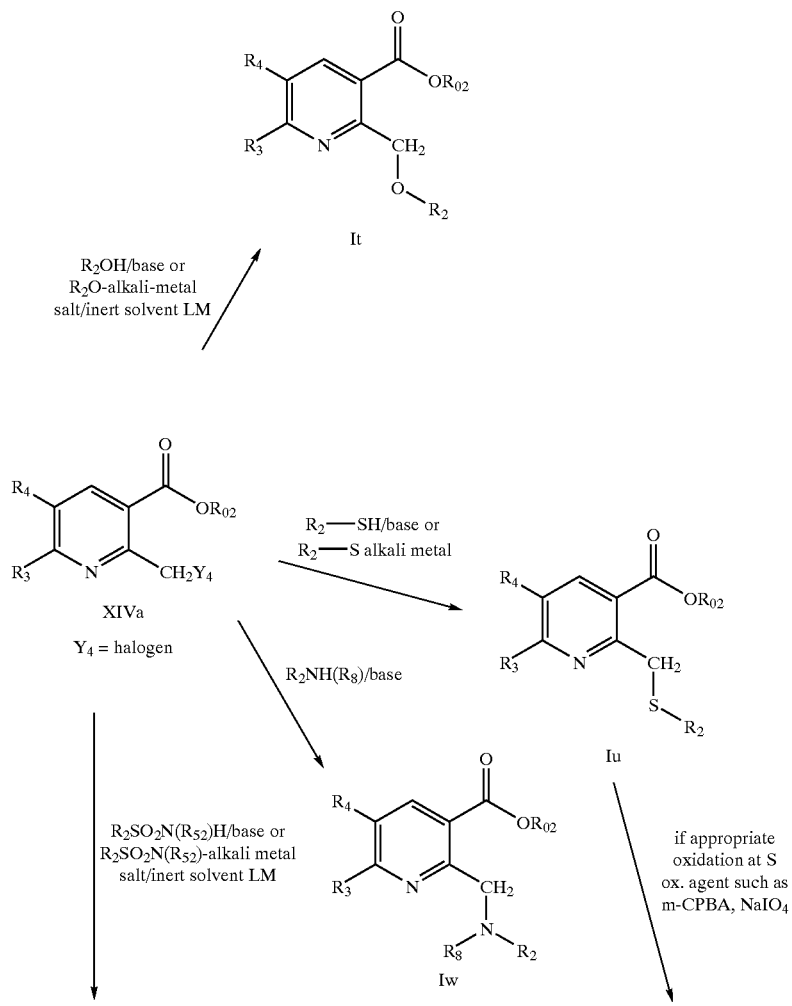

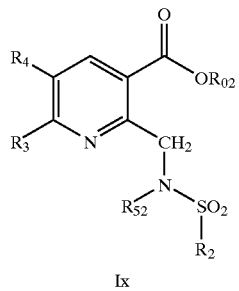

Ix

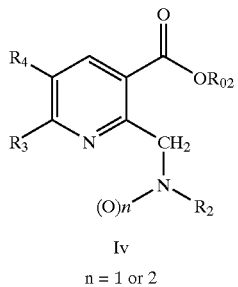

Iv n = 1 or 2

Intermediates of the formula I, in which Q denotes a group $OR_{02}$ ($R_{02}=C_1-C_6$alkyl), can be converted by hydrolysis using, for example, a base, for example LiOH, in a protic solvent, for example $H_2O$ or $H_2O$/methanol mixtures, into products of the formula Ib.

For preparing all further compounds of the formula I functionalized according to the definitions of $R_1$, $R_2$, $R_3$, $R_4$ and $X_1$, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichforomethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothenmic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 1 8-crown-6, or a tetraalkylammonium salt.

The compounds of the formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

All application methods which are conventionally used in agriculture, for example pre-emergence application, post-emergence application and seed treatment, as well as various methods and techniques, for example the controlled release of active ingredients, are suitable for the use according to the invention of the compounds of the formula I or of compositions comprising them. To this end, the active ingredient in solution is applied to mineral carriers for granules or to polymerized granules (urea/formaldehyde) and dried. If appropriate, an additional coating can be applied (coated granules), which allows the active ingredient to be released in a controlled manner over a specific period of time. The compounds of the formula I can be employed as herbicides as such, i.e. as obtained from synthesis. However, they are preferably processed in the customary manner together with the auxiliaries conventionally used in the art of formulation, for example to give emulsifiable concentrates, directly sprayable or dilutable solutions, dilute emulsions, wettable powders, soluble powders, dusts, granules or microcapsules. Such formulations are described, for example, in WO 97/34485 on pages 9 to 13. The application methods such as spraying, atomizing, dusting, wetting, scattering or pouring, as well as the type of composition, are chosen to suit the intended aims and the prevailing circumstances.

The formulations, i.e. the compositions, preparations or products which comprise the active ingredient of the formula I or at least one active ingredient of the formula I and, as a rule, one or more solid or liquid formulation auxiliaries, are prepared in the known manner, for example by intimately mixing and/or grinding the active ingredients together with the formulation auxiliaries, for example solvents or solid carriers. Furthermore, surfacEactive compounds (surfactants) may additionally be used when preparing the formulations. Examples of solvents and solid carriers are indicated for example in WO 97/344 85 on page 6.

Suitable surfaceactive compounds are, depending on the nature of the active ingredient of the formula I to be formulated, nonion Ic, cationic and/or anionic surfactants and surfactant mixtures which have good emulsifying, dispersing and wetting properties. Examples of suitable anionic, nonionic and cationic surfactants are enumerated, for example, in WO 97/34485 on pages 7 and 8. The surfactants conventionally used in the art of formulation which are described, inter alia, in "McCutcheonss Detergents and Emulsifiers Annual" MC Publishing Corp., Ridgewood N.J., 1981, Stache, H., "Tensid-Taschenbuch" [Surfactants Guidet], Carl Hanser Verlag, Munich/Nienna, 1981 and M. and J. Ash, "Encyclopedia of Surfactants", Vol I–III, Chemical Publishing Co., New York, 1980–81 are furthermore also suitable for preparing the herbicidal corpositions accor ding t o the invention.

As a rule, the herbicidal formulations comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant. While concentrated compositions are more preferred as commercially available goods, the end consumer uses, as a rule, dilute compositions. The compositions can also comprise further additives such as stabilizers, for example epoxidized or non-epoxidized vegetable oils (epoxidized coconut oil, rapeseed oil or soya oil), antifoams, e.g. silicone oil, preservatives, viscosity regulators, binders, tackifiers and fertilizers or other active ingredients.

As a rule, the active ingredients of the formula I are applied to the plant or its environment at rates of 0.001 to 4 kg/ha, in particular 0.005 to 2 kg/ha. The dosage required for the desired action can be determined by experiments. It depends on the type of the action, the developmental stage of the crop plant and of the weed, and on the application (location, timing, method) and can, owing to these parameters, vary within wide limits.

The compounds of the formula I are distinguished by herbicidal and growth-inhibitory properties which allow them to be employed in crops of useful plants, in particular in cereals, cotton, soya, sugar beet, sugar cane, plantation crops, rapeseed, maize and rice and for the nonselectve control of weeds. Crops are also to be understood as including those which have been rendered tolerant to herbicides or classes of herbicides by means of conventional plant-breeding or genetic-engineering methods. The weeds to be controlled may be both mono- and dicotyledonous weeds such as Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The examples which follow illustrate the invention in greater detail without limiting it

PREPARATION EXAMPLES

Example H1

Preparation of Ethyl 2-bromomethyl6-trifluoromethylnicotinate 434.4 g (1.866 mol) of ethyl 2-methyl-6trifluoromethylnicotinate (preparation similar to *Heterocycles* 129, 46, 1997) and 398.5 g (2.239 mol) of N-bromosuccinimide in 3 500 ml of carbon tetrachloride in the presence of 30.6 g (0.1866 mol) of α,α-azaisobutyronitrile are heated at 75° C., with irradiation from a 150 Watt lamp. After 3 hours, the reaction is terminated, the mixture is cooled to 15° C. and precipitated succinimide is removed by filtration. After evaporation of the solvent, the residue is distilled under reduced pressure. This gives ethyl 2-bromomethyl-6-trifluoromethylnicotinate as an oily product (260.2 g, 44.7% of theory, b.p. 74° C./0.04 mmHg).

Example H2

2-(2-Methoxyethoxymethyl)-6-trifluoromethylnicotinic acid

At room temperature, 177.2 g of ethyl 2-bromomethyl-6trifluoromethylnicotinate are dissolved in 3000 ml of toluene and reacted with 398 ml (1.704 mol) of a 21% ethanolic solution of sodium ethoxide. After 8 hours at room temperature, 1500 ml of ethanol and 100 ml of 30% aqueous sodium hydroxide solution are added with vigorous stirring, and the reaction mixture is stirred at this temperature for another 4 hours. The reaction mixture is poured into water and extracted with ethyl acetate, and the aqueous phase is acidified to pH 1. Following extraction with ethyl acetate, drying over sodium sulfate, evaporation under reduced pressure and trituration with hexane, pure 2-(2-methoxyethoxymethyl)-6-trifluoro-methylnicotinic acid is obtained in the form of white crystals of melting point 62–63° C.

Example H3

4-Hydroxy-3-[2-(2-methoxyethoxymethyl)-6trifluoromethylpyridine-3-carbonyl]-bicyclo[3.2.1] oct-3-en-2-one 24.9 g (0.1 mol) of 2-(2-methoxyethoxymethyl)-6-trifluoromethylnicotinic acid are dissolved in 200 ml of methylene chloride and 20 ml of oxalyl chloride, and 0.1 ml of dimethylformamide is then added dropwise. After the strong evolution of gas has ceased, triethylamine (27.9 ml, 0.2 mol), dimethylaminopyridine (1.22 g, 0.01 mol) and 15.2 g (0.11 mol) of bicyclo[3.2.1]octane-2,4-dione are added at a temperature of from 0 to 5° C. After 3 hours at 22° C., the reaction mixture is extracted with 2 N hydrochloric acid. The methylenechloride phase is separated off, washed with water and then extracted with 10% aqueous sodium bicarbonate solution, dried over sodium sulfate and concentrated. This gives 36.9 g (100% of theory) of 4-oxobicyclo[3.2.1]oct-2-en-2-yl 2-(2-methoxyethoxymethyl)-6-trifluoromethyl-nicotininate as an oil, which can be used further without purification.

36.9 g (0.1 mol) of 4-oxobicyclo[3.2.1]oct-2-en-2-yl 2-(2-methoxyethoxymethyl)-6-trifluoromethylnicotinate and 27.9 ml (0.2 mol) of triethylamine are dissolved in 400 ml of acetonitrile. At a temperature of 22° C., 0.92 ml (0.01 mol) of acetone cyanohydrin is added. After 18 hours at 22° C., the reaction mixture is poured into a water/2 N hydrochloric acid mixture and extracted with ethyl acetate. The ethyl acetate phase is washed with water and then with concentrated sodium chloride solution, dried over sodium sulfate and concentrated, and the residue is triturated with hexane. Filtration gives 27.9 g (75.6% of theory) of 4-hydroxyl-3-[2-(2-methoxyethoxymethyl)-6-trifluoromethylpyridine-3-carbonyl]bicyclo[3.2. 1 ]oct-3-en-2-one in the form of white crystals (m.p. 55–56° C.).

Example H4

3-(2-Hydroxy-4-oxobicyclo[3.2.1]oct-2-en-3carbonyl)-6-trifluoromethylpyridin-2-yl methyl acetate 5.0 g (1 mmol) of 4-hydroxy-3-(2-methyl-1-oxy-6-trifluoromethylpyridin-3carbonyl)-bicyclo[3.2.1]oct-3-en-2-one (preparation as described in WO 00/15615) are dissolved in 100 ml of toluene and, in the presence of 6.9 ml (0.073 mol) of acetic anhydride, heated at reflux temperature for 1 0 hours. The mixture is then partitioned between water and ethyl acetate and the organic phase is dried over sodium sulfate and concentrated under reduced pressure. The residue that remains is chromatographed on silica gel. The viscous oil obtained by eluting with a mixture of toluene, ethyl alcohol, dioxane, triethylamine and water (100:40:20:20:5 parts by volume) is dissolved in ethyl acetate and washed successively with 10% hydrochloric acid and water. The organic solution is dried over $Na_2SO_4$ and concentrated, giving 2.14 g (38%) of pure 3-(2-hydroxy-4-oxobicyclo[3.2.1]oct-2-ene3-carbonyl)6-trifluoromethylpyridin-2-ylmethyl acetate in the form of an oil. $^1$H-NMR (250 MHz, $CDCl_3$): 17.06 (s), 1H; 7.67 (s), 2H; 5.27 (d, J=12.5 Hz), 1H; 5.20 (d, J=12.5 Hz), 1H; 3.18, (t, J=5.0 Hz), 1H; 2.92, (t, J=5.0 Hz), 1 H; 2.29–1.98 (m), 4H; 2.00, (s), 3H; 1.81–173 ppm (m), 2H.

Example H5

4-Hydroxy-3-(2-oxiranylmethoxymethyl-6-trfluoromethylpyridine-3-carbonyl)-bicyclo[3.2.1]oct-3-en-2-one 5 g (0.01 3 mol) of 3(2-hydroxy4-oxobicyclo[3.2.1 ]oct-2-ene-3-carbonyl)-6trifluoromethylpyridin-2-ylmethyl acetate are dissolved in 60 ml of methanol/water (3:1 mixture), and 1.4 g (0.046 mol) of lithium hydroxide hydrate are added a little at a time at a temperature of 22° C. After 3 hours at 22° C., the reaction mixture is poured into ethyl acetate and 10% hydrochloric acid, and the organic phase is washed three times with water, dried with sodium sulfate and concentranted. This gives 4.1 g of 4-hydroxy-3-(2-hydroxymethyl-6-trifluoromethylpyridine-3-carbonyl)bicyclo[3.2.1]oct-3-en-2one as an oil which can be reacted further without purification.

1.5 g of 4-hydroxymethyl-6-trifluoromethylpyridine-3-carbonyl)-bicyclo[3.2.1]oct-3-en-2-one are dissolved in 15 ml of dimethylformamide and, at room temperature, treated with 0.4 g of sodium hydride (80% suspension in oil, 0.013 mol), a little at a time. After 15 minutes at a temperature of 22° C., 3 ml (0.036 mol) of epibromohydrin are added dropwise, and the reaction mixture is stirred at this temperature for another 18 hours. Ethyl acetate is then added, and the mixture is acidified to pH 3 using 10% hydrochloric acid and extracted with ethyl acetate. The organic phase is dried over sodium sulfate and the crude product is purified chromatographically (mobile phase: toluene/ethyl alcohol/dioxane/triethylamine/water 100:40:20:20:5 parts by volume). This gives the title compound (triethylamine salt) in the form of a yellowish resin, which is released similarly to example H4. Trituration with hexane gives 600 mg of pure 4-hydroxy-3-(2-oxiranylmethoxy-methyl-6-trifluoromethylpyridin-3-carbonyl)bicyclo[3.2.1]oct-3-en-2-one of melting point 54–56° C.

Example H6

(5-Hydroxy-1.3dimethyl-1H-pyrazol-4-yl)-[2-(2-methoxyethoxymethyl)-6-trifluoromethylpyridin-3-yl]methanone 1.0 g (0.004 mol) of 2-(2-methoxyethoxymethyl)-6-trifluoromethylnicotinic acid is dissolved in 10 ml of oxalyl chloride. Three drops of dimnethylformamide are added, and the mixture is stirred at room temperature for 1 hour. The mixture is then concentrated using a rotary evaporator, and the residue (2-(2-methoxyethoxymethyl)-6-trifluoromethylnicotinoyl chloride) is taken up in 10 ml of methylene chloride. At a temperature of 0° C., 0.84 ml (0.006 mol) of triethylamine and 0.45 g (0.004 mol) of 2,5dimethyl-2,4-dihydropyrazol-3one are added. After 2 hours at a temperature of 22° C., the solvent is removed using a vacuum rotary evaporator, and the residue that remains is dissolved in 10 ml of acetonitrile and, to rearrange the intermediate (2,5-dimethyl-2H-pyrazol-3-yl 2-(2-methoxyethoxymethyl)-6-trifluoromethylnicotinate), admixed with 0.1 ml of acetone cyanohydrin and 1.13 ml (0.008 mol) of triethylamine. The reaction solution is stirred at room temperature for four hours and then concentrated. The syrup that remains is chromatographed on silica gel. The viscous oil obtained by eluting with a mixture of toluene, ethyl alcohol, dioxane, triethylamine and water (100:40:20:20:5 parts by volume) is dissolved in ethyl acetate and washed successively with 10% hydrochloric acid and water. The organic solution is dried over $Na_2SO_4$ and concentrated, giving 0.93 g of (5-hydroxy-1,3-dimethyl-1H-pyrazol-4yl)-[2-(2-methoxyethoxymethyl)-6-trifluoromethylpyridin-3-yl]methanone in the form of a viscous oil.

$^1$H NMR (300 MHz, $CDCl_3$, δ in ppm): 7.81, (d, J=6 Hz), 1H; 7.74, (d, J=6 Hz), 1H; 4.84, (s), 2H; 2H: 3.71, (s), 3H; 3.59, (t, J=6 Hz) 2H; 3.38, (dd, J 4.0, 3.0 Hz), 1H; 3.26, (s), 3H; 1.82 ppm, (s), 1 H.

Preferred compounds of the formula I and their intermediates are listed in the tables below.

In the table below, the left-hand valency of the radical $R_1$ is attached to the pyridine ring. If no free valency is indicated in the substituent $R_2$, as, for example, in the case of

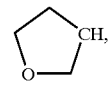

the point of attachment is at the "CH" carbon atom.

In the table below, the compounds of the formula I are represented as:

A-Q where the formula A

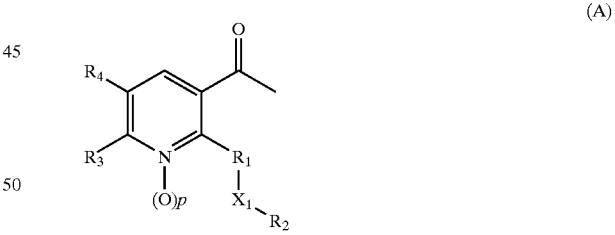

denotes the following radicals:

| Radical | $R_1$ | $R_2$ | $R_4$ | $R_3$ | $X_1$ | p |
|---------|-------|-------|-------|-------|-------|---|
| A1 | $CH_2$ | $CH_3$ | H | $CF_3$ | O | 0 |
| A2 | $CH_2$ | $CH_2CH_3$ | H | $CF_3$ | O | 0 |
| A3 | $CH_2$ | $(CH_3)_2CH$ | H | $CF_3$ | O | 0 |
| A4 | $CH_2$ | $PhCH_2$ | H | $CF_3$ | O | 0 |
| A5 | $CH_2$ | $CH_3$ | H | $CF_3$ | S | 0 |
| A6 | $CH_2$ | $CH_3$ | H | $CF_3$ | SO | 0 |
| A7 | $CH_2$ | $CH_3$ | H | $CF_3$ | $SO_2$ | 0 |
| A8 | $CH_2$ | $CH_3OCH_2$ | H | $CF_3$ | O | 0 |

-continued

| Radical | $R_1$ | $R_2$ | $R_4$ | $R_3$ | $X_1$ | p |
|---|---|---|---|---|---|---|
| A9  | $CH_2$ | $CH_3CH_2OCH_2$       | H | $CF_3$ | O | 0 |
| A10 | $CH_2$ | $CH_3OCH_2CH_2$       | H | $CF_3$ | O | 0 |
| A11 | $CH_2$ | $CH_3CH_2OCH_2CH_2$   | H | $CF_3$ | O | 0 |
| A12 | $CH_2$ | $CH_3OC(CH_3)_2CH_2$  | H | $CF_3$ | O | 0 |
| A13 | $CH_2$ | $CH_3OCH(CH_3)CH_2$   | H | $CF_3$ | O | 0 |
| A14 | $CH_2$ | $CH_3OCH_2CH(CH_3)$   | H | $CF_3$ | O | 0 |
| A15 | $CH_2$ | $CH_3OCH_2C(CH_3)_2$  | H | $CF_3$ | O | 0 |
| A16 | $CH_2$ | $CH_3OCH(CH_3)$       | H | $CF_3$ | O | 0 |
| A17 | $CH_2$ | $CH_3OC(CH_3)_2$      | H | $CF_3$ | O | 0 |
| A18 | $CH_2$ | $HC{\equiv}CCH_2$     | H | $CF_3$ | O | 0 |
| A19 | $CH_2$ | $H_2C{=}CHCH_2$       | H | $CF_3$ | O | 0 |
| A20 | $CH_2$ | $CH_3C{\equiv}CCH_2$  | H | $CF_3$ | O | 0 |
| A21 | $CH_2$ | cyclopropyl-CH        | H | $CF_3$ | O | 0 |
| A22 | $CH_2$ | oxiranyl-CH           | H | $CF_3$ | O | 0 |
| A23 | $CH_2$ | cyclobutyl-CH         | H | $CF_3$ | O | 0 |
| A24 | $CH_2$ | oxetanyl-CH           | H | $CF_3$ | O | 0 |
| A25 | $CH_2$ | cyclopentyl-CH        | H | $CF_3$ | O | 0 |
| A26 | $CH_2$ | tetrahydrofuranyl-CH  | H | $CF_3$ | O | 0 |
| A27 | $CH_2$ | cyclohexyl-CH         | H | $CF_3$ | O | 0 |
| A28 | $CH_2$ | tetrahydropyranyl-CH  | H | $CF_3$ | O | 0 |
| A29 | $CH_2$ | tetrahydropyranyl-CH  | H | $CF_3$ | O | 0 |
| A30 | $CH_2$ | tetrahydropyranyl-CH  | H | $CF_3$ | O | 0 |
| A31 | $CH_2$ | 1,3-dioxanyl-CH       | H | $CF_3$ | O | 0 |
| A32 | $CH_2$ | phenyl                | H | $CF_3$ | O | 0 |

-continued
| Radical | R₁ | R₂ | R₄ | R₃ | X₁ | p |
|---------|-----|-----|-----|-----|-----|---|
| A33 | CH₂ | 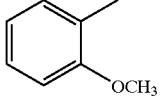 | H | CF₃ | O | 0 |
| A34 | CH₂ | 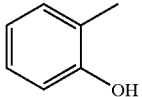 | H | CF₃ | O | 0 |
| A35 | CH₂ | 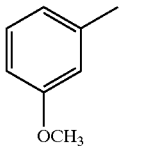 | H | CF₃ | O | 0 |
| A36 | CH₂ | 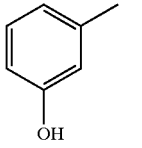 | H | CF₃ | O | 0 |
| A37 | CH₂ | 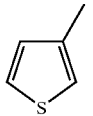 | H | CF₃ | O | 0 |
| A38 | CH₂ | 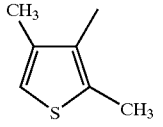 | H | CF₃ | O | 0 |
| A39 | CH₂ | 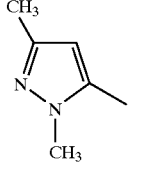 | H | CF₃ | O | 0 |
| A40 | CH₂ | 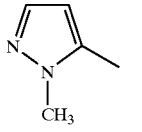 | H | CF₃ | O | 0 |
| A41 | CH₂ | 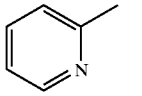 | H | CF₃ | O | 0 |
| A42 | CH₂ | 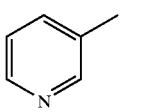 | H | CF₃ | O | 0 |
| A43 | CH₂ | 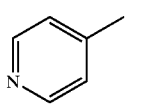 | H | CF₃ | O | 0 |

-continued

| Radical | R₁ | R₂ | R₄ | R₃ | X₁ | p |
|---|---|---|---|---|---|---|
| A44 | CH₂ | 2-methyl-3-methoxypyridinyl | H | CF₃ | O | 0 |
| A45 | CH₂ | 2-methyl-3-hydroxypyridinyl | H | CF₃ | O | 0 |
| A46 | CH₂ | 2-methoxy-3-methylpyridinyl | H | CF₃ | O | 0 |
| A47 | CH₂ | 2-hydroxy-3-methylpyridinyl | H | CF₃ | O | 0 |
| A48 | CH₂ | 3-methoxy-4-methylpyridinyl | H | CF₃ | O | 0 |
| A49 | CH₂ | 3-hydroxy-4-methylpyridinyl | H | CF₃ | O | 0 |
| A50 | CH₂ | 3-methyl-4,5-dihydroisoxazolyl | H | CF₃ | O | 0 |
| A51 | CH₂ | 3-methylisoxazolyl | H | CF₃ | O | 0 |
| A52 | CH₂ | 5-fluoro-2-methyl-3-methoxyphenyl | H | CF₃ | O | 0 |
| A53 | CH₂ | 4-methyl-3-methoxy-cyanophenyl | H | CF₃ | O | 0 |

-continued
| Radical | R₁ | R₂ | R₄ | R₃ | X₁ | p |
|---|---|---|---|---|---|---|
| A54 | CH₂ | 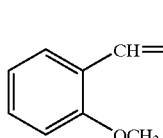 | H | CF₃ | O | 0 |
| A55 | CH₂ | 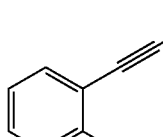 | H | CF₃ | O | 0 |
| A56 | CH₂ | 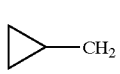 | H | CF₃ | O | 0 |
| A57 | CH₂ | 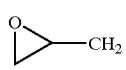 | H | CF₃ | O | 0 |
| A58 | CH₂ | 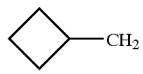 | H | CF₃ | O | 0 |
| A59 | CH₂ | 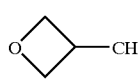 | H | CF₃ | O | 0 |
| A60 | CH₂ | 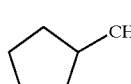 | H | CF₃ | O | 0 |
| A61 | CH₂ | 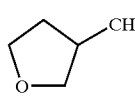 | H | CF₃ | O | 0 |
| A62 | CH₂ | 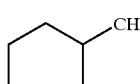 | H | CF₃ | O | 0 |
| A63 | CH₂ | 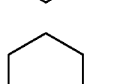 | H | CF₃ | O | 0 |
| A64 | CH₂ | 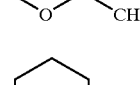 | H | CF₃ | O | 0 |
| A65 | CH₂ | 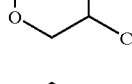 | H | CF₃ | O | 0 |
| A66 | CH₂ | 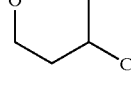 | H | CF₃ | O | 0 |
| A67 | CH₂ | 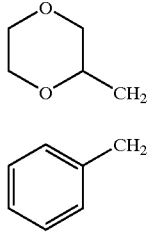 | H | CF₃ | O | 0 |

-continued
| Radical | R₁ | R₂ | R₄ | R₃ | X₁ | p |
|---|---|---|---|---|---|---|
| A68 | CH₂ | 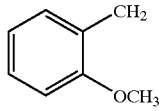 | H | CF₃ | O | 0 |
| A69 | CH₂ | 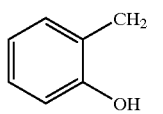 | H | CF₃ | O | 0 |
| A70 | CH₂ | 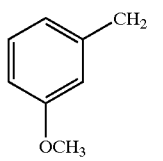 | H | CF₃ | O | 0 |
| A71 | CH₂ | 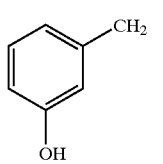 | H | CF₃ | O | 0 |
| A72 | CH₂ | 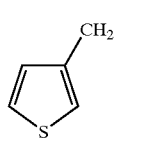 | H | CF₃ | O | 0 |
| A73 | CH₂ | 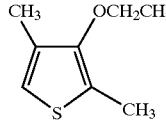 | H | CF₃ | O | 0 |
| A74 | CH₂ | 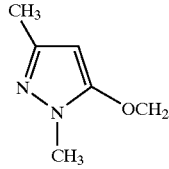 | H | CF₃ | O | 0 |
| A75 | CH₂ | 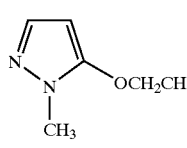 | H | CF₃ | O | 0 |
| A76 | CH₂ | 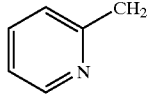 | H | CF₃ | O | 0 |
| A77 | CH₂ | 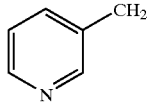 | H | CF₃ | O | 0 |
| A78 | CH₂ | 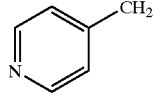 | H | CF₃ | O | 0 |

-continued

| Radical | R₁ | R₂ | R₄ | R₃ | X₁ | p |
|---|---|---|---|---|---|---|
| A79 | CH₂ | 3-methoxy-2-methylenepyridine | H | CF₃ | O | 0 |
| A80 | CH₂ | 3-hydroxy-2-methylenepyridine | H | CF₃ | O | 0 |
| A81 | CH₂ | 2-methoxy-3-methylenepyridine | H | CF₃ | O | 0 |
| A82 | CH₂ | 2-hydroxy-3-methylenepyridine | H | CF₃ | O | 0 |
| A83 | CH₂ | 3-methoxy-4-methylenepyridine | H | CF₃ | O | 0 |
| A84 | CH₂ | 3-hydroxy-4-methylenepyridine | H | CF₃ | O | 0 |
| A85 | CH₂ | 3-methylene-4,5-dihydroisoxazole | H | CF₃ | O | 0 |
| A86 | CH₂ | 3-methyleneisoxazole | H | CF₃ | O | 0 |
| A87 | CH₂ | 4-fluoro-2-methoxy-benzyl | H | CF₃ | O | 0 |
| A88 | CH₂ | 4-ethoxy-3-methoxy-5-cyanobenzyl | H | CF₃ | O | 0 |

-continued

| Radical | R₁ | R₂ | R₄ | R₃ | X₁ | p |
|---|---|---|---|---|---|---|
| A89 | CH₂ | 2-(OCH₂CH₂)-C₆H₄-OCH₃ | H | CF₃ | O | 0 |
| A90 | CH₂ | 2-(O-CH₂)-C₆H₄-OCH₃ | H | CF₃ | O | 0 |
| A91 | CH₂CH₂ | CH₃ | H | CF₃ | O | 0 |
| A92 | CH₂CH₂ | CH₃CH₂ | H | CF₃ | O | 0 |
| A93 | CH₂CH₂ | (CH₃)₂CH | H | CF₃ | O | 0 |
| A94 | CH₂CH₂ | PhCH₂ | H | CF₃ | O | 0 |
| A95 | CH₂CH₂ | CH₃ | H | CF₃ | S | 0 |
| A96 | CH₂CH₂ | CH₃ | H | CF₃ | SO | 0 |
| A97 | CH₂CH₂ | CH₃ | H | CF₃ | SO₂ | 0 |
| A98 | CH₂CH₂ | (CH₃)₂CHCH₂ | H | CF₃ | O | |
| A99 | CH₂CH₂ | CH₃OCH₂ | H | CF₃ | O | 0 |
| A100 | CH₂CH₂ | CH₃CH₂OCH₂ | H | CF₃ | O | 0 |
| A101 | CH₂CH₂ | CH₃OCH₂CH₂ | H | CF₃ | O | 0 |
| A102 | CH₂CH₂ | CH₃CH₂OCH₂CH₂ | H | CF₃ | O | 0 |
| A103 | CH₂CH₂ | CH₃OC(CH₃)₂CH₂ | H | CF₃ | O | 0 |
| A104 | CH₂CH₂ | CH₃OCH(CH₃)CH₂ | H | CF₃ | O | 0 |
| A105 | CH₂CH₂ | CH₃OCH₂CH(CH₃) | H | CF₃ | O | 0 |
| A106 | CH₂CH₂ | CH₃OCH₂C(CH₃)₂ | H | CF₃ | O | 0 |
| A107 | CH₂CH₂ | CH₃OCH(CH₃) | H | CF₃ | O | 0 |
| A108 | CH₂CH₂ | CH₃OC(CH₃)₂ | H | CF₃ | O | 0 |
| A109 | CH₂CH₂ | HC≡CCH₂ | H | CF₃ | O | 0 |
| A110 | CH₂CH₂ | H₂C=CHCH₂ | H | CF₃ | O | 0 |
| A111 | CH₂CH₂ | CH₃C≡CCH₂ | H | CF₃ | O | 0 |
| A112 | CH₂CH₂ | cyclopropyl-CH | H | CF₃ | O | 0 |
| A113 | CH₂CH₂ | oxiranyl-CH | H | CF₃ | O | 0 |
| A114 | CH₂CH₂ | cyclobutyl-CH | H | CF₃ | O | 0 |
| A115 | CH₂CH₂ | oxetanyl-CH | H | CF₃ | O | 0 |
| A116 | CH₂CH₂ | cyclopentyl-CH | H | CF₃ | O | 0 |
| A117 | CH₂CH₂ | tetrahydrofuranyl-CH | H | CF₃ | O | 0 |
| A118 | CH₂CH₂ | cyclohexyl-CH | H | CF₃ | O | 0 |
| A119 | CH₂CH₂ | tetrahydropyranyl-CH | H | CF₃ | O | 0 |
| A120 | CH₂CH₂ | 1,4-dioxanyl-CH | H | CF₃ | O | 0 |

-continued
| Radical | R₁ | R₂ | R₄ | R₃ | X₁ | p |
|---|---|---|---|---|---|---|
| A121 | CH₂CH₂ | 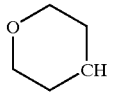 | H | CF₃ | O | 0 |
| A122 | CH₂CH₂ | 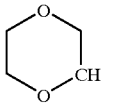 | H | CF₃ | O | 0 |
| A123 | CH₂CH₂ | 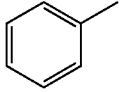 | H | CF₃ | O | 0 |
| A124 | CH₂CH₂ | 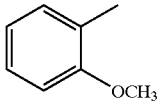 | H | CF₃ | O | 0 |
| A125 | CH₂CH₂ | 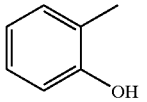 | H | CF₃ | O | 0 |
| A126 | CH₂CH₂ | 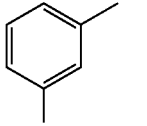 | H | CF₃ | O | 0 |
| A127 | CH₂CH₂ | 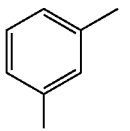 | H | CF₃ | O | 0 |
| A128 | CH₂CH₂ | 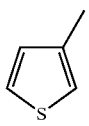 | H | CF₃ | O | 0 |
| A129 | CH₂CH₂ | 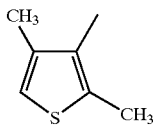 | H | CF₃ | O | 0 |
| A130 | CH₂CH₂ | 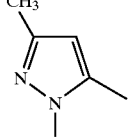 | H | CF₃ | O | 0 |
| A131 | CH₂CH₂ | 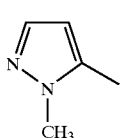 | H | CF₃ | O | 0 |

-continued

| Radical | R₁ | R₂ | R₄ | R₃ | X₁ | p |
|---|---|---|---|---|---|---|
| A132 | CH₂CH₂ | 2-pyridyl | H | CF₃ | O | 0 |
| A133 | CH₂CH₂ | 3-pyridyl | H | CF₃ | O | 0 |
| A134 | CH₂CH₂ | 4-pyridyl | H | CF₃ | O | 0 |
| A135 | CH₂CH₂ | 3-OCH₃-2-pyridyl | H | CF₃ | O | 0 |
| A136 | CH₂CH₂ | 3-OH-2-pyridyl | H | CF₃ | O | 0 |
| A137 | CH₂CH₂ | 2-OCH₃-3-pyridyl | H | CF₃ | O | 0 |
| A138 | CH₂CH₂ | 2-OH-3-pyridyl | H | CF₃ | O | 0 |
| A139 | CH₂CH₂ | 3-OCH₃-4-pyridyl | H | CF₃ | O | 0 |
| A140 | CH₂CH₂ | 3-OH-4-pyridyl | H | CF₃ | O | 0 |
| A141 | CH₂CH₂ | 4,5-dihydroisoxazol-3-yl | H | CF₃ | O | 0 |
| A142 | CH₂CH₂ | isoxazol-3-yl | H | CF₃ | O | 0 |

-continued
| Radical | R₁ | R₂ | R₄ | R₃ | X₁ | p |
|---|---|---|---|---|---|---|
| A143 | CH₂CH₂ | 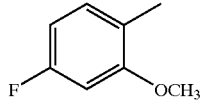 | H | CF₃ | O | 0 |
| A144 | CH₂CH₂ | 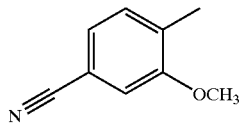 | H | CF₃ | O | 0 |
| A145 | CH₂CH₂ | 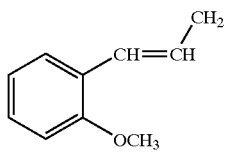 | H | CF₃ | O | 0 |
| A146 | CH₂CH₂ | 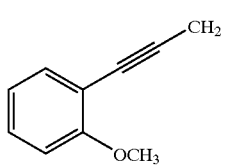 | H | CF₃ | O | 0 |
| A147 | CH₂CH₂ | 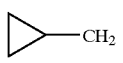 | H | CF₃ | O | 0 |
| A148 | CH₂CH₂ | 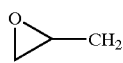 | H | CF₃ | O | 0 |
| A149 | CH₂CH₂ | 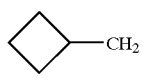 | H | CF₃ | O | 0 |
| A150 | CH₂CH₂ | 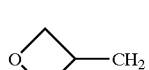 | H | CF₃ | O | 0 |
| A151 | CH₂CH₂ | 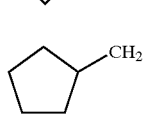 | H | CF₃ | O | 0 |
| A152 | CH₂CH₂ | 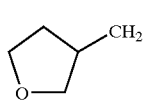 | H | CF₃ | O | 0 |
| A153 | CH₂CH₂ | 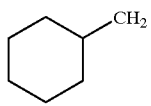 | H | CF₃ | O | 0 |
| A154 | CH₂CH₂ | 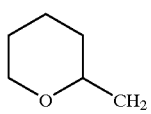 | H | CF₃ | O | 0 |
| A155 | CH₂CH₂ | 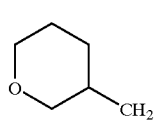 | H | CF₃ | O | 0 |

-continued

| Radical | R₁ | R₂ | R₄ | R₃ | X₁ | p |
|---|---|---|---|---|---|---|
| A156 | CH₂CH₂ | (tetrahydropyran-4-yl)CH₂ | H | CF₃ | O | 0 |
| A157 | CH₂CH₂ | (1,4-dioxan-2-yl)CH₂ | H | CF₃ | O | 0 |
| A158 | CH₂CH₂ | C₆H₅CH₂ | H | CF₃ | O | 0 |
| A159 | CH₂CH₂ | 2-(OCH₃)C₆H₄CH₂ | H | CF₃ | O | 0 |
| A160 | CH₂CH₂ | 2-(OH)C₆H₄CH₂ | H | CF₃ | O | 0 |
| A161 | CH₂CH₂ | 3-(OCH₃)C₆H₄CH₂ | H | CF₃ | O | 0 |
| A162 | CH₂CH₂ | 3-(OH)C₆H₄CH₂ | H | CF₃ | O | 0 |
| A163 | CH₂CH₂ | (thiophen-3-yl)CH₂ | H | CF₃ | O | 0 |
| A164 | CH₂CH₂ | 2,4-dimethyl-3-(OCH₂CH₃)thiophen-5-yl | H | CF₃ | O | 0 |
| A165 | CH₂CH₂ | 1,3-dimethyl-5-(OCH₂CH₃)pyrazol-4-yl | H | CF₃ | O | 0 |
| A166 | CH₂CH₂ | 1-methyl-5-(OCH₂CH₃)pyrazol-3-yl | H | CF₃ | O | 0 |

-continued
| Radical | R₁ | R₂ | R₄ | R₃ | X₁ | p |
|---|---|---|---|---|---|---|
| A167 | CH₂CH₂ | 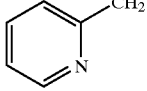 | H | CF₃ | O | 0 |
| A168 | CH₂CH₂ | 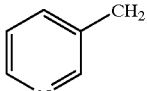 | H | CF₃ | O | 0 |
| A169 | CH₂CH₂ | 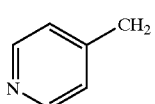 | H | CF₃ | O | 0 |
| A170 | CH₂CH₂ | 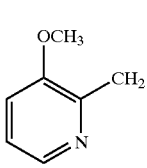 | H | CF₃ | O | 0 |
| A171 | CH₂CH₂ | 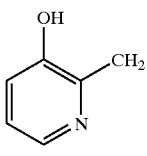 | H | CF₃ | O | 0 |
| A172 | CH₂CH₂ | 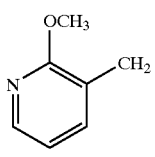 | H | CF₃ | O | 0 |
| A173 | CH₂CH₂ | 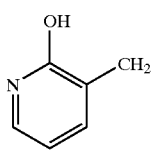 | H | CF₃ | O | 0 |
| A174 | CH₂CH₂ | 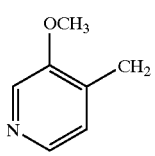 | H | CF₃ | O | 0 |
| A175 | CH₂CH₂ | 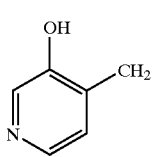 | H | CF₃ | O | 0 |
| A176 | CH₂CH₂ | 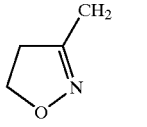 | H | CF₃ | O | 0 |
| A177 | CH₂CH₂ | 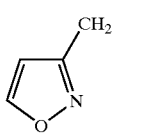 | H | CF₃ | O | 0 |

| Radical | R₁ | R₂ | R₄ | R₃ | X₁ | p |
|---|---|---|---|---|---|---|
| A178 | CH₂CH₂ | 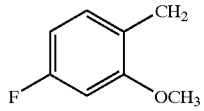 | H | CF₃ | O | 0 |
| A179 | CH₂CH₂ | 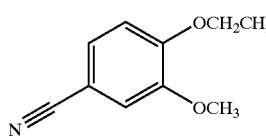 | H | CF₃ | O | 0 |
| A180 | CH₂CH₂ | 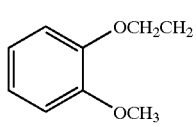 | H | CF₃ | O | 0 |
| A181 | CH₂CH₂ | 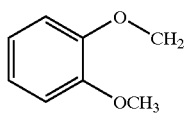 | H | CF₃ | O | 0 |
| A182 | CH(OCH₃)CH₂ | CH₃ | H | CF₃ | O | 0 |
| A183 | CH(OCH₃)CH₂ | CH₃CH₂ | H | CF₃ | O | 0 |
| A184 | CH(OCH₃)CH₂ | (CH₃)₂CH | H | CF₃ | O | 0 |
| A185 | CH(OCH₃)CH₂ | PhCH₂ | H | CF₃ | O | 0 |
| A186 | CH(OCH₃)CH₂ | CH₃ | H | CF₃ | S | 0 |
| A187 | CH(OCH₃)CH₂ | CH₃ | H | CF₃ | SO | 0 |
| A188 | CH(OCH₃)CH₂ | CH₃ | H | CF₃ | SO₂ | 0 |
| A189 | CH(OCH₃)CH₂ | CH₃CH₂CH₂ | H | CF₃ | O | 0 |
| A190 | CH(OCH₃)CH₂ | CH₃OCH₂ | H | CF₃ | O | 0 |
| A191 | CH(OCH₃)CH₂ | CH₃CH₂OCH₂ | H | CF₃ | O | 0 |
| A192 | CH(OCH₃)CH₂ | CH₃OCH₂CH₂ | H | CF₃ | O | 0 |
| A193 | CH(OCH₃)CH₂ | CH₃CH₂OCH₂CH₂ | H | CF₃ | O | 0 |
| A194 | CH(OCH₃)CH₂ | CH₃OC(CH₃)₂CH₂ | H | CF₃ | O | 0 |
| A195 | CH(OCH₃)CH₂ | CH₃OCH(CH₃)CH₂ | H | CF₃ | O | 0 |
| A196 | CH(OCH₃)CH₂ | CH₃OCH₂CH(CH₃) | H | CF₃ | O | 0 |
| A197 | CH(OCH₃)CH₂ | CH₃OCH₂C(CH₃)₂ | H | CF₃ | O | 0 |
| A198 | CH(OCH₃)CH₂ | CH₃OCH(CH₃) | H | CF₃ | O | 0 |
| A199 | CH(OCH₃)CH₂ | CH₃OC(CH₃)₂ | H | CF₃ | O | 0 |
| A200 | CH(OCH₃)CH₂ | HC≡CCH₂ | H | CF₃ | O | 0 |
| A201 | CH(OCH₃)CH₂ | H₂C=CHCH₂ | H | CF₃ | O | 0 |
| A202 | CH(OCH₃)CH₂ | CH₃C≡CCH₂ | H | CF₃ | O | 0 |
| A203 | CH(OCH₃)CH₂ |  | H | CF₃ | O | 0 |
| A204 | CH(OCH₃)CH₂ |  | H | CF₃ | O | 0 |
| A205 | CH(OCH₃)CH₂ |  | H | CF₃ | O | 0 |
| A206 | CH(OCH₃)CH₂ |  | H | CF₃ | O | 0 |
| A207 | CH(OCH₃)CH₂ |  | H | CF₃ | O | 0 |
| A208 | CH(OCH₃)CH₂ | 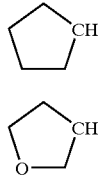 | H | CF₃ | O | 0 |

-continued
| Radical | R₁ | R₂ | R₄ | R₃ | X₁ | p |
|---------|-----|-----|-----|-----|-----|---|
| A209 | CH(OCH₃)CH₂ |  | H | CF₃ | O | 0 |
| A210 | CH(OCH₃)CH₂ |  | H | CF₃ | O | 0 |
| A211 | CH(OCH₃)CH₂ | 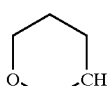 | H | CF₃ | O | 0 |
| A212 | CH(OCH₃)CH₂ | 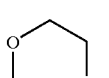 | H | CF₃ | O | 0 |
| A213 | CH(OCH₃)CH₂ | 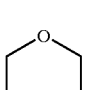 | H | CF₃ | O | 0 |
| A214 | CH(OCH₃)CH₂ | 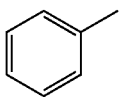 | H | CF₃ | O | 0 |
| A215 | CH(OCH₃)CH₂ | 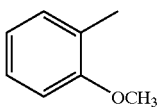 | H | CF₃ | O | 0 |
| A216 | CH(OCH₃)CH₂ | 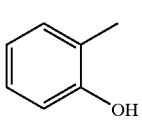 | H | CF₃ | O | 0 |
| A217 | CH(OCH₃)CH₂ | 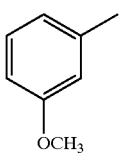 | H | CF₃ | O | 0 |
| A218 | CH(OCH₃)CH₂ | 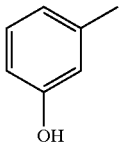 | H | CF₃ | O | 0 |
| A219 | CH(OCH₃)CH₂ | 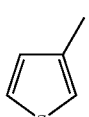 | H | CF₃ | O | 0 |
| A220 | CH(OCH₃)CH₂ | 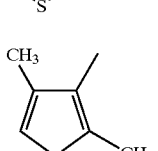 | H | CF₃ | O | 0 |

| Radical | R₁ | R₂ | R₄ | R₃ | X₁ | p |
|---|---|---|---|---|---|---|
| A221 | CH(OCH₃)CH₂ | 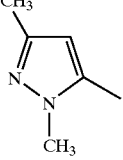 | H | CF₃ | O | 0 |
| A222 | CH(OCH₃)CH₂ | 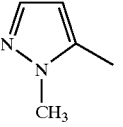 | H | CF₃ | O | 0 |
| A223 | CH(OCH₃)CH₂ | 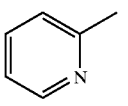 | H | CF₃ | O | 0 |
| A224 | CH(OCH₃)CH₂ | 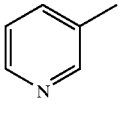 | H | CF₃ | O | 0 |
| A225 | CH(OCH₃)CH₂ | 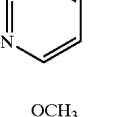 | H | CF₃ | O | 0 |
| A226 | CH(OCH₃)CH₂ | 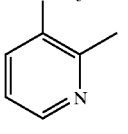 | H | CF₃ | O | 0 |
| A227 | CH(OCH₃)CH₂ | 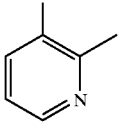 | H | CF₃ | O | 0 |
| A228 | CH(CCH₃)CH₂ | 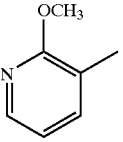 | H | CF₃ | O | 0 |
| A229 | CH(OCH₃)CH₂ | 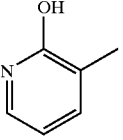 | H | CF₃ | O | 0 |
| A230 | CH(OCH₃)CH₂ | 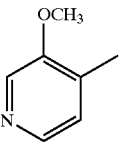 | H | CF₃ | O | 0 |

| Radical | R₁ | R₂ | R₄ | R₃ | X₁ | p |
|---|---|---|---|---|---|---|
| A231 | CH(OCH₃)CH₂ | 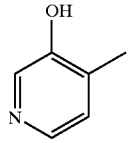 | H | CF₃ | O | 0 |
| A232 | CH(OCH₃)CH₂ | 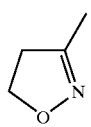 | H | CF₃ | O | 0 |
| A233 | CH(OCH₃)CH₂ | 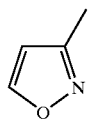 | H | CF₃ | O | 0 |
| A234 | CH(OCH₃)CH₂ | 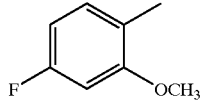 | H | CF₃ | O | 0 |
| A235 | CH(OCH₃)CH₂ | 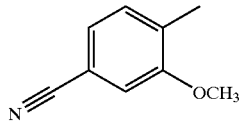 | H | CF₃ | O | 0 |
| A236 | CH(OCH₃)CH₂ | 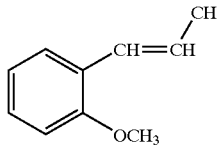 | H | CF₃ | O | 0 |
| A237 | CH(OCH₃)CH₂ | 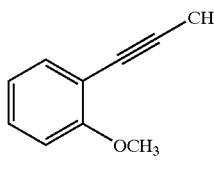 | H | CF₃ | O | 0 |
| A238 | CH(OCH₃)CH₂ | 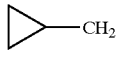 | H | CF₃ | O | 0 |
| A239 | CH(OCH₃)CH₂ | 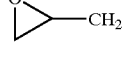 | H | CF₃ | O | 0 |
| A240 | CH(OCH₃)CH₂ | 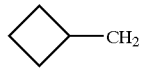 | H | CF₃ | O | 0 |
| A241 | CH(OCH₃)CH₂ | 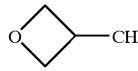 | H | CF₃ | O | 0 |
| A242 | CH(OCH₃)CH₂ | 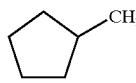 | H | CF₃ | O | 0 |
| A243 | CH(OCH₃)CH₂ | 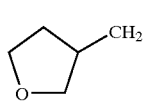 | H | CF₃ | O | 0 |

-continued

| Radical | R₁ | R₂ | R₄ | R₃ | X₁ | p |
|---|---|---|---|---|---|---|
| A244 | CH(OCH₃)CH₂ | cyclohexyl-CH₂ | H | CF₃ | O | 0 |
| A245 | CH(OCH₃)CH₂ | (tetrahydropyran-2-yl)-CH₂ | H | CF₃ | O | 0 |
| A246 | CH(OCH₃)CH₂ | (tetrahydropyran-3-yl)-CH₂ | H | CF₃ | O | 0 |
| A247 | CH(OCH₃)CH₂ | (tetrahydropyran-4-yl)-CH₂ | H | CF₃ | O | 0 |
| A248 | CH(OCH₃)CH₂ | (1,4-dioxan-2-yl)-CH₂ | H | CF₃ | O | 0 |
| A249 | CH(OCH₃)CH₂ | phenyl-CH₂ | H | CF₃ | O | 0 |
| A250 | CH(OCH₃)CH₂ | (2-methoxyphenyl)-CH₂ | H | CF₃ | O | 0 |
| A251 | CH(OCH₃)CH₂ | (2-hydroxyphenyl)-CH₂ | H | CF₃ | O | 0 |
| A252 | CH(OCH₃)CH₂ | (3-methoxyphenyl)-CH₂ | H | CF₃ | O | 0 |
| A253 | CH(OCH₃)CH₂ | (3-hydroxyphenyl)-CH₂ | H | CF₃ | O | 0 |
| A254 | CH(OCH₃)CH₂ | (thien-3-yl)-CH₂ | H | CF₃ | O | 0 |
| A255 | CH(OCH₃)CH₂ | (2,5-dimethyl-3-ethoxythien-4-yl)-CH₂ | H | CF₃ | O | 0 |

-continued

| Radical | R₁ | R₂ | R₄ | R₃ | X₁ | p |
|---|---|---|---|---|---|---|
| A256 | CH(OCH₃)CH₂ | 3-methyl-5-(OCH₂CH₂)-1-methyl-pyrazole | H | CF₃ | O | 0 |
| A257 | CH(OCH₃)CH₂ | 5-(OCH₂CH₂)-1-methyl-pyrazole | H | CF₃ | O | 0 |
| A258 | CH(OCH₃)CH₂ | 2-pyridyl-CH₂ | H | CF₃ | O | 0 |
| A259 | CH(OCH₃)CH₂ | 3-pyridyl-CH₂ | H | CF₃ | O | 0 |
| A260 | CH(OCH₃)CH₂ | 4-pyridyl-CH₂ | H | CF₃ | O | 0 |
| A261 | CH(OCH₃)CH₂ | 3-OCH₃-2-pyridyl-CH₂ | H | CF₃ | O | 0 |
| A262 | CH(OCH₃)CH₂ | 3-OH-2-pyridyl-CH₂ | H | CF₃ | O | 0 |
| A263 | CH(OCH₃)CH₂ | 2-OCH₃-3-pyridyl-CH₂ | H | CF₃ | O | 0 |
| A264 | CH(OCH₃)CH₂ | 2-OH-3-pyridazinyl-CH₂ | H | CF₃ | O | 0 |
| A265 | CH(OCH₃)CH₂ | 3-OCH₃-4-pyridyl-CH₂ | H | CF₃ | O | 0 |

-continued

| Radical | R₁ | R₂ | R₄ | R₃ | X₁ | p |
|---|---|---|---|---|---|---|
| A266 | CH(OCH₃)CH₂ | 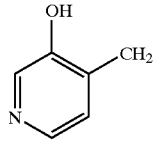 | H | CF₃ | O | 0 |
| A267 | CH(OCH₃)CH₂ | 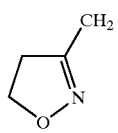 | H | CF₃ | O | 0 |
| A268 | CH(OCH₃)CH₂ | 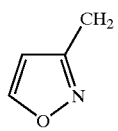 | H | CF₃ | O | 0 |
| A269 | CH(OCH₃)CH₂ | 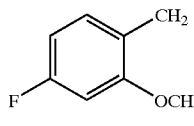 | H | CF₃ | O | 0 |
| A270 | CH(OCH₂)CH₂ | 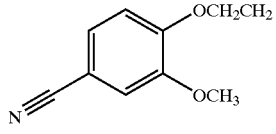 | H | CF₃ | O | 0 |
| A271 | CH(OCH₃)CH₂ | 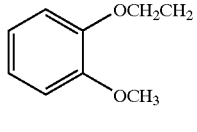 | H | CF₃ | O | 0 |
| A272 | CH(OCH₃)CH₂ | 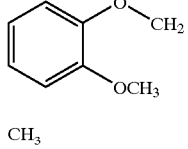 | H | CF₃ | O | 0 |
| A273 | CH₂CH(OCH₃)CH₂ | CH₃ | H | CF₃ | O | 0 |
| A274 | CH₂CH(OCH₃)CH₂ | CH₃CH₂ | H | CF₃ | O | 0 |
| A275 | CH₂CH(OCH₃)CH₂ | (CH₃)₂CH | H | CF₃ | O | 0 |
| A276 | CH₂CH(OCH₃)CH₂ | PhCH₂ | H | CF₃ | O | 0 |
| A277 | CH₂CH(OCH₃)CH₂ | CH₃ | H | CF₃ | S | 0 |
| A278 | CH₂CH(OCH₃)CH₂ | CH₃ | H | CF₃ | SO | 0 |
| A279 | CH₂CH(OCH₃)CH₂ | CH₃ | H | CF₃ | SO₂ | 0 |
| A280 | CH₂CH(OCH₃)CH₂ | CH₃CH₂CH₂ | H | CF₃ | O | 0 |
| A281 | CH₂CH(OCH₃)CH₂ | CH₃OCH₂ | H | CF₃ | O | 0 |
| A282 | CH₂CH(OCH₃)CH₂ | CH₃CH₂OCH₂ | H | CF₃ | O | 0 |
| A283 | CH₂CH(OCH₃)CH₂ | CH₃OCH₂CH₂ | H | CF₃ | O | 0 |
| A284 | CH₂CH(OCH₃)CH₂ | CH₃CH₂OCH₂CH₂ | H | CF₃ | O | 0 |
| A285 | CH₂CH(OCH₃)CH₂ | CH₃OC(CH₃)₂CH₂ | H | CF₃ | O | 0 |
| A286 | CH₂CH(OCH₃)CH₂ | CH₃OCH(CH₃)CH₂ | H | CF₃ | O | 0 |
| A287 | CH₂CH(OCH₃)CH₂ | CH₃OCH₂CH(CH₃) | H | CF₃ | O | 0 |
| A288 | CH₂CH(OCH₃)CH₂ | CH₃OCH₂C(CH₃)₂ | H | CF₃ | O | 0 |
| A289 | CH₂CH(OCH₃)CH₂ | CH₃OCH(CH₃) | H | CF₃ | O | 0 |
| A290 | CH₂CH(OCH₃)CH₂ | CH₃OC(CH₃)₂ | H | CF₃ | O | 0 |
| A291 | CH₂CH(OCH₃)CH₂ | HC≡CCH₂ | H | CF₃ | O | 0 |
| A292 | CH₂CH(OCH₃)CH₂ | H₂C=CHCH₂ | H | CF₃ | O | 0 |
| A293 | CH₂CH(OCH₃)CH₂ | CH₃CCCH₂ | H | CF₃ | O | 0 |
| A294 | CH₂CH(OCH₃)CH₂ |  | H | CF₃ | O | 0 |
| A295 | CH₂CH(OCH₃)CH₂ |  | H | CF₃ | O | 0 |

-continued

| Radical | R₁ | R₂ | R₄ | R₃ | X₁ | p |
|---|---|---|---|---|---|---|
| A296 | CH₂CH(OCH₃)CH₂ | cyclobutyl-CH | H | CF₃ | O | 0 |
| A297 | CH₂CH(OCH₃)CH₂ | oxetanyl-CH | H | CF₃ | O | 0 |
| A298 | CH₂CH(OCH₃)CH₂ | cyclopentyl-CH | H | CF₃ | O | 0 |
| A299 | CH₂CH(OCH₃)CH₂ | tetrahydrofuranyl-CH | H | CF₃ | O | 0 |
| A300 | CH₂CH(OCH₃)CH₂ | cyclohexyl-CH | H | CF₃ | O | 0 |
| A301 | CH₂CH(OCH₃)CH₂ | tetrahydropyranyl-CH (2-) | H | CF₃ | O | 0 |
| A302 | CH₂CH(OCH₃)CH₂ | tetrahydropyranyl-CH (3-) | H | CF₃ | O | 0 |
| A303 | CH₂CH(OCH₃)CH₂ | tetrahydropyranyl-CH (4-) | H | CF₃ | O | 0 |
| A304 | CH₂CH(OCH₃)CH₂ | 1,3-dioxanyl-CH | H | CF₃ | O | 0 |
| A305 | CH₂CH(OCH₃)CH₂ | phenyl | H | CF₃ | O | 0 |
| A306 | CH₂CH(OCH₃)CH₂ | 2-OCH₃-phenyl | H | CF₃ | O | 0 |
| A307 | CH₂CH(OCH₃)CH₂ | 2-OH-phenyl | H | CF₃ | O | 0 |
| A308 | CH₂CH(OCH₃)CH₂ | 3-OCH₃-phenyl | H | CF₃ | O | p |

-continued

| Radical | R₁ | R₂ | R₄ | R₃ | X₁ | p |
|---|---|---|---|---|---|---|
| A309 | CH₂CH(OCH₃)CH₂ | 3-hydroxyphenyl | H | CF₃ | O | |
| A310 | CH₂CH(OCH₃)CH₂ | 3-methylthiophene | H | CF₃ | O | 0 |
| A311 | CH₂CH(OCH₃)CH₂ | 2,3,4-trimethylthiophene | H | CF₃ | O | 0 |
| A312 | CH₂CH(OCH₃)CH₂ | 1,3,5-trimethylpyrazole | H | CF₃ | O | 0 |
| A313 | CH₂CH(OCH₃)CH₂ | 1,5-dimethylpyrazole | H | CF₃ | O | 0 |
| A314 | CH₂CH(OCH₃)CH₂ | 2-methylpyridine | H | CF₃ | O | 0 |
| A315 | CH₂CH(OCH₃)CH₂ | 3-methylpyridine | H | CF₃ | O | 0 |
| A316 | CH₂CH(OCH₃)CH₂ | 4-methylpyridine | H | CF₃ | O | 0 |
| A317 | CH₂CH(OCH₃)CH₂ | 3-methoxy-2-methylpyridine | H | CF₃ | O | 0 |
| A318 | CH₂CH(OCH₃)CH₂ | 3-hydroxy-2-methylpyridine | H | CF₃ | O | 0 |
| A319 | CH₂CH(OCH₃)CH₂ | 2-methoxy-3-methylpyridine | H | CF₃ | O | 0 |

| Radical | R₁ | R₂ | R₄ | R₃ | X₁ | p |
|---|---|---|---|---|---|---|
| A320 | CH₂CH(OCH₃)CH₂ | 3-methyl-2-hydroxypyridin-yl | H | CF₃ | O | 0 |
| A321 | CH₂CH(OCH₃)CH₂ | 4-methyl-3-methoxypyridin-yl | H | CF₃ | O | 0 |
| A222 | CH₂CH(OCH₃)CH₂ | 4-methyl-3-hydroxypyridin-yl | H | CF₃ | O | 0 |
| A323 | CH₂CH(OCH₃)CH₂ | 3-methyl-4,5-dihydroisoxazol-yl | H | CF₃ | O | 0 |
| A324 | CH₂CH(OCH₃)CH₂ | 3-methylisoxazol-yl | H | CF₃ | O | 0 |
| A325 | CH₂CH(OCH₃)CH₂ | 4-fluoro-2-methoxy-1-methylphenyl | H | CF₃ | O | 0 |
| A326 | CH₂CH(OCH₃)CH₂ | 4-cyano-2-methoxy-1-methylphenyl | H | CF₃ | O | 0 |
| A327 | CH₂CH(OCH₃)CH₂ | (2-methoxyphenyl)CH=CH-CH₂ | H | CF₃ | O | 0 |
| A328 | CH₂CH(OCH₃)CH₂ | (2-methoxyphenyl)C≡C-CH₂ | H | CF₃ | O | 0 |
| A329 | CH₂CH(OCH₃)CH₂ | cyclopropyl-CH₂ | H | CF₃ | O | 0 |
| A330 | CH₂CH(OCH₃)CH₂ | oxiranyl-CH₂ | H | CF₃ | O | 0 |
| A331 | CH₂CH(OCH₃)CH₂ | cyclobutyl-CH₂ | H | CF₃ | O | 0 |

-continued
| Radical | R₁ | R₂ | R₄ | R₃ | X₁ | p |
|---|---|---|---|---|---|---|
| A332 | CH₂CH(OCH₃)CH₂ | 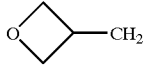 | H | CF₃ | O | 0 |
| A333 | CH₂CH(OCH₃)CH₂ |  | H | CF₃ | O | 0 |
| A334 | CH₂CH(OCH₃)CH₂ |  | H | CF₃ | O | 0 |
| A335 | CH₂CH(OCH₃)CH₂ | 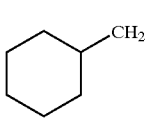 | H | CF₃ | O | 0 |
| A336 | CH₂CH(OCH₃)CH₂ | 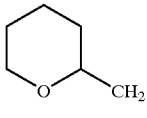 | H | CF₃ | O | 0 |
| A337 | CH₂CH(OCH₃)CH₂ | 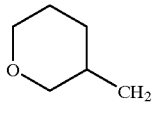 | H | CF₃ | O | 0 |
| A338 | CH₂CH(OCH₃)CH₂ | 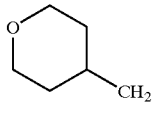 | H | CF₃ | O | 0 |
| A339 | CH₂CH(OCH₃)CH₂ | 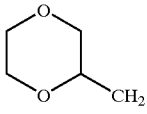 | H | CF₃ | O | 0 |
| A340 | CH₂CH(OCH₃)CH₂ | 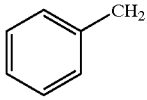 | H | CF₃ | O | 0 |
| A341 | CH₂CH(OCH₃)CH₂ | 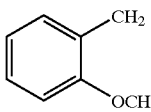 | H | CF₃ | O | 0 |
| A342 | CH₂CH(OCH₃)CH₂ | 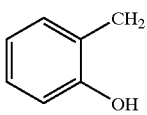 | H | CF₃ | O | 0 |
| A343 | CH₂CH(OCH₃)CH₂ | 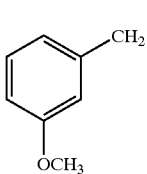 | H | CF₃ | O | 0 |

| Radical | R₁ | R₂ | R₄ | R₃ | X₁ | p |
|---|---|---|---|---|---|---|
| A344 | CH₂CH(OCH₃)CH₂ | 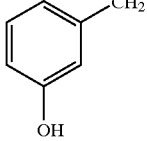 3-hydroxybenzyl | H | CF₃ | O | 0 |
| A345 | CH₂CH(OCH₃)CH₂ | 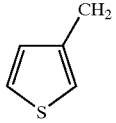 thiophen-3-ylmethyl | H | CF₃ | O | 0 |
| A346 | CH₂CH(OCH₃)CH₂ | 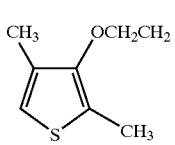 | H | CF₃ | O | 0 |
| A347 | CH₂CH(OCH₃)CH₂ | 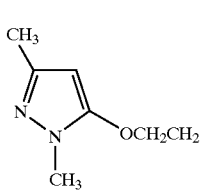 | H | CF₃ | O | 0 |
| A348 | CH₂CH(OCH₃)CH₂ | 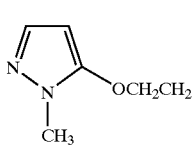 | H | CF₃ | O | 0 |
| A349 | CH₂CH(OCH₃)CH₂ | 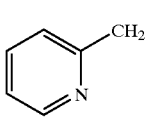 pyridin-2-ylmethyl | H | CF₃ | O | 0 |
| A350 | CH₂CH(OCH₃)CH₂ | 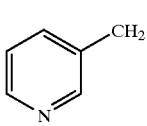 pyridin-3-ylmethyl | H | CF₃ | O | 0 |
| A351 | CH₂CH(OCH₃)CH₂ | 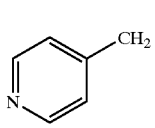 pyridin-4-ylmethyl | H | CF₃ | O | 0 |
| A352 | CH₂CH(OCH₃)CH₂ | 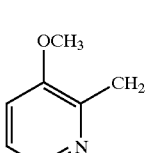 | H | CF₃ | O | 0 |
| A353 | CH₂CH(OCH₃)CH₂ | 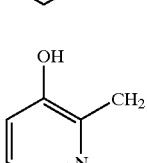 | H | CF₃ | O | 0 |

-continued

| Radical | R₁ | R₂ | R₄ | R₃ | X₁ | p |
|---|---|---|---|---|---|---|
| A354 | CH₂CH(OCH₃)CH₂ | 3-methyl-2-methoxypyridinyl-CH₂ | H | CF₃ | O | 0 |
| A355 | CH₂CH(OCH₃)CH₂ | 3-methyl-2-hydroxypyridinyl-CH₂ | H | CF₃ | O | 0 |
| A356 | CH₂CH(OCH₃)CH₂ | 3-methoxy-4-methylpyridinyl-CH₂ | H | CF₃ | O | 0 |
| A357 | CH₂CH(OCH₃)CH₂ | 3-hydroxy-4-methylpyridinyl-CH₂ | H | CF₃ | O | 0 |
| A358 | CH₂CH(OCH₃)CH₂ | 4,5-dihydroisoxazol-3-yl-CH₂ | H | CF₃ | O | 0 |
| A359 | CH₂CH(OCH₃)CH₂ | isoxazol-3-yl-CH₂ | H | CF₃ | O | 0 |
| A360 | CH₂CH(OCH₃)CH₂ | 4-fluoro-2-methoxybenzyl | H | CF₃ | O | 0 |
| A361 | CH₂CH(OCH₃)CH₂ | 3-methoxy-4-(cyanophenyl)-OCH₂CH₂ | H | CF₃ | O | 0 |
| A362 | CH₂CH(OCH₃)CH₂ | 2-methoxyphenyl-OCH₂CH₂ | H | CF₃ | O | 0 |
| A363 | CH₂CH(OCH₃)CH₂ | 2-methoxyphenyl-O-CH₂ | H | CF₃ | O | 0 |
| A364 | CH=CHCH₂ | CH₃ | H | CF₃ | O | 0 |
| A365 | CH=CHCH₂ | CH₃CH₂ | H | CF₃ | O | 0 |
| A366 | CH=CHCH₂ | (CH₃)₂CH | H | CF₃ | O | 0 |
| A367 | CH=CHCH₂ | PhCH₂ | H | CF₃ | O | 0 |
| A368 | CH=CHCH₂ | CH₃ | H | CF₃ | S | 0 |
| A369 | CH=CHCH₂ | CH₃ | H | CF₃ | SO | 0 |

-continued

| Radical | R₁ | R₂ | R₄ | R₃ | X₁ | p |
|---|---|---|---|---|---|---|
| A370 | CH=CHCH₂ | CH₃ | H | CF₃ | SO₂ | 0 |
| A371 | CH=CHCH₂ | CH₃CH₂CH₂ | H | CF₃ | O | 0 |
| A372 | CH=CHCH₂ | CH₃OCH₂ | H | CF₃ | O | 0 |
| A373 | CH=CHCH₂ | CH₃CH₂OCH₂ | H | CF₃ | O | 0 |
| A374 | CH=CHCH₂ | CH₃OCH₂CH₂ | H | CF₃ | O | 0 |
| A375 | CH=CHCH₂ | CH₃CH₂OCH₂CH₂ | H | CF₃ | O | 0 |
| A376 | CH=CHCH₂ | CH₃OC(CH₃)₂CH₂ | H | CF₃ | O | 0 |
| A377 | CH=CHCH₂ | CH₃OCH(CH₃)CH₂ | H | CF₃ | O | 0 |
| A378 | CH=CHCH₂ | CH₃OCH₂CH(CH₃) | H | CF₃ | O | 0 |
| A379 | CH=CHCH₂ | CH₃OCH₂C(CH₃)₂ | H | CF₃ | O | 0 |
| A380 | CH=CHCH₂ | CH₃OCH(CH₃) | H | CF₃ | O | 0 |
| A381 | CH=CHCH₂ | CH₃OC(CH₃)₂ | H | CF₃ | O | 0 |
| A382 | CH=CHCH₂ | HC≡CCH₂ | H | CF₃ | O | 0 |
| A383 | CH=CHCH₂ | H₂C=CHCH₂ | H | CF₃ | O | 0 |
| A384 | CH=CHCH₂ | CH₃C≡CCH₂ | H | CF₃ | O | 0 |
| A385 | CH=CHCH₂ |  | H | CF₃ | O | 0 |
| A386 | CH=CHCH₂ |  | H | CF₃ | O | 0 |
| A387 | CH=CHCH₂ |  | H | CF₃ | O | 0 |
| A388 | CH=CHCH₂ |  | H | CF₃ | O | 0 |
| A389 | CH=CHCH₂ |  | H | CF₃ | O | 0 |
| A390 | CH=CHCH₂ |  | H | CF₃ | O | 0 |
| A391 | CH=CHCH₂ |  | H | CF₃ | O | 0 |
| A392 | CH=CHCH₂ |  | H | CF₃ | O | 0 |
| A393 | CH=CHCH₂ |  | H | CF₃ | O | 0 |
| A394 | CH=CHCH₂ |  | H | CF₃ | O | 0 |
| A395 | CH=CHCH₂ |  | H | CF₃ | O | 0 |
| A396 | CH=CHCH₂ |  | H | CF₃ | O | 0 |

-continued
| Radical | R₁ | R₂ | R₄ | R₃ | X₁ | p |
|---|---|---|---|---|---|---|
| A397 | CH=CH₂ | 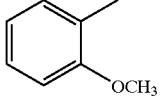 | H | CF₃ | O | 0 |
| A398 | CH=CH₂ | 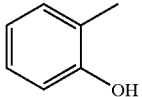 | H | CF₃ | O | 0 |
| A399 | CH=CH₂ | 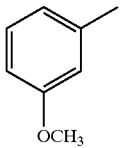 | H | CF₃ | O | 0 |
| A400 | CH=CH₂ | 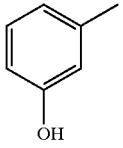 | H | CF₃ | O | 0 |
| A401 | CH=CH₂ | 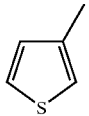 | H | CF₃ | O | 0 |
| A402 | CH=CH₂ | 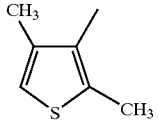 | H | CF₃ | O | 0 |
| A403 | CH=CH₂ | 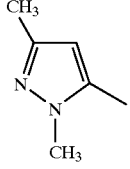 | H | CF₃ | O | 0 |
| A404 | CH=CH₂ | 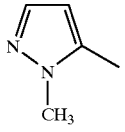 | H | CF₃ | O | 0 |
| A405 | CH=CH₂ | 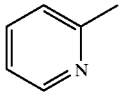 | H | CF₃ | O | 0 |
| A406 | CH=CH₂ | 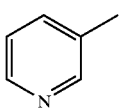 | H | CF₃ | O | 0 |
| A407 | CH=CH₂ | 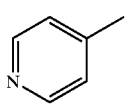 | H | CF₃ | O | 0 |

-continued

| Radical | R₁ | R₂ | R₄ | R₃ | X₁ | p |
|---------|-----|-----|-----|-----|-----|---|
| A408 | CH=CHCH₂ | 3-methoxy-2-methylpyridine | H | CF₃ | O | 0 |
| A409 | CH=CHCH₂ | 3-hydroxy-2-methylpyridine | H | CF₃ | O | 0 |
| A410 | CH=CHCH₂ | 2-methoxy-3-methylpyridine | H | CF₃ | O | 0 |
| A411 | CH=CHCH₂ | 2-hydroxy-3-methylpyridine | H | CF₃ | O | 0 |
| A412 | CH=CHCH₂ | 3-methoxy-4-methylpyridine | H | CF₃ | O | 0 |
| A413 | CH=CHCH₂ | 3-hydroxy-4-methylpyridine | H | CF₃ | O | 0 |
| A414 | CH=CHCH₂ | 3-methyl-4,5-dihydroisoxazole | H | CF₃ | O | 0 |
| A415 | CH=CHCH₂ | 3-methylisoxazole | H | CF₃ | O | 0 |
| A416 | CH=CHCH₂ | 5-fluoro-2-methyl-3-methoxyphenyl | H | CF₃ | O | 0 |
| A417 | CH=CHCH₂ | 4-methyl-3-methoxybenzonitrile | H | CF₃ | O | 0 |

-continued
| Radical | R₁ | R₂ | R₄ | R₃ | X₁ | p |
|---|---|---|---|---|---|---|
| A418 | CH=CH₂ | 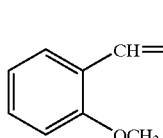 | H | CF₃ | O | 0 |
| A419 | CH=CH₂ | 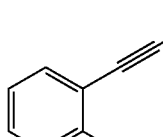 | H | CF₃ | O | 0 |
| A420 | CH=CH₂ |  | H | CF₃ | O | 0 |
| A421 | CH=CH₂ | 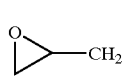 | H | CF₃ | O | 0 |
| A422 | CH=CH₂ | 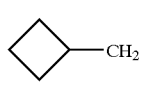 | H | CF₃ | O | 0 |
| A423 | CH=CH₂ | 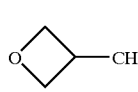 | H | CF₃ | O | 0 |
| A424 | CH=CH₂ | 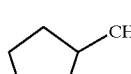 | H | CF₃ | O | 0 |
| A425 | CH=CH₂ | 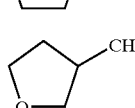 | H | CF₃ | O | 0 |
| A426 | CH=CH₂ | 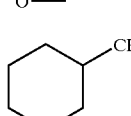 | H | CF₃ | O | 0 |
| A427 | CH=CH₂ | 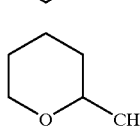 | H | CF₃ | O | 0 |
| A428 | CH=CH₂ | 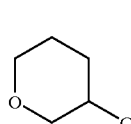 | H | CF₃ | O | 0 |
| A429 | CH=CH₂ | 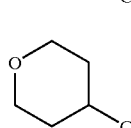 | H | CF₃ | O | 0 |
| A430 | CH=CH₂ | 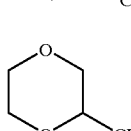 | H | CF₃ | O | 0 |
| A431 | CH=CH₂ | 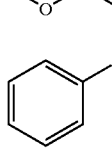 | H | CF₃ | O | 0 |

-continued
| Radical | R₁ | R₂ | R₄ | R₃ | X₁ | p |
|---|---|---|---|---|---|---|
| A432 | CH=CH₂ | 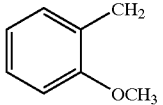 | H | CF₃ | O | 0 |
| A433 | CH=CH₂ | 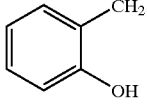 | H | CF₃ | O | 0 |
| A434 | CH=CH₂ | 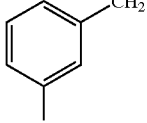 | H | CF₃ | O | 0 |
| A435 | CH=CH₂ | 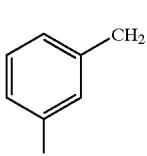 | H | CF₃ | O | 0 |
| A436 | CH=CH₂ | 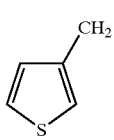 | H | CF₃ | O | 0 |
| A437 | CH=CH₂ |  | H | CF₃ | O | 0 |
| A438 | CH=CH₂ | 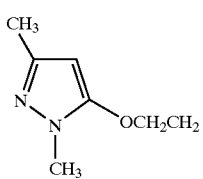 | H | CF₃ | O | 0 |
| A439 | CH=CH₂ | 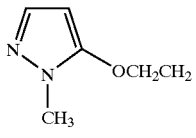 | H | CF₃ | O | 0 |
| A440 | CH=CH₂ | 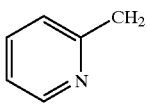 | H | CF₃ | O | 0 |
| A441 | CH=CH₂ | 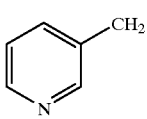 | H | CF₃ | O | 0 |
| A442 | CH=CH₂ | 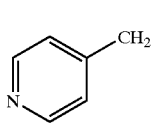 | H | CF₃ | O | 0 |

-continued

| Radical | R₁ | R₂ | R₄ | R₃ | X₁ | p |
|---|---|---|---|---|---|---|
| A443 | CH=CH₂ | 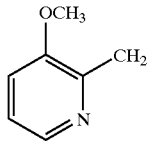 3-methoxy-2-pyridyl-CH₂ | H | CF₃ | O | 0 |
| A444 | CH=CH₂ | 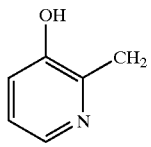 3-hydroxy-2-pyridyl-CH₂ | H | CF₃ | O | 0 |
| A445 | CH=CH₂ | 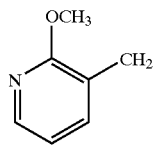 2-methoxy-3-pyridyl-CH₂ | H | CF₃ | O | 0 |
| A446 | CH=CH₂ | 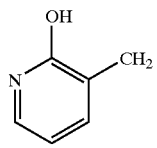 2-hydroxy-3-pyridyl-CH₂ | H | CF₃ | O | 0 |
| A447 | CH=CH₂ | 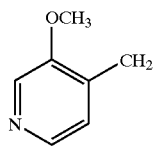 3-methoxy-4-pyridyl-CH₂ | H | CF₃ | O | 0 |
| A448 | CH=CH₂ | 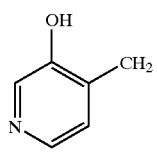 3-hydroxy-4-pyridyl-CH₂ | H | CF₃ | O | 0 |
| A449 | CH=CH₂ | 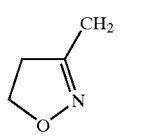 4,5-dihydroisoxazol-3-yl-CH₂ | H | CF₃ | O | 0 |
| A450 | CH=CH₂ | 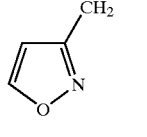 isoxazol-3-yl-CH₂ | H | CF₃ | O | 0 |
| A451 | CH=CH₂ | 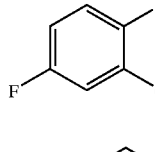 4-fluoro-2-methoxyphenyl-CH₂ | H | CF₃ | O | 0 |
| A452 | CH=CH₂ | 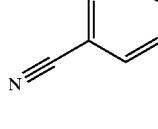 4-(2-cyanoethoxy)-3-methoxyphenyl | H | CF₃ | O | 0 |

-continued

| Radical | R₁ | R₂ | R₄ | R₃ | X₁ | p |
|---|---|---|---|---|---|---|
| A453 | CH=CHCH₂ | 2-OCH₃-phenyl-OCH₂CH₂ | H | CF₃ | O | 0 |
| A454 | CH=CHCH₂ | 2-OCH₃-phenyl-O-CH₂ | H | CF₃ | O | 0 |
| A455 | C≡CCH₂ | CH₃ | H | CF₃ | O | 0 |
| A456 | C≡CCH₂ | CH₃CH₂ | H | CF₃ | O | 0 |
| A457 | C≡CCH₂ | (CH₃)₂CH | H | CF₃ | O | 0 |
| A458 | C≡CCH₂ | PhCH₂ | H | CF₃ | O | 0 |
| A459 | C≡CCH₂ | CH₃ | H | CF₃ | S | 0 |
| A460 | C≡CCH₂ | CH₃ | H | CF₃ | SO | 0 |
| A461 | C≡CCH₂ | CH₃ | H | CF₃ | SO₂ | 0 |
| A462 | C≡CCH₂ | CH₃CH₂CH₂ | H | CF₃ | O | 0 |
| A463 | C≡CCH₂ | CH₃OCH₂ | H | CF₃ | O | 0 |
| A464 | C≡CCH₂ | CH₃CH₂OCH₂ | H | CF₃ | O | 0 |
| A465 | C≡CCH₂ | CH₃OCH₂CH₂ | H | CF₃ | O | 0 |
| A466 | C≡CCH₂ | CH₃CH₂OCH₂CH₂ | H | CF₃ | O | 0 |
| A467 | C≡CCH₂ | CH₃OC(CH₃)₂CH₂ | H | CF₃ | O | 0 |
| A468 | C≡CCH₂ | CH₃OCH(CH₃)CH₂ | H | CF₃ | O | 0 |
| A469 | C≡CCH₂ | CH₃OCH₂CH(CH₃) | H | CF₃ | O | 0 |
| A470 | C≡CCH₂ | CH₃OCH₂C(CH₃)₂ | H | CF₃ | O | 0 |
| A471 | C≡CCH₂ | CH₃OCH(CH₃) | H | CF₃ | O | 0 |
| A472 | C≡CCH₂ | CH₃OC(CH₃)₂ | H | CF₃ | O | 0 |
| A473 | C≡CCH₂ | HC≡CCH₂ | H | CF₃ | O | 0 |
| A474 | C≡CCH₂ | H₂C=CHCH₂ | H | CF₃ | O | 0 |
| A475 | C≡C-GH2 | CH₃C≡CCH₂ | H | CF₃ | O | 0 |
| A476 | C≡C-CH₂ | cyclopropyl-CH | H | CF₃ | O | 0 |
| A477 | C≡CCH₂ | oxiranyl-CH | H | CF₃ | O | 0 |
| A478 | C≡CCH₂ | cyclobutyl-CH | H | CF₃ | O | 0 |
| A479 | C≡CCH₂ | oxetanyl-CH | H | CF₃ | O | 0 |
| A480 | C≡CCH₂ | cyclopentyl-CH | H | CF₃ | O | 0 |
| A481 | C≡CCH₂ | tetrahydrofuranyl-CH | H | CF₃ | O | 0 |
| A482 | C≡CCH₂ | cyclohexyl-CH | H | CF₃ | O | 0 |
| A483 | C≡CCH₂ | tetrahydropyranyl-CH | H | CF₃ | O | 0 |
| A484 | C≡CCH₂ | 1,3-dioxanyl-CH | H | CF₃ | O | 0 |

-continued
| Radical | R₁ | R₂ | R₄ | R₃ | X₁ | p |
|---|---|---|---|---|---|---|
| A485 | C≡CH₂ | 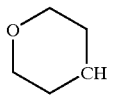 | H | CF₃ | O | 0 |
| A486 | C≡CH₂ | 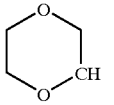 | H | CF₃ | O | 0 |
| A487 | C≡CH₂ | 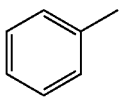 | H | CF₃ | O | 0 |
| A488 | C≡CH₂ | 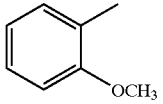 | H | CF₃ | O | 0 |
| A489 | C≡CH₂ | 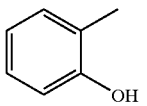 | H | CF₃ | O | 0 |
| A490 | C≡CH₂ | 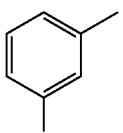 | H | CF₃ | O | 0 |
| A491 | C≡CH₂ | 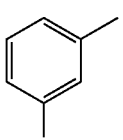 | H | CF₃ | O | 0 |
| A492 | C≡CH₂ | 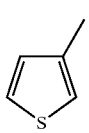 | H | CF₃ | O | 0 |
| A493 | C≡CH₂ | 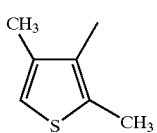 | H | CF₃ | O | 0 |
| A494 | C≡CH₂ | 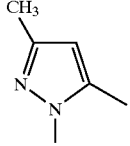 | H | CF₃ | O | 0 |
| A495 | C≡CH₂ | 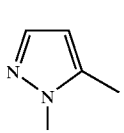 | H | CF₃ | O | 0 |

-continued
| Radical | R₁ | R₂ | R₄ | R₃ | X₁ | p |
|---|---|---|---|---|---|---|
| A496 | C≡CH₂ | 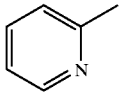 | H | CF₃ | O | 0 |
| A497 | C≡CH₂ | 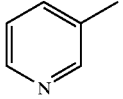 | H | CF₃ | O | 0 |
| A498 | C≡CH₂ | 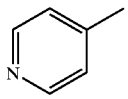 | H | CF₃ | O | 0 |
| A499 | C≡CH₂ | 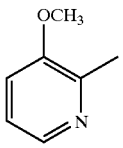 | H | CF₃ | O | 0 |
| A500 | C≡CH₂ | 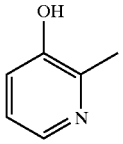 | H | CF₃ | O | 0 |
| A501 | C≡CH₂ | 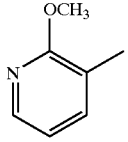 | H | CF₃ | O | 0 |
| A502 | C≡CH₂ | 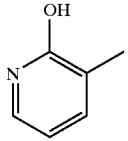 | H | CF₃ | O | 0 |
| A503 | C≡CH₂ | 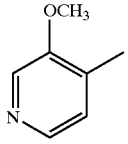 | H | CF₃ | O | 0 |
| A504 | C≡CH₂ | 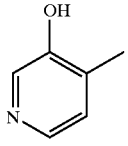 | H | CF₃ | O | 0 |
| A505 | C≡CH₂ | 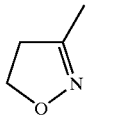 | H | CF₃ | O | 0 |
| A506 | C≡CH₂ | 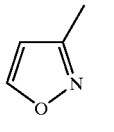 | H | CF₃ | O | 0 |

-continued

| Radical | R₁ | R₂ | R₄ | R₃ | X₁ | p |
|---|---|---|---|---|---|---|
| A507 | C≡CH₂ | 4-methyl-2-methoxy-5-fluorophenyl | H | CF₃ | O | 0 |
| A508 | C≡CH₂ | 4-methyl-3-methoxy-5-cyanophenyl | H | CF₃ | O | 0 |
| A509 | C≡CH₂ | 2-(2-methoxyphenyl)allyl (CH=CH-CH₂ on 2-OCH₃ phenyl) | H | CF₃ | O | 0 |
| A510 | C≡CH₂ | 2-(2-methoxyphenyl)propargyl (C≡C-CH₂ on 2-OCH₃ phenyl) | H | CF₃ | O | 0 |
| A511 | C≡CH₂ | cyclopropyl-CH₂ | H | CF₃ | O | 0 |
| A512 | C≡CH₂ | oxiranyl-CH₂ | H | CF₃ | O | 0 |
| A513 | C≡CH₂ | cyclobutyl-CH₂ | H | CF₃ | O | 0 |
| A514 | C≡CH₂ | oxetanyl-CH₂ | H | CF₃ | O | 0 |
| A515 | C≡CH₂ | cyclopentyl-CH₂ | H | CF₃ | O | 0 |
| A516 | C≡CH₂ | tetrahydrofuran-3-yl-CH₂ | H | CF₃ | O | 0 |
| A517 | C≡CH₂ | cyclohexyl-CH₂ | H | CF₃ | O | 0 |
| A518 | C≡CH₂ | tetrahydropyran-2-yl-CH₂ | H | CF₃ | O | 0 |
| A519 | C≡CH₂ | tetrahydropyran-3-yl-CH₂ | H | CF₃ | O | 0 |

-continued
| Radical | R₁ | R₂ | R₄ | R₃ | X₁ | p |
|---|---|---|---|---|---|---|
| A520 | C≡CCH₂ | 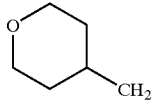 | H | CF₃ | O | 0 |
| A521 | C≡CCH₂ | 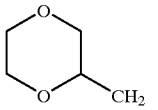 | H | CF₃ | O | 0 |
| A522 | C≡CCH₂ | 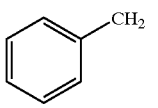 | H | CF₃ | O | 0 |
| A523 | C≡CCH₂ | 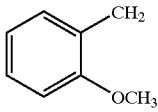 | H | CF₃ | O | 0 |
| A524 | C≡CCH₂ | 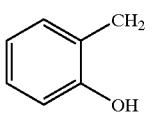 | H | CF₃ | O | 0 |
| A525 | C≡CCH₂ | 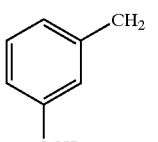 | H | CF₃ | O | 0 |
| A526 | C≡CCH₂ | 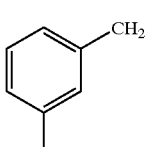 | H | CF₃ | O | 0 |
| A527 | C≡CCH₂ | 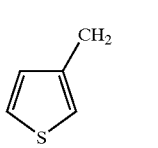 | H | CF₃ | O | 0 |
| A528 | C≡CCH₂ | 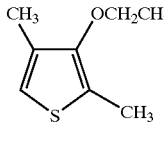 | H | CF₃ | O | 0 |
| A529 | C≡CCH₂ | 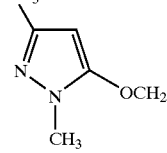 | H | CF₃ | O | 0 |
| A530 | C≡CCH₂ | 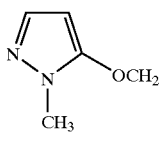 | H | CF₃ | O | 0 |

-continued
| Radical | R₁ | R₂ | R₄ | R₃ | X₁ | p |
|---|---|---|---|---|---|---|
| A531 | C≡CH₂ | 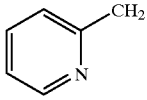 2-pyridyl-CH₂ | H | CF₃ | O | 0 |
| A532 | C≡CH₂ | 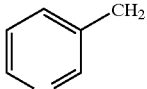 3-pyridyl-CH₂ | H | CF₃ | O | 0 |
| A533 | C≡CH₂ | 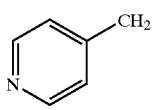 4-pyridyl-CH₂ | H | CF₃ | O | 0 |
| A534 | C≡CH₂ | 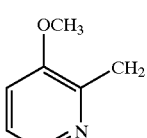 3-OCH₃-2-pyridyl-CH₂ | H | CF₃ | O | 0 |
| A535 | C≡CH₂ | 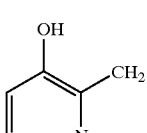 3-OH-2-pyridyl-CH₂ | H | CF₃ | O | 0 |
| A536 | C≡CH₂ | 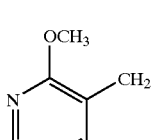 2-OCH₃-3-pyridyl-CH₂ | H | CF₃ | O | 0 |
| A537 | C≡CH₂ | 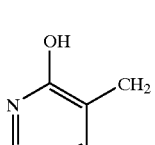 2-OH-3-pyridyl-CH₂ | H | CF₃ | O | 0 |
| A538 | C≡CH₂ | 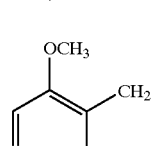 3-OCH₃-4-pyridyl-CH₂ | H | CF₃ | O | 0 |
| A539 | C≡CH₂ | 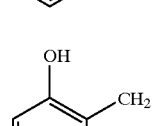 3-OH-4-pyridyl-CH₂ | H | CF₃ | O | 0 |
| A540 | C≡CH₂ | 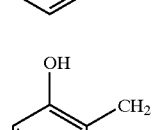 3-OH-4-pyridyl-CH₂ | H | CF₃ | O | 0 |

-continued

| Radical | R₁ | R₂ | R₄ | R₃ | X₁ | p |
|---|---|---|---|---|---|---|
| A541 | C≡CH₂ | 3-methyl-4,5-dihydroisoxazol-5-yl-CH₂ | H | CF₃ | O | 0 |
| A542 | C≡CH₂ | (4-fluoro-2-methoxyphenyl)-CH₂ | H | CF₃ | O | 0 |
| A543 | C≡CH₂ | (4-ethoxy-3-methoxy-cyanophenyl)-CH₂ (with OCH₂CH₂, OCH₃, CN substituents) | H | CF₃ | O | 0 |
| A544 | C≡CH₂ | (2-methoxyphenyl)-OCH₂CH₂ | H | CF₃ | O | 0 |
| A545 | C≡CH₂ | (2-methoxyphenoxy)-CH₂ | H | CF₃ | O | 0 |
| A546 | CH₂ | CH₃ | H | CF₂Cl | O | 0 |
| A547 | CH₂ | CH₃CH₂ | H | CF₂Cl | O | 0 |
| A548 | CH₂ | (CH₃)₂CH | H | CF₂Cl | O | 0 |
| A549 | CH₂ | PhCH₂ | H | CF₂Cl | O | 0 |
| A550 | CH₂ | CH₃ | H | CF₂Cl | S | 0 |
| A551 | CH₂ | CH₃ | H | CF₂Cl | SO | 0 |
| A552 | CH₂ | CH₃ | H | CF₂Cl | SO₂ | 0 |
| A553 | CH₂ | CH₃CH₂CH₂ | H | CF₂Cl | O | 0 |
| A554 | CH₂ | CH₃OCH₂ | H | CF₂Cl | O | 0 |
| A555 | CH₂ | CH₃CH₂OCH₂ | H | CF₂Cl | O | 0 |
| A556 | CH₂ | CH₃OCH₂CH₂ | H | CF₂Cl | O | 0 |
| A557 | CH₂ | CH₃CH₂OCH₂CH₂ | H | CF₂Cl | O | 0 |
| A558 | CH₂ | CH₃OC(CH₃)₂CH₂ | H | CF₂Cl | O | 0 |
| A559 | CH₂ | CH₃OCH(CH₃)CH₂ | H | CF₂Cl | O | 0 |
| A560 | CH₂ | CH₃OCH₂CH(CH₃) | H | CF₂Cl | O | 0 |
| A561 | CH₂ | CH₃OCH₂C(CH₃)₂ | H | CF₂Cl | O | 0 |
| A562 | CH₂ | CH₃OCH(CH₃) | H | CF₂Cl | O | 0 |
| A563 | CH₂ | CH₃OC(CH₃)₂ | H | CF₂Cl | O | 0 |
| A564 | CH₂ | HC≡CCH₂ | H | CF₂Cl | O | 0 |
| A565 | CH₂ | H₂C=CHCH₂ | H | CF₂Cl | O | 0 |
| A566 | CH₂ | CH₃C≡CCH₂ | H | CF₂Cl | O | 0 |
| A567 | CH₂ | cyclopropyl-CH | H | CF₂Cl | O | 0 |
| A568 | CH₂ | oxiranyl-CH | H | CF₂Cl | O | 0 |
| A569 | CH₂ | cyclobutyl-CH | H | CF₂Cl | O | 0 |
| A570 | CH₂ | oxetanyl-CH | H | CF₂Cl | O | 0 |
| A571 | CH₂ | cyclopentyl-CH | H | CF₂Cl | O | 0 |

-continued

| Radical | R₁ | R₂ | R₄ | R₃ | X₁ | p |
|---|---|---|---|---|---|---|
| A572 | CH₂ | tetrahydrofuran-CH | H | CF₂Cl | O | 0 |
| A573 | CH₂ | cyclohexyl-CH | H | CF₂Cl | O | 0 |
| A574 | CH₂ | tetrahydropyran-2-yl-CH | H | CF₂Cl | O | 0 |
| A575 | CH₂ | tetrahydropyran-3-yl-CH | H | CF₂Cl | O | 0 |
| A576 | CH₂ | tetrahydropyran-4-yl-CH | H | CF₂Cl | O | 0 |
| A577 | CH₂ | 1,3-dioxan-2-yl-CH | H | CF₂Cl | O | 0 |
| A578 | CH₂ | phenyl-CH | H | CF₂Cl | O | 0 |
| A579 | CH₂ | 2-OCH₃-phenyl-CH | H | CF₂Cl | O | 0 |
| A580 | CH₂ | 2-OH-phenyl-CH | H | CF₂Cl | O | 0 |
| A581 | CH₂ | 3-OCH₃-phenyl-CH | H | CF₂Cl | O | 0 |
| A582 | CH₂ | 3-OH-phenyl-CH | H | CF₂Cl | O | 0 |
| A583 | CH₂ | thien-3-yl-CH | H | CF₂Cl | O | 0 |

-continued
| Radical | R₁ | R₂ | R₄ | R₃ | X₁ | p |
|---|---|---|---|---|---|---|
| A584 | $CH_2$ | 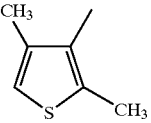 | H | $CF_2Cl$ | O | 0 |
| A585 | $CH_2$ | 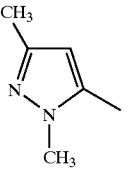 | H | $CF_2Cl$ | O | 0 |
| A586 | $CH_2$ | 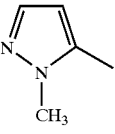 | H | $CF_2Cl$ | O | 0 |
| A587 | $CH_2$ | 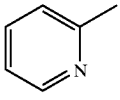 | H | $CF_2Cl$ | O | 0 |
| A588 | $CH_2$ | 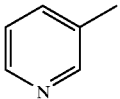 | H | $CF_2Cl$ | O | 0 |
| A589 | $CH_2$ | 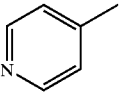 | H | $CF_2Cl$ | O | 0 |
| A590 | $CH_2$ | 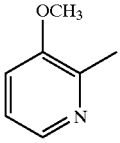 | H | $CF_2Cl$ | O | 0 |
| A591 | $CH_2$ | 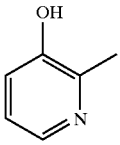 | H | $CF_2Cl$ | O | 0 |
| A592 | $CH_2$ | 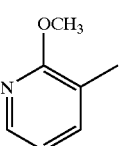 | H | $CF_2Cl$ | O | 0 |
| A593 | $CH_2$ | 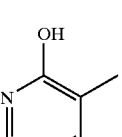 | H | $CF_2Cl$ | O | 0 |

-continued

| Radical | R₁ | R₂ | R₄ | R₃ | X₁ | p |
|---|---|---|---|---|---|---|
| A594 | CH₂ | 3-methoxy-4-methylpyridine | H | CF₂Cl | O | 0 |
| A595 | CH₂ | 3-hydroxy-4-methylpyridine | H | CF₂Cl | O | 0 |
| A596 | CH₂ | 3-methyl-4,5-dihydroisoxazole | H | CF₂Cl | O | 0 |
| A597 | CH₂ | 3-methylisoxazole | H | CF₂Cl | O | 0 |
| A598 | CH₂ | 4-fluoro-2-methoxy-1-methylbenzene | H | CF₂Cl | O | 0 |
| A599 | CH₂ | 3-methoxy-4-methylbenzonitrile | H | CF₂Cl | O | 0 |
| A600 | CH₂ | 2-methoxystyryl-CH₂ | H | CF₂Cl | O | 0 |
| A601 | CH₂ | (2-methoxyphenyl)ethynyl-CH₂ | H | CF₂Cl | O | 0 |
| A602 | CH₂ | cyclopropyl-CH₂ | H | CF₂Cl | O | 0 |
| A603 | CH₂ | oxiranyl-CH₂ | H | CF₂Cl | O | 0 |
| A604 | CH₂ | cyclobutyl-CH₂ | H | CF₂Cl | O | 0 |
| A605 | CH₂ | oxetanyl-CH₂ | H | CF₂Cl | O | 0 |

| Radical | R₁ | R₂ | R₄ | R₃ | X₁ | p |
|---|---|---|---|---|---|---|
| A606 | CH₂ | 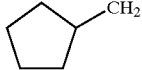 | H | CF₂Cl | O | 0 |
| A607 | CH₂ | 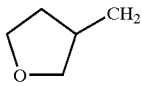 | H | CF₂Cl | O | 0 |
| A608 | CH₂ | 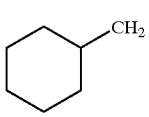 | H | CF₂Cl | O | 0 |
| A609 | CH₂ | 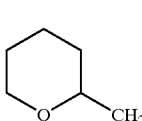 | H | CF₂Cl | O | 0 |
| A610 | CH₂ | 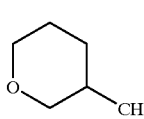 | H | CF₂Cl | O | 0 |
| A611 | CH₂ | 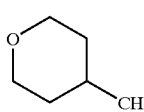 | H | CF₂Cl | O | 0 |
| A612 | CH₂ | 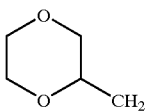 | H | CF₂Cl | O | 0 |
| A613 | CH₂ | 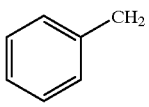 | H | CF₂Cl | O | 0 |
| A614 | CH₂ | 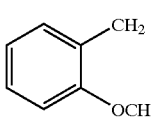 | H | CF₂Cl | O | 0 |
| A615 | CH₂ | 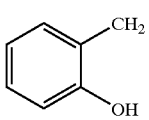 | H | CF₂Cl | O | 0 |
| A616 | CH₂ | 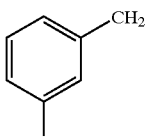 | H | CF₂Cl | O | 0 |
| A617 | CH₂ | 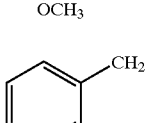 | H | CF₂Cl | O | 0 |

| Radical | R₁ | R₂ | R₄ | R₃ | X₁ | p |
|---|---|---|---|---|---|---|
| A618 | CH₂ | 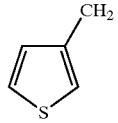 3-methylthiophene-CH₂ | H | CF₂Cl | O | 0 |
| A619 | CH₂ | 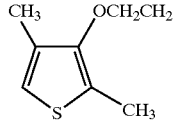 2,4-dimethyl-3-ethoxythiophene | H | CF₂Cl | O | 0 |
| A620 | CH₂ | 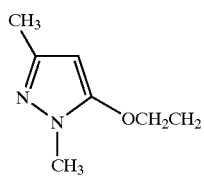 1,3-dimethyl-5-ethoxypyrazole | H | CF₂Cl | O | 0 |
| A621 | CH₂ | 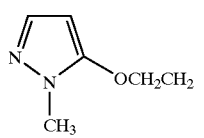 1-methyl-5-ethoxypyrazole | H | CF₂Cl | O | 0 |
| A622 | CH₂ | 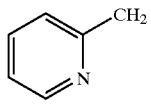 2-pyridyl-CH₂ | H | CF₂Cl | O | 0 |
| A623 | CH₂ | 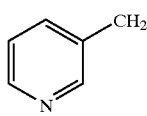 3-pyridyl-CH₂ | H | CF₂Cl | O | 0 |
| A624 | CH₂ | 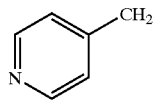 4-pyridyl-CH₂ | H | CF₂Cl | O | 0 |
| A625 | CH₂ | 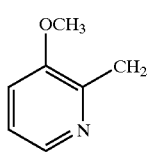 3-methoxy-2-pyridyl-CH₂ | H | CF₂Cl | O | 0 |
| A626 | CH₂ | 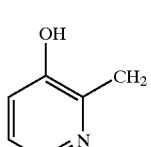 3-hydroxy-2-pyridyl-CH₂ | H | CF₂Cl | O | 0 |
| A627 | CH₂ | 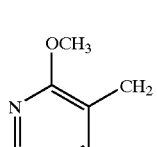 2-methoxy-3-pyridyl-CH₂ | H | CF₂Cl | O | 0 |

-continued

| Radical | R₁ | R₂ | R₄ | R₃ | X₁ | p |
|---|---|---|---|---|---|---|
| A628 | CH₂ | 3-methyl-2-hydroxypyridin-3-ylmethyl (2-OH, 3-CH₂ pyridine) | H | CF₂Cl | O | 0 |
| A629 | CH₂ | 3-methoxy-4-methylpyridin-4-ylmethyl (3-OCH₃, 4-CH₂ pyridine) | H | CF₂Cl | O | 0 |
| A630 | CH₂ | 3-hydroxy-4-methylpyridin-4-ylmethyl (3-OH, 4-CH₂ pyridine) | H | CF₂Cl | O | 0 |
| A631 | CH₂ | (4,5-dihydroisoxazol-3-yl)methyl | H | CF₂Cl | O | 0 |
| A632 | CH₂ | (isoxazol-3-yl)methyl | H | CF₂Cl | O | 0 |
| A633 | CH₂ | 4-fluoro-2-methoxybenzyl | H | CF₂Cl | O | 0 |
| A634 | CH₂ | 4-ethoxy-3-methoxy-benzonitrile-yl | H | CF₂Cl | O | 0 |
| A635 | CH₂ | 2-ethoxy-3-methoxyphenyl | H | CF₂Cl | O | 0 |
| A636 | CH₂ | 2-(methoxymethoxy)-3-methoxyphenyl (O-CH₂, OCH₃) | H | CF₂Cl | O | 0 |
| A637 | CH₂ | CH₃ | H | CHF₂ | O | 0 |
| A638 | CH₂ | CH₂CH₃ | H | CHF₂ | O | 0 |
| A639 | CH₂ | (CH₃)₂CH | H | CHF₂ | O | 0 |
| A640 | CH₂ | PhCH₂ | H | CHF₂ | O | 0 |
| A641 | CH₂ | CH₃ | H | CHF₂ | S | 0 |
| A642 | CH₂ | CH₃ | H | CHF₂ | O | 0 |
| A643 | CH₂ | CH₃ | H | CHF₂ | O | 0 |
| A644 | CH₂ | CH₃OCH₂ | H | CHF₂ | O | 0 |
| A645 | CH₂ | CH₃CH₂OCH₂ | H | CHF₂ | O | 0 |
| A646 | CH₂ | CH₃OCH₂CH₂ | H | CHF₂ | O | 0 |
| A647 | CH₂ | CH₃CH₂OCH₂CH₂ | H | CHF₂ | O | 0 |
| A648 | CH₂ | CH₃OC(CH₃)₂CH₂ | H | CHF₂ | O | 0 |
| A649 | CH₂ | CH₃OCH(CH₃)CH₂ | H | CHF₂ | O | 0 |

-continued
| Radical | R₁ | R₂ | R₄ | R₃ | X₁ | p |
|---|---|---|---|---|---|---|
| A650 | CH₂ | CH₃OCH₂CH(CH₂) | H | CHF₂ | O | 0 |
| A651 | CH₂ | CH₃OCH₂C(CH₃)₂ | H | CHF₂ | O | 0 |
| A652 | CH₂ | CH₃OCH(CH₃) | H | CHF₂ | O | 0 |
| A653 | CH₂ | CH₃OC(CH₃)₂ | H | CHF₂ | O | 0 |
| A654 | CH₂ | HC≡CCH₂ | H | CHF₂ | O | 0 |
| A655 | CH₂ | H₂C=CHCH₂ | H | CHF₂ | O | 0 |
| A656 | CH₂ | CH₃C≡CCH₂ | H | CHF₂ | O | 0 |
| A657 | CH₂ |  | H | CHF₂ | O | 0 |
| A658 | CH₂ |  | H | CHF₂ | O | 0 |
| A659 | CH₂ |  | H | CHF₂ | O | 0 |
| A660 | CH₂ |  | H | CHF₂ | O | 0 |
| A661 | CH₂ |  | H | CHF₂ | O | 0 |
| A662 | CH₂ |  | H | CHF₂ | O | 0 |
| A663 | CH₂ |  | H | CHF₂ | O | 0 |
| A664 | CH₂ |  | H | CHF₂ | O | 0 |
| A665 | CH₂ |  | H | CHF₂ | O | 0 |
| A666 | CH₂ |  | H | CHF₂ | O | 0 |
| A667 | CH₂ |  | H | CHF₂ | O | 0 |
| A668 | CH₂ |  | H | CHF₂ | O | 0 |
| A669 | CH₂ |  | H | CHF₂ | O | 0 |

| Radical | R₁ | R₂ | R₄ | R₃ | X₁ | p |
|---|---|---|---|---|---|---|
| A670 | CH₂ | 2-hydroxyphenyl | H | CHF₂ | O | 0 |
| A671 | CH₂ | 3-methoxyphenyl | H | CHF₂ | O | 0 |
| A672 | CH₂ | 3-hydroxyphenyl | H | CHF₂ | O | 0 |
| A673 | CH₂ | 3-thienyl | H | CHF₂ | O | 0 |
| A674 | CH₂ | 2,3,4-trimethylthien-5-yl | H | CHF₂ | O | 0 |
| A675 | CH₂ | 1,3-dimethylpyrazol-5-yl | H | CHF₂ | O | 0 |
| A676 | CH₂ | 1-methylpyrazol-5-yl | H | CHF₂ | O | 0 |
| A677 | CH₂ | 2-pyridyl | H | CHF₂ | O | 0 |
| A678 | CH₂ | 3-pyridyl | H | CHF₂ | O | 0 |
| A679 | CH₂ | 4-pyridyl | H | CHF₂ | O | 0 |
| A680 | CH₂ | 3-methoxypyridin-2-yl | H | CHF₂ | O | 0 |

| Radical | R₁ | R₂ | R₄ | R₃ | X₁ | p |
|---|---|---|---|---|---|---|
| A681 | CH₂ | 2-methyl-3-hydroxypyridin-yl | H | CHF₂ | O | 0 |
| A682 | CH₂ | 2-methoxy-3-methylpyridin-yl | H | CHF₂ | S | 0 |
| A683 | CH₂ | 2-hydroxy-3-methylpyridin-yl | H | CHF₂ | SO | 0 |
| A684 | CH₂ | 3-methoxy-4-methylpyridin-yl | H | CHF₂ | SO₂ | 0 |
| A685 | CH₂ | 3-hydroxy-4-methylpyridin-yl | H | CHF₂ | O | 0 |
| A686 | CH₂ | 3-methyl-4,5-dihydroisoxazol-yl | H | CHF₂ | O | 0 |
| A687 | CH₂ | 3-methylisoxazol-yl | H | CHF₂ | O | 0 |
| A688 | CH₂ | 4-fluoro-2-methoxy-1-methylphenyl | H | CHF₂ | O | 0 |
| A689 | CH₂ | 4-cyano-2-methoxy-1-methylphenyl | H | CHF₂ | O | 0 |
| A690 | CH₂ | 2-(2-methoxyphenyl)vinyl | H | CHF₂ | O | 0 |

-continued
| Radical | R₁ | R₂ | R₄ | R₃ | X₁ | p |
|---|---|---|---|---|---|---|
| A691 | CH₂ | 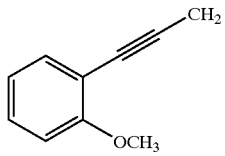 | H | CHF₂ | O | 0 |
| A692 | CH₂ | 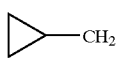 | H | CHF₂ | O | 0 |
| A693 | CH₂ | 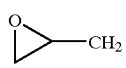 | H | CHF₂ | O | 0 |
| A694 | CH₂ | 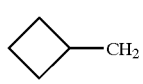 | H | CHF₂ | O | 0 |
| A695 | CH₂ | 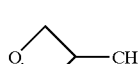 | H | CHF₂ | O | 0 |
| A696 | CH₂ | 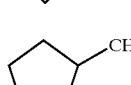 | H | CHF₂ | O | 0 |
| A697 | CH₂ | 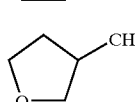 | H | CHF₂ | O | 0 |
| A698 | CH₂ | 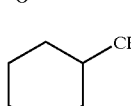 | H | CHF₂ | O | 0 |
| A699 | CH₂ | 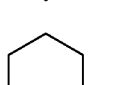 | H | CHF₂ | O | 0 |
| A700 | CH₂ | 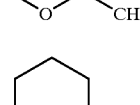 | H | CHF₂ | O | 0 |
| A701 | CH₂ | 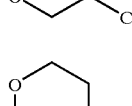 | H | CHF₂ | O | 0 |
| A702 | CH₂ | 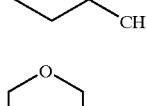 | H | CHF₂ | O | 0 |
| A703 | CH₂ | 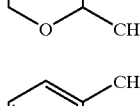 | H | CHF₂ | O | 0 |
| A704 | CH₂ | 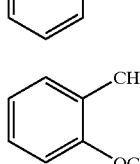 | H | CHF₂ | O | 0 |

-continued

| Radical | R₁ | R₂ | R₄ | R₃ | X₁ | p |
|---|---|---|---|---|---|---|
| A705 | CH₂ | 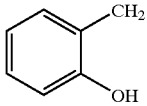 2-hydroxybenzyl (CH₂-C₆H₄-OH) | H | CHF₂ | O | 0 |
| A706 | CH₂ | 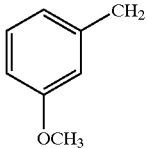 3-methoxybenzyl | H | CHF₂ | O | 0 |
| A707 | CH₂ | 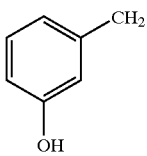 3-hydroxybenzyl | H | CHF₂ | O | 0 |
| A708 | CH₂ | 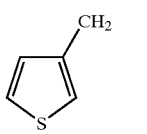 thiophen-3-ylmethyl | H | CHF₂ | O | 0 |
| A709 | CH₂ | 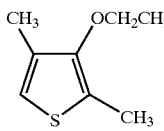 (2,4-dimethyl-3-ethoxythiophen-?-yl)methyl | H | CHF₂ | O | 0 |
| A710 | CH₂ | 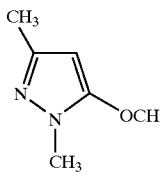 (5-ethoxy-1,3-dimethylpyrazol-?-yl) | H | CHF₂ | O | 0 |
| A711 | CH₂ | 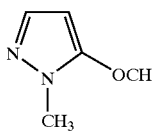 (5-ethoxy-1-methylpyrazol-?-yl) | H | CHF₂ | O | 0 |
| A712 | CH₂ | 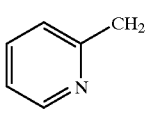 pyridin-2-ylmethyl | H | CHF₂ | O | 0 |
| A713 | CH₂ | 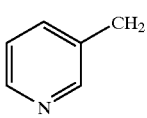 pyridin-3-ylmethyl | H | CHF₂ | O | 0 |
| A714 | CH₂ | 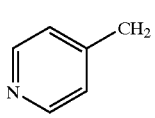 pyridin-4-ylmethyl | H | CHF₂ | O | 0 |
| A715 | CH₂ | 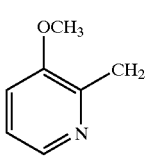 (3-methoxypyridin-2-yl)methyl | H | CHF₂ | O | 0 |

-continued

| Radical | R₁ | R₂ | R₄ | R₃ | X₁ | p |
|---|---|---|---|---|---|---|
| A716 | CH₂ | 2-methyl-3-hydroxypyridine-CH₂ | H | CHF₂ | O | 0 |
| A717 | CH₂ | 2-methoxy-3-methylpyridine-CH₂ | H | CHF₂ | O | 0 |
| A718 | CH₂ | 2-hydroxy-3-methylpyridine-CH₂ | H | CHF₂ | O | 0 |
| A719 | CH₂ | 3-methoxy-4-methylpyridine-CH₂ | H | CHF₂ | O | 0 |
| A720 | CH₂ | 3-hydroxy-4-methylpyridine-CH₂ | H | CHF₂ | O | 0 |
| A721 | CH₂ | 3-methyl-4,5-dihydroisoxazole-CH₂ | H | CHF₂ | O | 0 |
| A722 | CH₂ | 3-methylisoxazole-CH₂ | H | CH₂ | O | 0 |
| A723 | CH₂ | 4-fluoro-2-methoxyphenyl-CH₂ | H | CHF₂ | O | 0 |
| A724 | CH₂ | 4-ethoxy-3-methoxy-cyanophenyl-CH₂ | H | CHF₂ | O | 0 |
| A725 | CH₂ | 2-ethoxy-3-methoxypyridine-CH₂ | H | CHF₂ | O | 0 |

-continued

| Radical | R₁ | R₂ | R₄ | R₃ | X₁ | p |
|---|---|---|---|---|---|---|
| A726 | CH₂ | 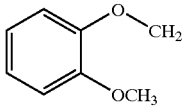 | H | CHF₂ | O | 0 |
| A727 | CH₂ | CH₃ | H | CF₃ | O | 1 |
| A728 | CH₂ | CH₂CH₃ | H | CF₃ | O | 1 |
| A729 | CH₂ | (CH₃)₂CH | H | CF₃ | O | 1 |
| A730 | CH₂ | PhCH₂ | H | CF₃ | O | 1 |
| A731 | CH₂ | CH₃ | H | CF₃ | S | 1 |
| A732 | CH₂ | CH₃ | H | CF₃ | SO | 1 |
| A733 | CH₂ | CH₃ | H | CF₃ | SO₂ | 1 |
| A734 | CH₂ | CH₃OCH₂ | H | CF₃ | O | 1 |
| A735 | CH₂ | CH₃CH₂OCH₂ | H | CF₃ | O | 1 |
| A736 | CH₂ | CH₃OCH₂CH₂ | H | CF₃ | O | 1 |
| A737 | CH₂ | CH₃CH₂OCH₂CH₂ | H | CF₃ | O | 1 |
| A738 | CH₂ | CH₃OC(CH₃)₂CH₂ | H | CF₃ | O | 1 |
| A739 | CH₂ | CH₃OCH(CH₃)CH₂ | H | CF₃ | O | 1 |
| A740 | CH₂ | CH₃OCH₂CH(CH₃) | H | CF₃ | O | 1 |
| A741 | CH₂ | CH₃OCH₂C(CH₃)₂ | H | CF₃ | O | 1 |
| A742 | CH₂ | CH₃OCH(CH₃) | H | CF₃ | O | 1 |
| A743 | CH₂ | CH₃OC(CH₃)₂ | H | CF₃ | O | 1 |
| A744 | CH₂ | HC≡CCH₂ | H | CF₃ | O | 1 |
| A745 | CH₂ | H₂C=CHCH₂ | H | CF₃ | O | 1 |
| A746 | CH₂ | CH₃C≡CCH₂ | H | CF₃ | O | 1 |
| A747 | CH₂ |  | H | CF₃ | O | 1 |
| A748 | CH₂ |  | H | CF₃ | O | 1 |
| A749 | CH₂ |  | H | CF₃ | O | 1 |
| A750 | CH₂ |  | H | CF₃ | O | 1 |
| A751 | CH₂ |  | H | CF₃ | O | 1 |
| A752 | CH₂ |  | H | CF₃ | O | 1 |
| A753 | CH₂ |  | H | CF₃ | O | 1 |
| A754 | CH₂ |  | H | CF₃ | O | 1 |
| A755 | CH₂ |  | H | CF₃ | O | 1 |
| A756 | CH₂ |  | H | CF₃ | O | 1 |

-continued
| Radical | R₁ | R₂ | R₄ | R₃ | X₁ | p |
|---|---|---|---|---|---|---|
| A757 | CH₂ | 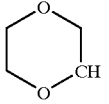 | H | CF₃ | O | 1 |
| A758 | CH₂ | 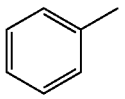 | H | CF₃ | O | 1 |
| A759 | CH₂ | 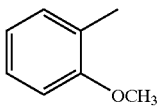 | H | CF₃ | O | 1 |
| A760 | CH₂ | 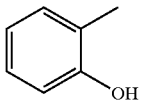 | H | CF₃ | O | 1 |
| A761 | CH₂ | 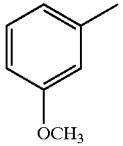 | H | CF₃ | O | 1 |
| A762 | CH₂ | 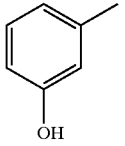 | H | CF₃ | O | 1 |
| A763 | CH₂ | 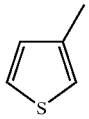 | H | CF₃ | O | 1 |
| A764 | CH₂ | 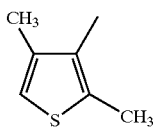 | H | CF₃ | O | 1 |
| A765 | CH₂ | 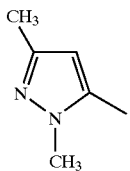 | H | CF₃ | O | 1 |
| A766 | CH₂ | 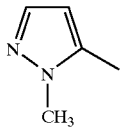 | H | CF₃ | O | 1 |
| A767 | CH₂ | 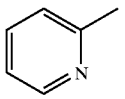 | H | CF₃ | O | 1 |

| Radical | R₁ | R₂ | R₄ | R₃ | X₁ | p |
|---|---|---|---|---|---|---|
| A768 | CH₂ | 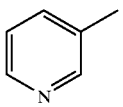 | H | CF₃ | O | 1 |
| A769 | CH₂ | 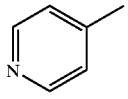 | H | CF₃ | O | 1 |
| A770 | CH₂ | 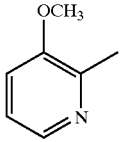 | H | CF₃ | O | 1 |
| A771 | CH₂ | 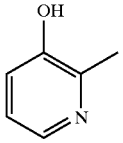 | H | CF₃ | O | 1 |
| A772 | CH₂ | 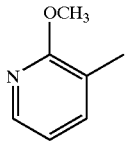 | H | CF₃ | O | 1 |
| A773 | CH₂ | 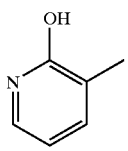 | H | CF₃ | O | 1 |
| A774 | CH₂ | 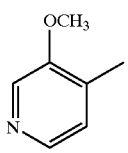 | H | CF₃ | O | 1 |
| A775 | CH₂ | 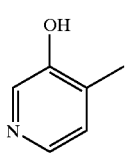 | H | CF₃ | O | 1 |
| A776 | CH₂ | 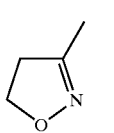 | H | CF₃ | O | 1 |
| A777 | CH₂ | 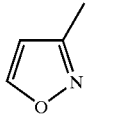 | H | CF₃ | O | 1 |
| A778 | CH₂ | 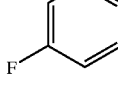 | H | CF₃ | O | 1 |

-continued

| Radical | R₁ | R₂ | R₄ | R₃ | X₁ | p |
|---|---|---|---|---|---|---|
| A779 | CH₂ | 4-methyl-3-methoxy-benzonitrile | H | CF₃ | O | 1 |
| A780 | CH₂ | 2-methoxy-phenyl-CH=CH-CH₂- | H | CF₃ | O | 1 |
| A781 | CH₂ | 2-methoxy-phenyl-C≡C-CH₂- | H | CF₃ | O | 1 |
| A782 | CH₂ | cyclopropyl-CH₂- | H | CF₃ | O | 1 |
| A783 | CH₂ | oxiranyl-CH₂- | H | CF₃ | O | 1 |
| A784 | CH₂ | cyclobutyl-CH₂- | H | CF₃ | O | 1 |
| A785 | CH₂ | oxetanyl-CH₂- | H | CF₃ | O | 1 |
| A786 | CH₂ | cyclopentyl-CH₂- | H | CF₃ | O | 1 |
| A787 | CH₂ | tetrahydrofuran-3-yl-CH₂- | H | CF₃ | O | 1 |
| A788 | CH₂ | cyclohexyl-CH₂- | H | CF₃ | O | 1 |
| A789 | CH₂ | tetrahydropyran-2-yl-CH₂- | H | CF₃ | O | 1 |
| A790 | CH₂ | tetrahydropyran-3-yl-CH₂- | H | CF₃ | O | 1 |
| A791 | CH₂ | tetrahydropyran-4-yl-CH₂- | H | CF₃ | O | 1 |

| Radical | R₁ | R₂ | R₄ | R₃ | X₁ | p |
|---|---|---|---|---|---|---|
| A792 | CH₂ | 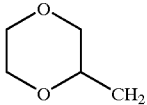 | H | CF₃ | O | 1 |
| A793 | CH₂ | 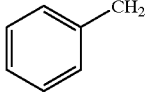 | H | CF₃ | O | 1 |
| A794 | CH₂ | 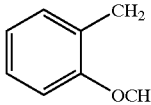 | H | CF₃ | O | 1 |
| A795 | CH₂ | 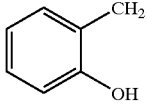 | H | CF₃ | O | 1 |
| A796 | CH₂ | 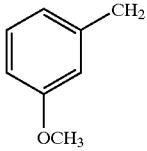 | H | CF₃ | O | 1 |
| A797 | CH₂ | 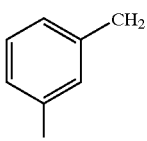 | H | CF₃ | O | 1 |
| A798 | CH₂ | 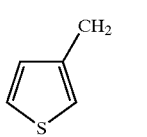 | H | CF₃ | O | 1 |
| A799 | CH₂ | 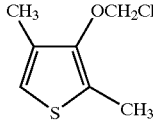 | H | CF₃ | O | 1 |
| A800 | CH₂ | 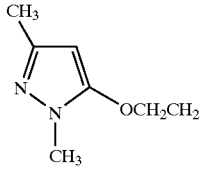 | H | CF₃ | O | 1 |
| A801 | CH₂ | 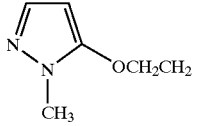 | H | CF₃ | O | 1 |
| A802 | CH₂ | 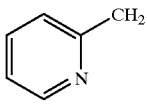 | H | CF₃ | O | 1 |

-continued
| Radical | R₁ | R₂ | R₄ | R₃ | X₁ | p |
|---|---|---|---|---|---|---|
| A803 | CH₂ | 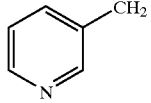 | H | CF₃ | O | 1 |
| A804 | CH₂ | 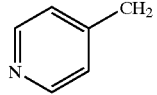 | H | CF₃ | O | 1 |
| A805 | CH₂ | 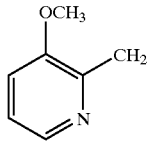 | H | CF₃ | O | 1 |
| A806 | CH₂ | 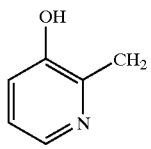 | H | CF₃ | O | 1 |
| A807 | CH₂ | 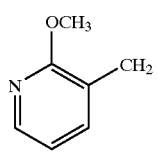 | H | CF₃ | O | 1 |
| A808 | CH₂ | 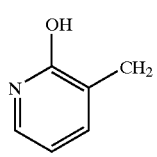 | H | CF₃ | O | 1 |
| A809 | CH₂ | 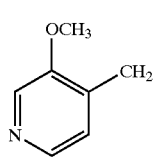 | H | CF₃ | O | 1 |
| A810 | CH₂ | 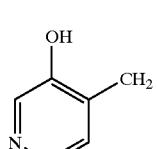 | H | CF₃ | O | 1 |
| A811 | CH₂ | 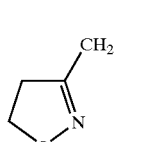 | H | CF₃ | O | 1 |
| A812 | CH₂ | 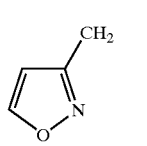 | H | CF₃ | O | 1 |

| Radical | R$_1$ | R$_2$ | R$_4$ | R$_3$ | X$_1$ | p |
|---|---|---|---|---|---|---|
| A813 | CH$_2$ | 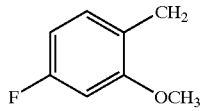 | H | CF$_3$ | O | 1 |
| A814 | CH$_2$ | 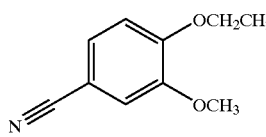 | H | CF$_3$ | O | 1 |
| A815 | CH$_2$ | 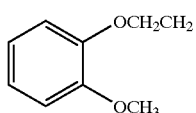 | H | CF$_3$ | O | 1 |
| A816 | CH$_2$ | 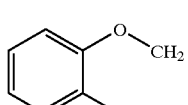 | H | CF$_3$ | O | 1 |
| A817 | CH$_2$ | CH$_3$SCH$_2$CH$_2$ | H | CF$_3$ | O | 0 |
| A818 | CH$_2$ | CH$_3$SOCH$_2$CH$_2$ | H | CF$_3$ | O | 0 |
| A819 | CH$_2$ | CH$_3$SO$_2$CH$_2$CH$_2$ | H | CF$_3$ | O | 0 |
| A820 | CH$_2$ | CH$_3$OCH$_2$CH$_2$ | H | CF$_2$Cl | O | 1 |
| A821 | CH$_2$ | CH$_3$OCH$_2$CH$_2$ | H | CF$_2$H | O | 1 |
| A822 | CH$_2$ | CH$_3$OCH$_2$CH$_2$ | F | CF$_3$ | O | 0 |
| A823 | CH$_2$ | CH$_3$OCH$_2$CH$_2$ | CH$_3$ | CF$_3$ | O | 0 |
| A824 | CH$_2$ | CH$_3$OCH$_2$CH$_2$ | CH$_3$ | CF$_3$ | O | 1 |
| A825 | CH$_2$ | CH$_3$OCH$_2$CH$_2$ | H | CF$_3$ | S | 0 |
| A826 | CH$_2$ | CH$_3$OCH$_2$CH$_2$ | H | CF$_3$ | SO | 0 |
| A827 | CH$_2$ | CH$_3$OCH$_2$CH$_2$ | CH$_3$ | CF$_3$ | SO$_2$ | 0 |
| A828 | CH$_2$ | CH$_3$SO$_2$CH$_2$CH$_2$ | CH$_3$ | CF$_3$ | O | 0 |
| A829 | CH$_2$ | 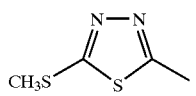 | H | CF$_3$ | S | 0 |
| A830 | CH$_2$ | 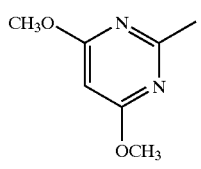 | H | CF$_3$ | S | 0 |
| A831 | CH$_2$ | 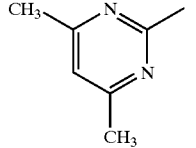 | CH$_3$ | CF$_3$ | S | 0 |
| A832 | CH$_2$ | 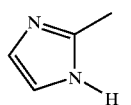 | CH$_3$ | CF$_3$ | S | 0 |
| A833 | CH$_2$ | CH$_3$C(O) | H | CF$_3$ | O | 0 |
| A834 | CH$_2$ | CF$_3$CH$_2$ | H | CF$_3$ | O | 0 |
| A835 | CH$_2$ | CH$_3$OCH$_2$CH$_2$OCH$_2$CH$_2$ | H | CF$_3$ | O | 0 |
| A836 | CH$_2$ | HC≡CCH$_2$CH$_2$ | H | CF$_3$ | O | 0 |
| A837 | CH$_2$ |  | H | CF$_3$ | O | 0 |

-continued

| Radical | $R_1$ | $R_2$ | $R_4$ | $R_3$ | $X_1$ | p |
|---|---|---|---|---|---|---|
| A838 | $CH_2$ | $CH_3CH_2C(OCH_3)HOCH_2CH_2$ | H | $CF_3$ | O | 0 |
| A839 | $CH_2$ | $(CH_3)_3CC(O)$ | H | $CF_3$ | O | 0 |
| A840 | $CH_2$ | $CH_2{=}CHCH_2OCH_2CH_2$ | H | $CF_3$ | O | 0 |
| A841 | $CH_2$ | $CH_3CH_2CH_2OCH_2CH_2$ | H | $CF_3$ | O | 0 |
| A842 | $CH_2$ | tetrahydropyran-2-yl-O-$CH_2$ | H | $CF_3$ | O | 0 |
| A843 | $CH_2$ | n-Heptyl-C(O) | H | $CF_3$ | O | 0 |
| A844 | $CH_2$ | Phenyl-C(O) | H | $CF_3$ | O | 0 |
| A845 | $CH_2$ | $CF_3CH_2OCH_2CH_2$ | H | $CF_3$ | O | 0 |
| A846 | $CH_2$ | $CH_3OCH_2CH_2CH_2$ | H | $CF_3$ | O | 0 |
| A847 | $CH_2$ | $HOCH_2CH_2$ | H | $CF_3$ | O | 0 |
| A848 | $CH_2$ | (tetrahydrofuran-2-yl)-$CH_2$ | H | $CF_3$ | O | 0 |
| A849 | $CH_2$ | $N{\equiv}CCH_2CH_2$ | H | $CF_3$ | O | 0 |
| A850 | $CH_2$ | $ClCH_2CH_2$ | H | $CF_3$ | O | 0 |
| A851 | $CH_2$ | 1,3-dioxan-2-yl (CH) | H | $CF_3$ | O | 0 |
| A852 | $CH_2$ | (1,3-dioxolan-2-yl)-$CH_2$ | H | $CF_3$ | O | 0 |
| A853 | $CH_2$ | $CH_3OCH_2C(Br)HCH_2$ | H | $CF_3$ | O | 0 |
| A854 | $CH_2$ | (thiophen-2-yl)-$CH_2$ | H | $CF_3$ | O | 0 |
| A855 | $CH_2$ | Phenyl-$CH_2OCH_2CH_2$ | H | $CF_3$ | O | 0 |
| A856 | $CH_2$ | $HOCH_2CH_2$ | H | $CF_3$ | O | 0 |
| A857 | $CH_2$ | Phenyl-$CH_2OCH_2OCH_2CH_2$ | H | $CF_3$ | O | 0 |
| A858 | $CH_2$ | $CH_3(OCH_2CH_2)_3$ | H | $CF_3$ | O | 0 |
| A859 | $CH_2$ | $CH_3CH_2OC(CH_3)HOCH_2CH_2$ | H | $CF_3$ | O | 0 |
| A860 | $CH_2$ | n-Heptyl-C(O)$OCH_2CH_2$ | H | $CF_3$ | O | 0 |
| A861 | $CH_2$ | $CH_3C(O)OCH_2CH_2$ | H | $CF_3$ | O | 0 |
| A862 | $CH_2$ | $CH_3SO_2OCH_2CH_2$ | H | $CF_3$ | O | 0 |
| A863 | $CH_2$ | Phenyl-$CH_2OCH_2CH_2$ | H | $CF_3$ | O | 0 |
| A864 | $CH_2$ | $CH_3$ | H | $CF_3$ | —$NCH_3SO_2$— | 0 |
| A865 | $CH_2$ | $HOCH_2C(OH)HCH_2$ | H | $CF_3$ | O | 0 |
| A866 | $CH_2$ | Phenyl-C(O)$OCH_2CH_2$ | H | $CF_3$ | O | 0 |
| A867 | $CH_2$ | t-Butyl-C(O)$OCH_2CH_2$ | H | $CF_3$ | O | 0 |
| A868 | $CH_2$ | $CH_3OC(O)CH_2$ | H | $CF_3$ | O | 0 |

In the table below, in the case of rings, the ring attachment points for the substituents $A_1$ and $A_2$ are at the carbon atom which is marked "C", for example

in the case of open-chain structures, "$(CH_3)_2C$" denotes, for example,

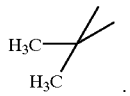

In the formula A-Q, denotes $Q_1$

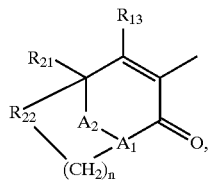 (Q₁)

and $Q_1$ denotes the following radicals B:

| Radical | $A_1$ | $A_2$ | n | $R_{21}$ | $R_{22}$ | $R_{13}$ |
|---|---|---|---|---|---|---|
| B1  | $CH_2$ | $CH_2$ | 0 | H | H | OH |
| B2  | $CH_2$ | $CH_2$ | 0 | $CH_3$ | H | OH |
| B3  | $CH_2$ | $CH_2$ | 0 | $CH_3$ | $CH_3$ | OH |
| B4  | $(CH_3)CH$ | $CH_2$ | 0 | $CH_3$ | $CH_3$ | OH |
| B5  | $(CH_3)_2C$ | $CH_2$ | 0 | $CH_3$ | $CH_3$ | OH |
| B6  | CH | CH | 0 | $CH_3$ | — | OH |
| B7  | $CH_2$ | $CH_2$ | 0 | $CH_3$ | $CH_2=CHCH_2$ | OH |
| B8  | $CH_2$ | $CH_2$ | 0 | $CH_3$ | $HC\equiv CCH_2$ | OH |
| B9  | $CH_2$ | $CH_2$ | 0 | $CH_3$ | $CH_3S$ | OH |
| B10 | $CH_2$ | $CH_2$ | 0 | $CH_3$ | $CH_3SO$ | OH |
| B11 | $CH_2$ | $CH_2$ | 0 | $OH3$ | $CH_3SO_2$ | OH |
| B12 | $CH_2$ | $CH_2$ | 0 | $CH_3$ | $CH_3O$ | OH |
| B13 | $CH_2$ | $CH_2$ | 0 | $CH_3$ | $CH_3OC(O)$ | OH |
| B14 | $CH_2$ | $CH_2$ | 0 | $CH_3$ | $CH_3CH_2OC(O)$ | OH |
| B15 | $CH_2$ | $(CH_3)_2C$ | 0 | H | H | OH |
| B16 | (γ-butyrolactone ring with C) | $CH_2$ | 0 | H | H | OH |
| B17 | (cyclopropyl-C) | $CH_2$ | 0 | H | H | OH |
| B18 | (cyclopropyl-C) | $CH_2$ | 0 | $CH_3$ | H | OH |
| B19 | (cyclopropyl-C) | $CH_2$ | 0 | $CH_3$ | $CH_3$ | OH |
| B20 | (cyclobutyl-C) | $CH_2$ | 0 | H | H | OH |
| B21 | (cyclobutyl-C) | $CH_2$ | 0 | $CH_3$ | H | OH |
| B22 | (cyclobutyl-C) | $CH_2$ | 0 | $CH_3$ | $CH_3$ | OH |
| B23 | $(CH_3)_2C$ | O | 0 | $CH_3$ | $CH_3$ | OH |
| B24 | $CH_2$ | O | 0 | $CH_3$ | $CH_3$ | OH |
| B25 | $CH_3N$ | O | 0 | $CH_3$ | $CH_3$ | OH |
| B26 | (cyclopropyl-N) | O | 0 | $CH_3$ | $CH_3$ | OH |
| B27 | $CH_3N$ | $CH_2$ | 0 | $CH_3$ | $CH_3$ | OH |

-continued

| Radical | $A_1$ | $A_2$ | n | $R_{21}$ | $R_{22}$ | $R_{13}$ |
|---|---|---|---|---|---|---|
| B28 | $CH_3N$ | $(CH_3)CH$ | 0 | H | H | OH |
| B29 | $CH_3N$ | $(CH_3)CH$ | 0 | $CH_3$ | H | OH |
| B30 | NH | $(CH_3)C$ | 0 | H | — | OH |
| B31 | NH | CH | 0 | $CH_3$ | — | OH |
| B32 | $CH_3N$ | $(CH_3)C$ | 0 | H | — | OH |
| B33 | $CH_3N$ | CH | 0 | $CH_3$ | — | OH |
| B34 | O | $(CH_3)_2C$ | 0 | H | — | OH |
| B35 | O | $(CH_3)_2C$ | 0 | $CH_3$ | $CH_3$ | OH |
| B36 | O | $(CH_3)_2C$ | 0 | $CH_3$ | H | OH |
| B37 | O | $(CH_3)C$ | 0 | H | — | OH |
| B38 | O | CH | 0 | $CH_3$ | — | OH |
| B39 | $(CH_3)_2C$ | C=O | 0 | $CH_3$ | $CH_3$ | OH |
| B40 | $(CH_3)_2C$ | $(OH)CH$ | 0 | $CH_3$ | $CH_3$ | OH |
| B41 | cyclopropyl-C | C=O | 0 | $CH_3$ | $CH_3$ | OH |
| B42 | cyclopropyl-C | C=O | 0 | $CH_2$ | $CH_2$ | OH |
| B43 | $(CH_3)_2C$ | 1,3-dithiolan-2-yl | 0 | $CH_3$ | $CH_3$ | OH |
| B44 | $(CH_3)_2C$ | $CH(OCH_3)_2$ | 0 | $CH_3$ | $CH_3$ | OH |
| B45 | $(CH_3)_2C$ | 1,3-dioxolan-2-yl | 0 | $CH_3$ | $CH_3$ | OH |
| B46 | $(CH_3)_2C$ | 1,3-dioxan-2-yl | 0 | $CH_3$ | $CH_3$ | OH |
| B47 | $(CH_3)_2C$ | HON=C | 0 | $CH_3$ | $CH_3$ | OH |
| B48 | $(CH_3)_2C$ | $CH_3ON=C$ | 0 | $CH_3$ | $CH_3$ | OH |
| B49 | $(CH_3)_2C$ | BnON=C | 0 | $CH_3$ | $CH_3$ | OH |
| B50 | CH | O | 1 | H | $CH_2$ | OH |
| B51 | CH | C=O | 1 | H | $CH_2$ | OH |
| B52 | CH | $CH_2$ | 1 | H | $CH_2$ | OH |
| B53 | CH | $CH_3N$ | 1 | H | $CH_2$ | OH |
| B54 | CH | $CH_2CH_2$ | 1 | H | $CH_2$ | OH |
| B55 | CH | C=O | 2 | H | $CH_2$ | OH |
| B56 | CH | $CH_2$ | 2 | H | $CH_2$ | OH |
| B57 | CH | $CH_2$ | 1 | H | $CH_2$ | Cl |
| B58 | CH | $CH_2$ | 1 | H | $CH_2$ | $NH_2$ |
| B59 | CH | $CH_2$ | 1 | H | $CH_2$ | $CH_3SO_2NH$ |
| B60 | CH | $CH_2$ | 1 | H | $CH_2$ | $CH_3OCH_2CH_2S$ |
| B61 | CH | $CH_2$ | 1 | H | $CH_2$ | $CH_3OCH_2CH_2SO$ |
| B62 | CH | $CH_2$ | 1 | H | $CH_2$ | $CH_3OCH_2CH_2SO_2$ |
| B63 | CH | $CH_2$ | 1 | H | $CH_2$ | $(CH_3)_2NC(O)NH$ |
| B64 | CH | $CH_2$ | 1 | H | $CH_2$ | PhC(O)O |
| B65 | CH | $CH_2$ | 1 | H | $CH_2$ | $CH_3OC(O)O$ |
| B66 | CH | $CH_2$ | 1 | H | $CH_2$ | $CH_3(CH_2)_7S$ |
| B67 | CH | $CH_2$ | 1 | H | $CH_2$ | $CH_3(CH_2)_7SO$ |
| B68 | CH | $CH_2$ | 1 | H | $CH_2$ | $CH_3(CH_2)_7SO_2$ |
| B69 | CH | $CH_2$ | 1 | H | $CH_2$ | $(CH_3)_2NSO_2NH$ |
| B70 | CH | $CH_2$ | 1 | H | $CH_2$ | PhS |
| B71 | CH | $CH_2$ | 1 | H | $CH_2$ | PhSO |

-continued

| Radical | $A_1$ | $A_2$ | n | $R_{21}$ | $R_{22}$ | $R_{13}$ |
|---|---|---|---|---|---|---|
| B72 | CH | $CH_2$ | 1 | H | $CH_2$ | $PhSO_2$ |
| B73 | CH | $CH_2$ | 1 | H | $CH_2$ | 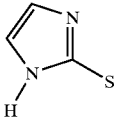 |
| B74 | CH | $CH_2$ | 1 | H | $CH_2$ | 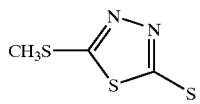 |
| B75 | $(CH_3)_2C$ | C=O | 0 | $CH_3$ | $CH_3$ | Cl |
| B76 | $(CH_3)_2C$ | C=O | 0 | $CH_3$ | $CH_3$ | $NH_2$ |
| B77 | $(CH_3)_2C$ | C=O | 0 | $CH_3$ | $CH_3$ | $CH_3SO_2NH$ |
| B78 | $(CH_3)_2C$ | C=O | 0 | $CH_3$ | $CH_3$ | $CH_3OCH_2CH_2S$ |
| B79 | $(CH_3)_2C$ | C=O | 0 | $CH_3$ | $CH_3$ | $CH_3OCH_2CH_2SO$ |
| B80 | $(CH_3)_2C$ | C=O | 0 | $CH_3$ | $CH_3$ | $CH_3OCH_2CH_2SO_2$ |
| B81 | $(CH_3)_2C$ | C=O | 0 | $CH_3$ | $CH_3$ | $(CH_3)_2NC(O)NH$ |
| B82 | $(CH_3)_2C$ | C=O | 0 | $CH_3$ | $CH_3$ | $PhC(O)O$ |
| B83 | $(CH_3)_2C$ | C=O | 0 | $CH_3$ | $CH_3$ | $CH_3OC(O)O$ |
| B84 | $(CH_3)_2C$ | C=O | 0 | $CH_3$ | $CH_3$ | $CH_3(CH_2)_7S$ |
| B85 | $(CH_3)_2C$ | C=O | 0 | $CH_3$ | $CH_3$ | $CH_3(CH_2)_7SO$ |
| B86 | $(CH_3)_2C$ | C=O | 0 | $CH_3$ | $CH_3$ | $CH_3(CH_2)_7SO_2$ |
| B87 | $(CH_3)_2C$ | C=O | 0 | $CH_3$ | $CH_3$ | $(CH_3)_2NSO_2NH$ |
| B88 | $(CH_3)_2C$ | C=O | 0 | $CH_3$ | $CH_3$ | PhS |
| B89 | $(CH_3)_2C$ | C=O | 0 | $CH_3$ | $CH_3$ | PhSO |
| B90 | $(CH_3)_2C$ | C=O | 0 | $CH_3$ | $CH_3$ | $PhSO_2$ |
| B91 | $(CH_3)_2C$ | C=O | 0 | $CH_3$ | $CH_3$ | 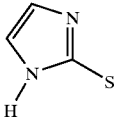 |
| B92 | $(CH_3)_2C$ | C=O | 0 | $CH_3$ | $CH_3$ | 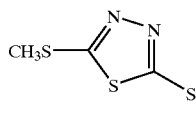 |
| B93 | $(CH_3)_2C$ | $CH_2$ | 0 | H | H | Cl |
| B94 | $(CH_3)_2C$ | $CH_2$ | 0 | H | H | $NH_2$ |
| B96 | $(CH_3)_2C$ | $CH_2$ | 0 | H | H | $CH_3OCH_2CH_2S$ |
| B97 | $(CH_3)_2C$ | $CH_2$ | 0 | H | H | $CH_3OCH_2CH_2SO$ |
| B98 | $(CH_3)_2C$ | $CH_2$ | 0 | H | H | $CH_3OCH_2CH_2SO_2$ |
| B99 | $(CH_3)_2C$ | $CH_2$ | 0 | H | H | $(CH_3)_2NC(O)NH$ |
| B100 | $(CH_3)_2C$ | $CH_2$ | 0 | H | H | $PhC(O)O$ |
| B101 | $(CH_3)_2C$ | $CH_2$ | 0 | H | H | $CH_3OC(O)O$ |
| B102 | $(CH_3)_2C$ | $CH_2$ | 0 | H | H | $CH_3(CH_2)_7S$ |
| B103 | $(CH_3)_2C$ | $CH_2$ | 0 | H | H | $CH_3(CH_2)_7SO$ |
| B104 | $(CH_3)_2C$ | $CH_2$ | 0 | H | H | $CH_3(CH_2)_7SO_2$ |
| B105 | $(CH_3)_2C$ | $CH_2$ | 0 | H | H | $(CH_3)_2NSO_2NH$ |
| B106 | $(CH_3)_2C$ | $CH_2$ | 0 | H | H | PhS |
| B107 | $(CH_3)_2C$ | $CH_2$ | 0 | H | H | PhSO |
| B108 | $(CH_3)_2C$ | $CH_2$ | 0 | H | H | $PhSO_2$ |
| B109 | $(CH_3)_2C$ | $CH_2$ | 0 | H | H | 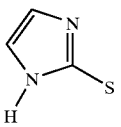 |
| B110 | $(CH_3)_2C$ | $CH_2$ | 0 | H | H | 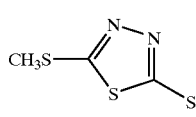 |
| B111 | $CH_2$ | $(CH_3)CH$ | 0 | H | H | OH |
| B112 | $CH_2$ | $CH_2$ | 1 | H | $CH_2$ | t-Butyl-C(O)O |
| B113 | $CH_2$ | $CH_2$ | 1 | H | $CH_2$ | t-Heptyl-C(O)O | or Q in the formula A-Q denotes $Q_2$

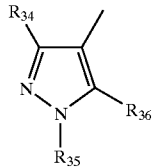

and $Q_2$ denotes the following radicals C:

| Radical | $R_{34}$ | $R_{35}$ | $R_{36}$ |
|---|---|---|---|
| C1 | $CH_3$ | H | OH |
| C2 | $CH_3$ | $CH_3$ | OH |
| C3 | H | $HC{\equiv}CCH_2$ | OH |
| C4 | H | $CH_3SO_2$ | OH |
| C5 | H | $CH_3$ | OH |
| C6 | H | $PhCH_2$ | OH |
| C7 | $CF_3$ | $CH_3$ | OH |
| C8 | cyclopropyl-CH | $CH_3$ | OH |
| C9 | $CH_3OCH_2CH_2OCH_2$ | $CH_3$ | OH |
| C10 | H | $CH_3$ | Cl |
| C11 | H | $CH_3$ | $NH_2$ |
| C12 | H | $CH_3$ | $CH_3SO_2NH$ |
| C13 | H | $CH_3$ | $CH_3OCH_2CH_2S$ |
| C14 | H | $CH_3$ | $CH_3OCH_2CH_2SO$ |
| C15 | H | $CH_3$ | $CH_3OCH_2CH_2SO_2$ |
| C16 | H | $CH_3$ | $(CH_3)_2NC(O)NH$ |
| C17 | H | $CH_3$ | $PhC(O)O$ |
| C18 | H | $CH_3$ | $CH_3OC(O)O$ |
| C19 | H | $CH_3$ | $CH_3(CH_2)_7S$ |
| C20 | H | $CH_3$ | $CH_3(CH_2)_7SO$ |
| C21 | H | $CH_3$ | $CH_3(CH_2)_7SO_2$ |
| C22 | H | $CH_3$ | $(CH_3)NSO_2NH$ |
| C23 | H | $CH_3$ | PhS |
| C24 | H | $CH_3$ | PhSO |
| C25 | H | $CH_3$ | $PhSO_2$ |
| C26 | H | $CH_3$ | 2-mercapto-1H-imidazolyl |
| C27 | H | $CH_3$ | 5-(methylthio)-1,3,4-thiadiazol-2-ylthio |
| C28 | H | $CH_3$ | $CH_3SO_2O$ |
| C29 | H | $CH_3$ | p-$TolylSO_2O$ | or Q in the formula A-Q denotes $Q_3$

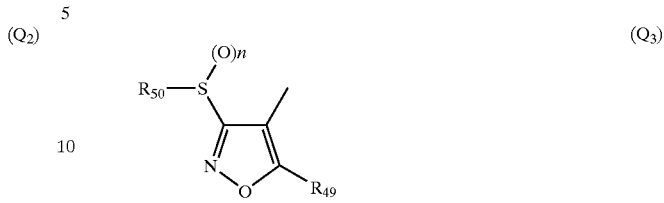

and $Q_3$ denotes the following radicals D (the point of attachment of $R_{49}$ to the heterocycle is the "CH" group):

| Radical | $R_{49}$ | $R_{50}$ | n |
|---|---|---|---|
| D1 | cyclopropyl-CH | $CH_3$ | 0 |
| D2 | cyclopropyl-CH | $CH_3$ | 1 |
| D3 | cyclopropyl-CH | $CH_3$ | 2 |
| D4 | cyclopropyl-CH | $CF_3$ | 0 |
| D5 | cyclopropyl-CH | $CF_3$ | 1 |
| D6 | cyclopropyl-CH | $CF_3$ | 2 |
| D7 | cyclopropyl-CH | Ph | 0 |
| D5 | cyclopropyl-CH | Ph | 1 |
| D9 | cyclopropyl-CH | Ph | 2 |
| D10 | cyclopropyl-CH | $PhCH_2$ | 0 |
| D11 | cyclopropyl-CH | $PhCH_2$ | 1 |
| D12 | cyclopropyl-CH | $PhCH_2$ | 2 |

TABLE 1

Intermediates for preparing the compounds of the formula I, represent as formula
A–Q
in which Q denotes hydroxyl:

| OH | OH | OH | OH | OH | OH | OH | OH | OH | OH | OH | OH |
|---|---|---|---|---|---|---|---|---|---|---|---|
| — | — | — | — | — | — | — | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | — | — | — | — | — | — |
| — | — | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A282 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | — | — | — | — | — | — | — |
| — | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| — | — | — | — | — | — | A644 | A645 | A646 | A647 | A648 | |
| A649 | A650 | A651 | A652 | A653 | A654 | A655 | A656 | A657 | A658 | A659 | A660 |
| A661 | A662 | A663 | A664 | A665 | A666 | A667 | A668 | A689 | A670 | A671 | A672 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | — | — | — | — | — | — |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 2

Compounds of the formula I, represented as compounds of the formula A–Q in which Q denotes $Q_1$ and $Q_1$ denotes the radical B52:

| B52 | B52 | B52 | B52 | B52 | B52 | B52 | B52 | B52 | B52 | B52 | B52 |
|---|---|---|---|---|---|---|---|---|---|---|---|
| A1 | A2 | A3 | A4 | A5 | A6 | A7 | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | A91 | A92 | A93 | A94 | A95 | A96 |
| A97 | A98 | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A286 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | A546 | A547 | A548 | A549 | A550 | A551 | A552 |
| A553 | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| A637 | A638 | A639 | A640 | A641 | A642 | A643 | A644 | A645 | A646 | A647 | A648 |
| A649 | A650 | A651 | A652 | A653 | A654 | A655 | A656 | A657 | A658 | A659 | A660 |
| A661 | A662 | A663 | A664 | A665 | A666 | A667 | A668 | A669 | A670 | A671 | A672 |
| A673 | A674 | A675 | A676 | A677 | A678 | A679 | A680 | A681 | A682 | A683 | A684 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | A727 | A728 | A729 | A730 | A731 | A732 |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 3

Compounds of the formula I, represented as compounds of the formula A–Q in which Q denotes $Q_1$ and $Q_1$ denotes the radical B39:

| B39 | B39 | B39 | B39 | B39 | B39 | B39 | B39 | B39 | B39 | B39 | B39 |
|---|---|---|---|---|---|---|---|---|---|---|---|
| A1 | A2 | A3 | A4 | A5 | A6 | A7 | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | A91 | A92 | A93 | A94 | A95 | A96 |
| A97 | A98 | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | A546 | A547 | A548 | A549 | A550 | A551 | A552 |
| A553 | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| A637 | A638 | A639 | A640 | A641 | A642 | A643 | A644 | A645 | A646 | A647 | A648 |
| A649 | A650 | A651 | A652 | A653 | A654 | A655 | A656 | A657 | A658 | A659 | A660 |
| A661 | A662 | A663 | A664 | A665 | A666 | A667 | A668 | A689 | A670 | A671 | A672 |
| A673 | A674 | A675 | A676 | A677 | A678 | A679 | A680 | A681 | A682 | A683 | A684 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | A727 | A728 | A729 | A730 | A731 | A732 |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 4

Compounds of the formula I, represented as compounds of the formula
A–Q
in which Q denotes $Q_1$ and $Q_1$ denotes the radical B3:

| B3 | B3 | B3 | B3 | B3 | B3 | B3 | B3 | B3 | B3 | B3 |
|---|---|---|---|---|---|---|---|---|---|---|
| — | — | — | — | — | — | — | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | — | — | — | — | — | — |
| — | — | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | — | — | — | — | — | — | — |
| — | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| — | — | — | — | — | — | — | A644 | A645 | A646 | A647 | A648 |
| A649 | A650 | A651 | A652 | A653 | A654 | A655 | A656 | A657 | A658 | A659 | A660 |
| A661 | A662 | A663 | A664 | A665 | A666 | A667 | A668 | A689 | A670 | A671 | A672 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | — | — | — | — | — | — |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 5

Compounds of the formula I, represented as compounds of the formula
A—Q
in which Q denotes Q₂ and Q₂ denotes the radical C5:

| C5 | C5 | C5 | C5 | C5 | C5 | C5 | C5 | C5 | C5 | C5 | C5 |
|---|---|---|---|---|---|---|---|---|---|---|---|
| A1 | A2 | A3 | A4 | A5 | A6 | A7 | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | A91 | A92 | A93 | A94 | A95 | A96 |
| A97 | A98 | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | A546 | A547 | A548 | A549 | A550 | A551 | A552 |
| A553 | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| A637 | A638 | A639 | A640 | A641 | A642 | A643 | A644 | A645 | A646 | A647 | A648 |
| A649 | A650 | A651 | A652 | A653 | A654 | A655 | A656 | A657 | A658 | A659 | A660 |
| A661 | A662 | A663 | A664 | A665 | A666 | A667 | A668 | A689 | A670 | A671 | A672 |
| A673 | A674 | A675 | A676 | A677 | A678 | A679 | A680 | A681 | A682 | A683 | A684 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | A727 | A728 | A729 | A730 | A731 | A732 |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 6

Compounds of the formula I, represented as compounds of the formula A—Q in which Q denotes Q₂ and Q₂ denotes the radical C2:

| C2 | C2 | C2 | C2 | C2 | C2 | C2 | C2 | C2 | C2 | C2 | C2 |
|---|---|---|---|---|---|---|---|---|---|---|---|
| A1 | A2 | A3 | A4 | A5 | A6 | A7 | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | A91 | A92 | A93 | A94 | A95 | A96 |
| A97 | A98 | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | A546 | A547 | A548 | A549 | A550 | A551 | A552 |
| A553 | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| A637 | A638 | A639 | A640 | A641 | A642 | A643 | A644 | A645 | A646 | A647 | A648 |
| A649 | A650 | A651 | A652 | A653 | A654 | A655 | A656 | A657 | A658 | A659 | A660 |
| A661 | A662 | A663 | A664 | A665 | A666 | A667 | A668 | A689 | A670 | A671 | A672 |
| A673 | A674 | A675 | A676 | A677 | A678 | A679 | A680 | A681 | A682 | A683 | A684 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | A727 | A728 | A729 | A730 | A731 | A732 |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 7

Compounds of the formula I, represented as compounds of the formula
A—Q
in which Q denotes Q₂ and Q₂ denotes the radicals D1, D2 or D3:

| D1/D2 D3 | D1/D2 D3 | D1/D2 D3 | D1/D2 D3 | D1/D2 D3 | D1/D2 D3 | D1/D2 D3 | D1/D2 D3 | D1/D2 D3 | D1/D2 D3 | D1/D2 D3 | D1/D2 D3 |
|---|---|---|---|---|---|---|---|---|---|---|---|
| — | — | — | — | — | — | — | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | — | — | — | — | — | — |
| — | — | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | — | — | — | — | — | — | — |
| — | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| — | — | — | — | — | — | A644 | A645 | A646 | A647 | A648 | |
| A649 | A650 | A651 | A652 | A653 | A654 | A655 | A656 | A657 | A658 | A659 | A660 |
| A661 | A662 | A663 | A664 | A665 | A666 | A667 | A668 | A669 | A670 | A671 | A672 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | — | — | — | — | — | — |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 8

Compounds of the formula Ip:

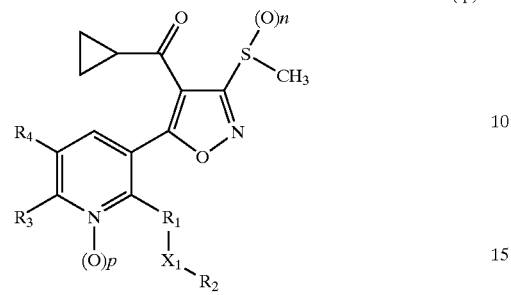

(Ip)

in which $R_1$, $R_2$, $R_3$, $R_4$, $X_1$ and p have the same meaning as given for the radical A, and n is 0,1 or 2:

| A | A | A | A | A | A | A | A | A | A | A | A |
|---|---|---|---|---|---|---|---|---|---|---|---|
| — | — | — | — | — | — | — | A8 | A9 | A10 | A11 | A12 |
| A13 | A14 | A15 | A16 | A17 | A18 | A19 | A20 | A21 | A22 | A23 | A24 |
| A25 | A26 | A27 | A28 | A29 | A30 | A31 | A32 | A33 | A34 | A35 | A36 |
| A37 | A38 | A39 | A40 | A41 | A42 | A43 | A44 | A45 | A46 | A47 | A48 |
| A49 | A50 | A51 | A52 | A53 | A54 | A55 | A56 | A57 | A58 | A59 | A60 |
| A61 | A62 | A63 | A64 | A65 | A66 | A67 | A68 | A69 | A70 | A71 | A72 |
| A73 | A74 | A75 | A76 | A77 | A78 | A79 | A80 | A81 | A82 | A83 | A84 |
| A85 | A86 | A87 | A88 | A89 | A90 | — | — | — | — | — | — |
| — | — | A99 | A100 | A101 | A102 | A103 | A104 | A105 | A106 | A107 | A108 |
| A109 | A110 | A111 | A112 | A113 | A114 | A115 | A116 | A117 | A118 | A119 | A120 |
| A121 | A122 | A123 | A124 | A125 | A126 | A127 | A128 | A129 | A130 | A131 | A132 |
| A133 | A134 | A135 | A136 | A137 | A138 | A139 | A140 | A141 | A142 | A143 | A144 |
| A145 | A146 | A147 | A148 | A149 | A150 | A151 | A152 | A153 | A154 | A155 | A156 |
| A157 | A158 | A159 | A160 | A161 | A162 | A163 | A164 | A165 | A166 | A167 | A168 |
| A169 | A170 | A171 | A172 | A173 | A174 | A175 | A176 | A177 | A178 | A179 | A180 |
| A181 | A182 | A183 | A184 | A185 | A186 | A187 | A188 | A189 | A190 | A191 | A192 |
| A193 | A194 | A195 | A196 | A197 | A198 | A199 | A200 | A201 | A202 | A203 | A204 |
| A205 | A206 | A207 | A208 | A209 | A210 | A211 | A212 | A213 | A214 | A215 | A216 |
| A217 | A218 | A219 | A220 | A221 | A222 | A223 | A224 | A225 | A226 | A227 | A228 |
| A229 | A230 | A231 | A232 | A233 | A234 | A235 | A236 | A237 | A238 | A239 | A240 |
| A241 | A242 | A243 | A244 | A245 | A246 | A247 | A248 | A249 | A250 | A251 | A252 |
| A253 | A254 | A255 | A256 | A257 | A258 | A259 | A260 | A261 | A262 | A263 | A264 |
| A265 | A266 | A267 | A268 | A269 | A270 | A271 | A272 | A273 | A274 | A275 | A276 |
| A277 | A278 | A279 | A280 | A281 | A282 | A283 | A284 | A285 | A286 | A287 | A288 |
| A289 | A290 | A291 | A292 | A293 | A294 | A295 | A296 | A297 | A298 | A299 | A300 |
| A301 | A302 | A303 | A304 | A305 | A306 | A307 | A308 | A309 | A310 | A311 | A312 |
| A313 | A314 | A315 | A316 | A317 | A318 | A319 | A320 | A321 | A322 | A323 | A324 |
| A325 | A326 | A327 | A328 | A329 | A330 | A331 | A332 | A333 | A334 | A335 | A336 |
| A337 | A338 | A339 | A340 | A341 | A342 | A343 | A344 | A345 | A346 | A347 | A348 |
| A349 | A350 | A351 | A352 | A353 | A354 | A355 | A356 | A357 | A358 | A359 | A360 |
| A361 | A362 | A363 | A364 | A365 | A366 | A367 | A368 | A369 | A370 | A371 | A372 |
| A373 | A374 | A375 | A376 | A377 | A378 | A379 | A380 | A381 | A382 | A383 | A384 |
| A385 | A386 | A387 | A388 | A389 | A390 | A391 | A392 | A393 | A394 | A395 | A396 |
| A397 | A398 | A399 | A400 | A401 | A402 | A403 | A404 | A405 | A406 | A407 | A408 |
| A409 | A410 | A411 | A412 | A413 | A414 | A415 | A416 | A417 | A418 | A419 | A420 |
| A421 | A422 | A423 | A424 | A425 | A426 | A427 | A428 | A429 | A430 | A431 | A432 |
| A433 | A434 | A435 | A436 | A437 | A438 | A439 | A440 | A441 | A442 | A443 | A444 |
| A445 | A446 | A447 | A448 | A449 | A450 | A451 | A452 | A453 | A454 | A455 | A456 |
| A457 | A458 | A459 | A460 | A461 | A462 | A463 | A464 | A465 | A466 | A467 | A468 |
| A469 | A470 | A471 | A472 | A473 | A474 | A475 | A476 | A477 | A478 | A479 | A480 |
| A481 | A482 | A483 | A484 | A485 | A486 | A487 | A488 | A489 | A490 | A491 | A492 |
| A493 | A494 | A495 | A496 | A497 | A498 | A499 | A500 | A501 | A502 | A503 | A504 |
| A505 | A506 | A507 | A508 | A509 | A510 | A511 | A512 | A513 | A514 | A515 | A516 |
| A517 | A518 | A519 | A520 | A521 | A522 | A523 | A524 | A525 | A526 | A527 | A528 |
| A529 | A530 | A531 | A532 | A533 | A534 | A535 | A536 | A537 | A538 | A539 | A540 |
| A541 | A542 | A543 | A544 | A545 | — | — | — | — | — | — | — |
| — | A554 | A555 | A556 | A557 | A558 | A559 | A560 | A561 | A562 | A563 | A564 |
| A565 | A566 | A567 | A568 | A569 | A570 | A571 | A572 | A573 | A574 | A575 | A576 |
| A577 | A578 | A579 | A580 | A581 | A582 | A583 | A584 | A585 | A586 | A587 | A588 |
| A589 | A590 | A591 | A592 | A593 | A594 | A595 | A596 | A597 | A598 | A599 | A600 |
| A601 | A602 | A603 | A604 | A605 | A606 | A607 | A608 | A609 | A610 | A611 | A612 |

-continued

| A | A | A | A | A | A | A | A | A | A | A | A |
|---|---|---|---|---|---|---|---|---|---|---|---|
| A613 | A614 | A615 | A616 | A617 | A618 | A619 | A620 | A621 | A622 | A623 | A624 |
| A625 | A626 | A627 | A628 | A629 | A630 | A631 | A632 | A633 | A634 | A635 | A636 |
| — | — | — | — | — | — | — | A644 | A645 | A646 | A647 | A648 |
| A649 | A650 | A651 | A652 | A653 | A654 | A655 | A656 | A657 | A658 | A659 | A660 |
| A661 | A662 | A663 | A664 | A665 | A666 | A667 | A668 | A669 | A670 | A671 | A672 |
| A685 | A686 | A687 | A688 | A689 | A690 | A691 | A692 | A693 | A694 | A695 | A696 |
| A697 | A698 | A699 | A700 | A701 | A702 | A703 | A704 | A705 | A706 | A707 | A708 |
| A709 | A710 | A711 | A712 | A713 | A714 | A715 | A716 | A717 | A718 | A719 | A720 |
| A721 | A722 | A723 | A724 | A725 | A726 | — | — | — | — | — | — |
| A733 | A734 | A735 | A736 | A737 | A738 | A739 | A740 | A741 | A742 | A743 | A744 |
| A745 | A746 | A747 | A748 | A749 | A750 | A751 | A752 | A753 | A754 | A755 | A756 |
| A757 | A758 | A759 | A760 | A761 | A762 | A763 | A764 | A765 | A766 | A767 | A768 |
| A769 | A770 | A771 | A772 | A773 | A774 | A775 | A776 | A777 | A778 | A779 | A780 |
| A781 | A782 | A783 | A784 | A785 | A786 | A787 | A788 | A789 | A790 | A791 | A792 |
| A793 | A794 | A795 | A796 | A797 | A798 | A799 | A800 | A801 | A802 | A803 | A804 |
| A805 | A806 | A807 | A808 | A809 | A810 | A811 | A812 | A813 | A814 | A815 | A816 |
| A817 | A818 | A819 | A820 | A821 | A822 | A823 | A824 | A825 | A826 | A827 | A828 |
| A829 | A830 | A831 | A832 | — | — | — | — | — | — | — | — |

TABLE 9

Compounds of the formula I, represented as compounds of the formula
A—Q
in which A denotes A10:

| A10 | A10 | A10 | A10 | A10 | A10 | A10 | A10 | A10 | A10 | A10 | A10 |
|---|---|---|---|---|---|---|---|---|---|---|---|
| B1 | B2 | — | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | — | B40 | B41 | B42 | B43 | B44 | B45 | B46 | B47 | B48 |
| B49 | B50 | B51 | — | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 | | B96 |
| B97 | B98 | B99 | B100 | B101 | B102 | B103 | B104 | B105 | B106 | B107 | B108 |
| B109 | B110 | — | — | — | — | — | — | — | — | — | — |

TABLE 10

Compounds of the formula I, represented as compounds of the formula
A—Q
in which A denotes A10:

| A10 | A10 | A10 | A10 | A10 | A10 | A10 | A10 | A10 | A10 | A10 | A10 |
|---|---|---|---|---|---|---|---|---|---|---|---|
| C1 | — | C3 | C4 | — | C6 | C7 | C8 | C9 | C10 | C11 | C12 |
| C13 | C14 | C15 | C16 | C17 | C18 | C19 | C20 | C21 | C22 | C23 | C24 |
| C25 | C26 | C27 | — | — | — | — | — | — | — | — | — |

TABLE 11

Compounds of the formula I, represented as compounds of the formula
A—Q
in which A denotes A10:

| A10 | A10 | A10 | A10 | A10 | A10 | A10 | A10 | A10 | A10 | A10 | A10 |
|---|---|---|---|---|---|---|---|---|---|---|---|
| — | — | — | D4 | D5 | D6 | D7 | D8 | D9 | D10 | D11 | D12 |

TABLE 12

Compounds of the formula I, represented as compounds of the formula
A—Q
in which A denotes A556:

| A556 | A556 | A556 | A556 | A556 | A556 | A556 | A556 | A556 | A556 | A556 | A556 |
|---|---|---|---|---|---|---|---|---|---|---|---|
| B1 | B2 | — | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | — | B40 | B41 | B42 | B43 | B44 | B45 | B46 | B47 | B48 |
| B49 | B50 | B51 | — | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 |  | B96 |
| B97 | B98 | B99 | B100 | B101 | B102 | B103 | B104 | B105 | B106 | B107 | B108 |
| B109 | B110 | — | — | — | — | — | — | — | — | — | — |

TABLE 13

Compounds of the formula I, represented as compounds of the formula
A—Q
in which A denotes A556:

| A556 | A556 | A556 | A556 | A556 | A556 | A556 | A556 | A556 | A556 | A556 | A556 |
|---|---|---|---|---|---|---|---|---|---|---|---|
| C1 | — | C3 | C4 | — | C6 | C7 | C8 | C9 | C10 | C11 | C12 |
| C13 | C14 | C15 | C16 | C17 | C18 | C19 | C20 | C21 | C22 | C23 | C24 |
| C25 | C26 | C27 | — | — | — | — | — | — | — | — | — |

TABLE 14

Compounds of the formula I, represented as compounds of the formula
A—Q
in which A denotes A556:

| A556 | A556 | A556 | A556 | A556 | A556 | A556 | A556 | A556 | A556 | A556 | A556 |
|---|---|---|---|---|---|---|---|---|---|---|---|
| — | — | — | D4 | D5 | D6 | D7 | D8 | D9 | D10 | D11 | D12 |

TABLE 15

Compounds of the formula I, represented as compounds of the formula
A—Q
in which A denotes A646:

| A646 | A646 | A646 | A646 | A646 | A646 | A646 | A646 | A646 | A646 | A646 | A646 |
|---|---|---|---|---|---|---|---|---|---|---|---|
| B1 | B2 | — | B4 | B5 | B6 | B7 | B8 | B9 | B10 | B11 | B12 |
| B13 | B14 | B15 | B16 | B17 | B18 | B19 | B20 | B21 | B22 | B23 | B24 |
| B25 | B26 | B27 | B28 | B29 | B30 | B31 | B32 | B33 | B34 | B35 | B36 |
| B37 | B38 | — | B40 | B41 | B42 | B43 | B44 | B45 | B46 | B47 | B48 |
| B49 | B50 | B51 | — | B53 | B54 | B55 | B56 | B57 | B58 | B59 | B60 |
| B61 | B62 | B63 | B64 | B65 | B66 | B67 | B68 | B69 | B70 | B71 | B72 |
| B73 | B74 | B75 | B76 | B77 | B78 | B79 | B80 | B81 | B82 | B83 | B84 |
| B85 | B86 | B87 | B88 | B89 | B90 | B91 | B92 | B93 | B94 |  | B96 |
| B97 | B98 | B99 | B100 | B101 | B102 | B103 | B104 | B105 | B106 | B107 | B108 |
| B109 | B110 | — | — | — | — | — | — | — | — | — | — |

TABLE 16

Compounds of the formula I, represented as compounds of the formula
A—Q
in which A denotes A646:

| A646 | A646 | A646 | A646 | A646 | A646 | A646 | A646 | A646 | A646 | A646 | A646 |
|---|---|---|---|---|---|---|---|---|---|---|---|
| C1 | — | C3 | C4 | — | C6 | C7 | C8 | C9 | C10 | C11 | C12 |
| C13 | C14 | C15 | C16 | C17 | C18 | C19 | C20 | C21 | C22 | C23 | C24 |
| C25 | C26 | C27 | — | — | — | — | — | — | — | — | — |

TABLE 17

Compounds of the formula I, represented as compounds of the formula
A—Q
in which A denotes A646:

| A646 | A646 | A646 | A646 | A646 | A646 | A646 | A646 | A646 | A646 | A646 | A646 |
|------|------|------|------|------|------|------|------|------|------|------|------|
| —    | —    | —    | D4   | D5   | D6   | D7   | D8   | D9   | D10  | D11  | D12  |

TABLE 18

Physical data for the compounds of the formula I given in the tables above: (the melting points are given in °C.)

| Compound | m.p. (range) | Phys. state |
|----------|--------------|-------------|
| A1-C2 | 138–140 | crystalline |
| A2-C2 | 138–140 | crystalline |
| A833-B52 (K$^+$) | 145–150 | crystalline |
| A833-B52 (H4) | — | oil |
| A830-B52 | — | amorphous/liquid |
| A829-B52 | — | oil |
| A829-B1 | — | oil |
| A10-B52 (H3) | 54–56 | crystalline |
| A10-B1 | 71–73 | crystalline |
| A10-B3 | — | viscous |
| A10-B14 | — | viscous |
| A10-B39 | 99–100 | crystalline |
| A736-B52 | 100–102 | crystalline |
| A10-C2 (H6) | — | viscous |
| A57-B52 (H5) | 54–56 | crystalline |
| A18-B52 | 71–74 | crystalline |
| A8-B52 | 95–98 | crystalline |
| A19-B52 | 53–55 | crystalline |
| A1-C5 | 32–34 | crystallıne |
| A2-C5 | 32–33 | crystalline |
| A10-C5 | — | resin |
| A11-C5 | 38–39 | crystalline |
| A11-B52 | — | resin |
| A834-B52 | — | crystalline |
| A835-B52 | — | viscous |
| A854-B52 | — | viscous |
| A90-B52 | — | viscous |
| A33-B52 | 113–115 | crystalline |
| A556-B52 | — | crystalline |
| A646-B52 | — | viscous |
| A868-B52 | 106–107 | crystalline |
| A855-B52 | — | viscous |
| A817-B52 | — | viscous |
| A819-B52 | — | crystalline |
| A856-B52 | — | solid |
| A857-B52 | — | viscous |
| A63-B52 | — | resin |
| A20-B52 | — | solid |
| A858-B52 | — | resin |
| A836-B52 | — | crystalline |
| A859-B52 | — | viscous |
| A818-B52 | — | viscous |
| A837-B52 | — | viscous |
| A28-B52 | — | viscous |
| A28-B52 (Et$_3$NH$^+$) | — | crystalline |
| A838-B52 | — | viscous |
| A839-B52 | — | viscous |
| A860-B52 | — | viscous |
| A860-B113 | — | viscous |
| A861-B52 | 90–93 | crystalline |
| A840-B52 | — | oil |
| A841-B52 | 41–43 | crystalline |
| A842-B52 | — | viscous |
| A843-B52 | — | viscous |
| A866-B100 | 96–98 | crystalline |
| A844-B52 | — | viscous |
| A866-B112 | — | viscous |
| A867-B112 | — | viscous |
| A856-B112 | 79–81 | crystalline |
| A20-C5 | — | viscous |
| A10-C28 | — | resin |
| A11-C28 | — | resin |
| A10-B52 (Et$_3$NH$^+$) | — | viscous |
| A862-B52 | — | viscous |
| A24-B52 | 102–105 | crystalline |
| A845-B52 | 40–44 | crystalline |
| A837-B52 (Et$_3$NH$^+$) | — | viscous |
| A67-B52 | 68–69 | crystalline |
| A863-B52 | 80–80 | crystalline |
| A10-B17 | 40–42 | crystalline |
| A846-B52 | — | crystalline |
| A847-B52 | — | viscous |
| A848-B52 | — | crystalline |
| A56-B52 | — | vitreous |
| A26-B52 | — | vitreous |
| A849-B52 | — | viscous |
| A10-B4 | — | viscous |
| A865-B52 | — | viscous |
| A850-B52 | 63–64 | crystalline |
| A10-C29 | — | resin |
| A10-B111 | 76–78 | crystalline |
| A3-C5 | — | resin |
| A834-C5 | — | resin |
| A851-B52 | — | vitreous |
| A852-B52 | — | viscous |
| A10-B25 | — | amorphous/liquid |
| A853-B52 | — | viscous |
| A27-B52 | — | oil |
| A864-C5 | 149–150 | crystalline |
| A864-B52 | 110–112 | crystalline |
| A834-B39 | — | oil |
| A-852-OH | — | oil |
| A-851-OH | 102–103 | crystalline |
| A-835-OH | — | oil |
| A-24-OH | — | solid |
| A-858-OH | — | oil |
| A-859-OH | — | oil |
| A-864-OH | — | solid |
| A-851-OH | 73–74 | crystalline |
| A-848-OH | 81–82 | crystalline |
| A-27-OH | — | oil |
| A-855-OH | 102–104 | crystalline |
| A-90-OH | 111–114 | crystalline |
| A-124-OH | 117–119 | crystalline |
| A-834-OH | — | crystalline |
| A-852-OH | — | oil |
| A-851-OH | 102–103 | crystalline |
| A-835-OH | — | oil |
| A10-OH | 62–63 | crystalline |
| A830-OH | 157–158 | crystalline |
| A831-OH | 188–189 | crystalline |
| A829-OH | 131–134 | crystalline |
| A832-OH | 110–112 | crystalline |

Table 19: Physical data for the compound of the formula I given in the tables above: (the melting points given in °C.): In the following formulas, end-standing valences denote methyl groups (in all cases except alkyne or alkene groups) or hydrogen (in the case of alkyne or alkene groups), for example

TABLE 19

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

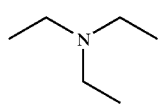   can be also drawn as   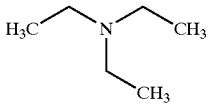   and

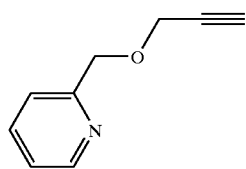   can be also drawn as   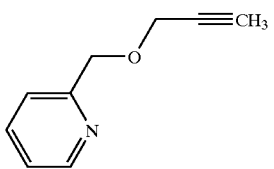

| Comp. No. | Corresponding Formula | m. p. (range) Phys. state |
|---|---|---|
| 1.001 | 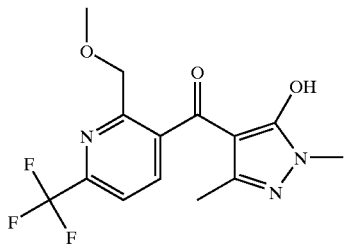 | 138–140 crystalline |
| 1.002 | 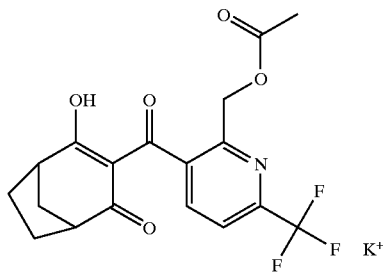 | 145–150 crystalline |
| 1.003 | 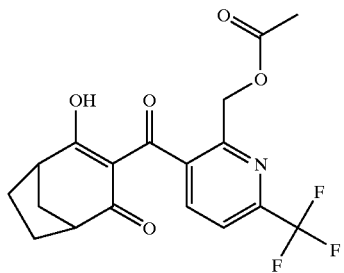 | oil |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

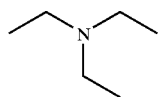   can be also drawn as   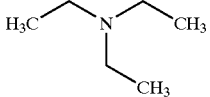   and

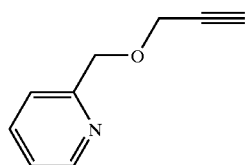   can be also drawn as   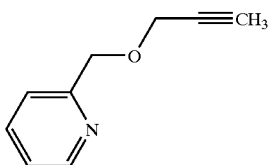

| Comp. No. | Corresponding Formula | m. p. (range) Phys. state |
|---|---|---|
| 1.004 | | oil |
| 1.005 | | oil |
| 1.006 | | oil |

TABLE 19-continued

Physical data for the compounds of the formula 1 given in the tables above:

(the melting points given in ° C.):

In the following formulas, end-standing valences denote methyl groups (in all cases except alkyne or alkene groups)

or hydrogen (in the case of alkyne or alkene groups), for example

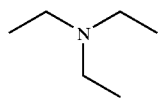 can be also drawn as 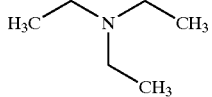 and

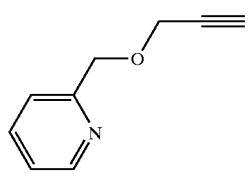 can be also drawn as 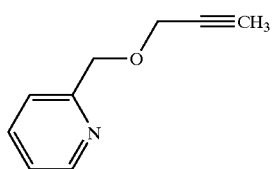

| Comp. No. | Corresponding Formula | m. p. (range) Phys. state |
|---|---|---|
| 1.007 | 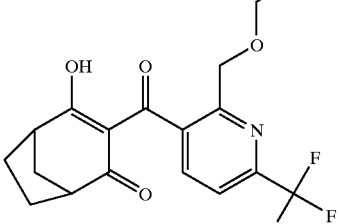 | 54–56 crystalline |
| 1.008 | 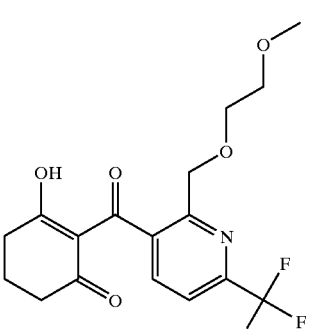 | crystalline |
| 1.009 | 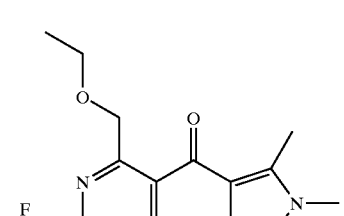 | viscous, 1H NMR; 1.82 (s); 3.26 (s); 3.37–3.39 (m); 3.57–3.60 (m); 3.71 (s); 4.84 (s); 7.74 (d); 7.82 (d) |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

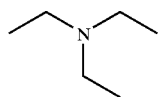 can be also drawn as 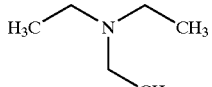 and

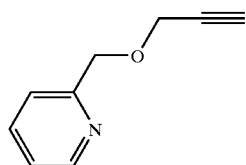 can be also drawn as 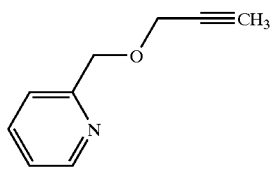

| Comp. No. | Corresponding Formula | m. p. (range) Phys. state |
|---|---|---|
| 1.010 | 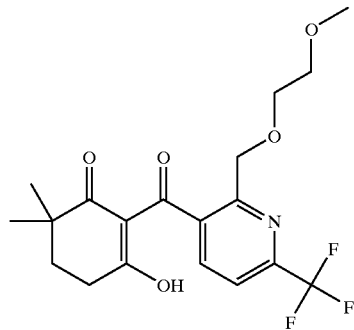 | viscous |
| 1.011 | 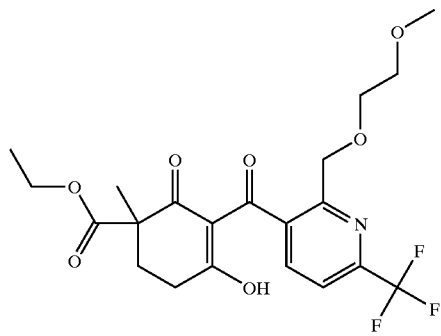 | viscous |
| 1.012 | 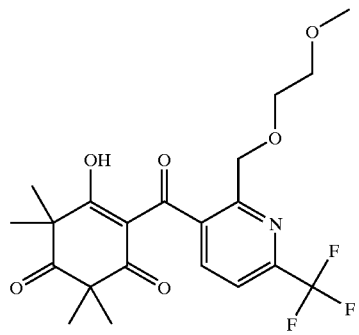 | 99–100 crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

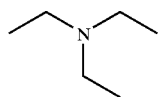   can be also drawn as   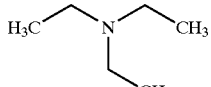   and

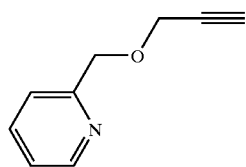   can be also drawn as   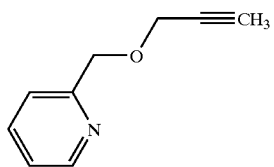

| Comp. No. | Corresponding Formula | m. p. (range) Phys. state |
|---|---|---|
| 1.013 | 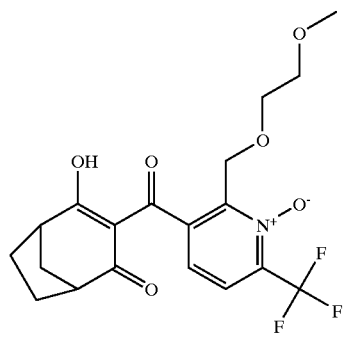 | 100–102 crystalline |
| 1.014 | 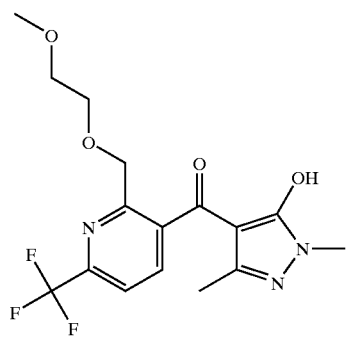 | viscous |
| 1.015 | 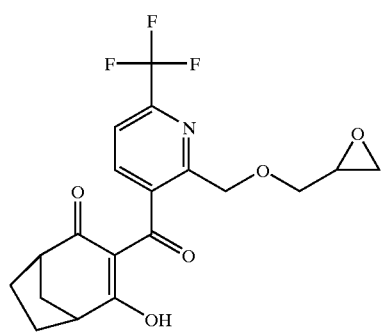 | 54–56 crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

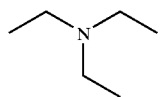 can be also drawn as 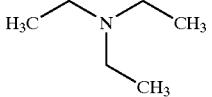 and

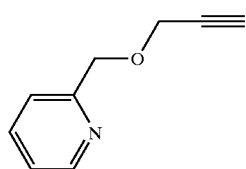 can be also drawn as 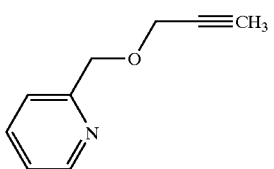

| Comp. No. | Corresponding Formula | m. p. (range) Phys. state |
|---|---|---|
| 1.016 | 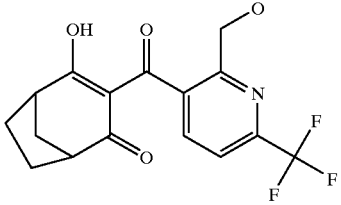 | 71–74 crystalline |
| 1.017 | 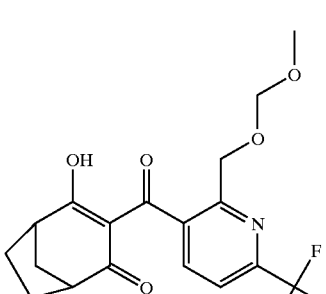 | 95–98 crystalline |
| 1.018 | 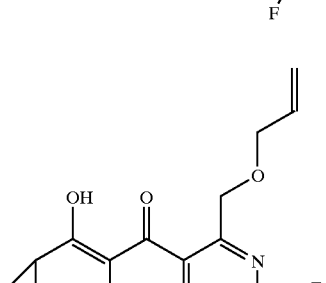 | 53–55 crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

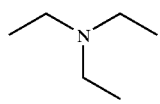     can be also drawn as     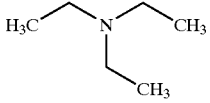     and

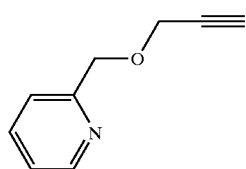     can be also drawn as     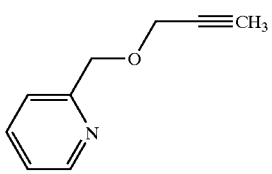

| Comp. No. | Corresponding Formula | m. p. (range) Phys. state |
|---|---|---|
| 1.019 | 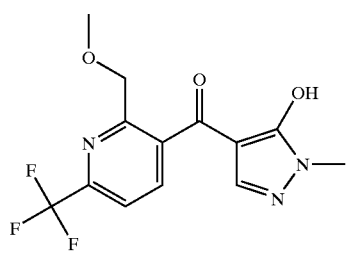 | 32–34 crystalline |
| 1.020 | 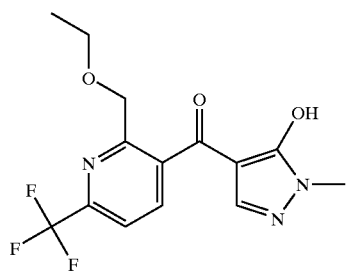 | 32–33 crystalline |
| 1.021 | 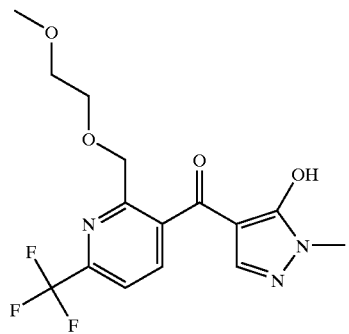 | resin |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

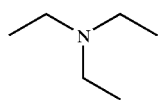  can be also drawn as  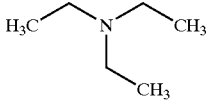  and

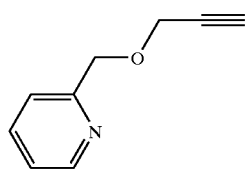  can be also drawn as  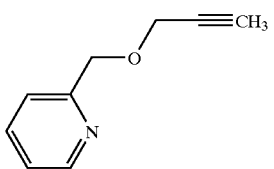

| Comp. No. | Corresponding Formula | m. p. (range) Phys. state |
|---|---|---|
| 1.022 | | 38–39 crystalline |
| 1.023 | | resin |
| 1.024 | | crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

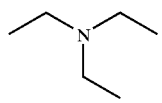   can be also drawn as   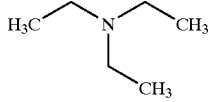   and

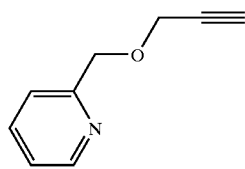   can be also drawn as   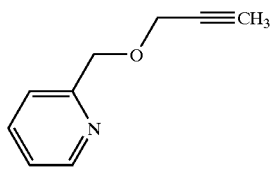

| Comp. No. | Corresponding Formula | m. p. (range) Phys. state |
|---|---|---|
| 1.025 | 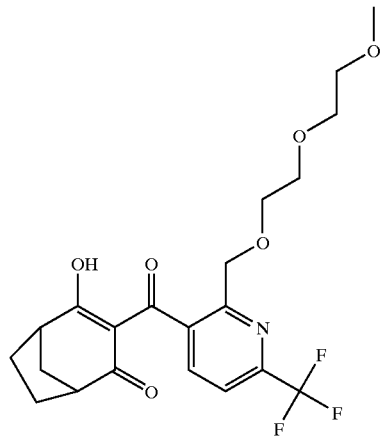 | viscous |
| 1.026 | 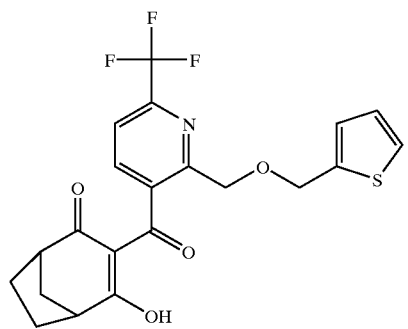 | viscous |
| 1.027 | 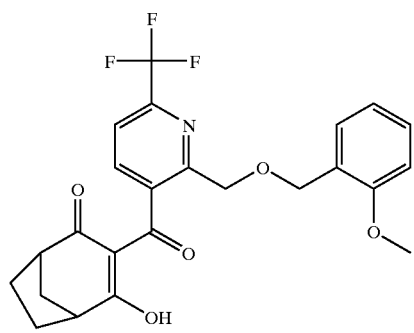 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

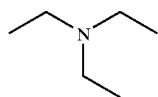 can be also drawn as 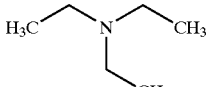 and

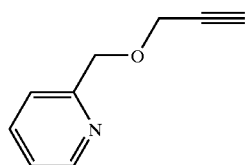 can be also drawn as 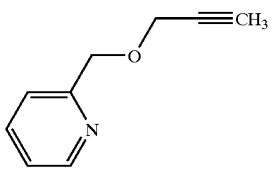

| Comp. No. | Corresponding Formula | m. p. (range) Phys. state |
|---|---|---|
| 1.028 | 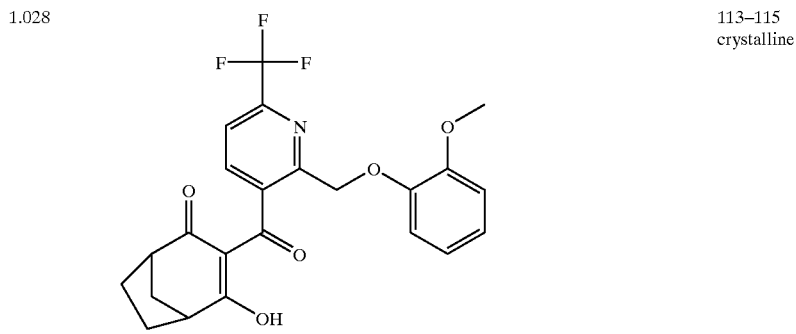 | 113–115 crystalline |
| 1.029 | 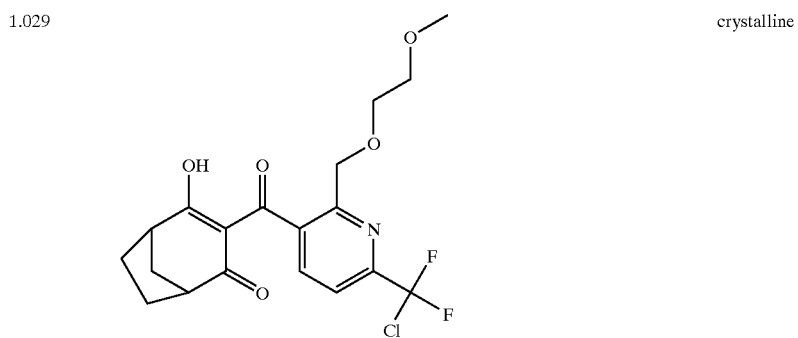 | crystalline |
| 1.030 | 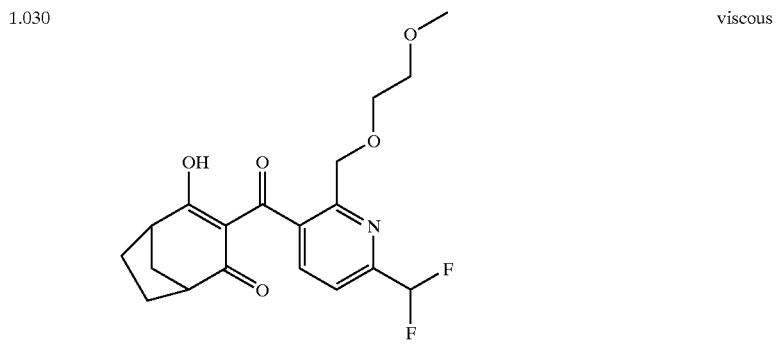 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

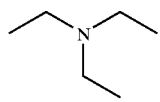 can be also drawn as 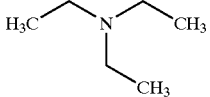 and

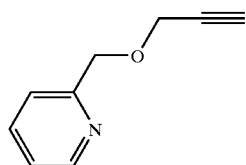 can be also drawn as 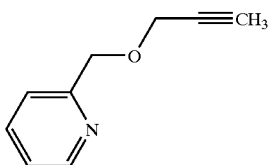

| Comp. No. | Corresponding Formula | m. p. (range) Phys. state |
|---|---|---|
| 1.031 | | 106–107 crystalline |
| 1.032 | | viscous |
| 1.033 | | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

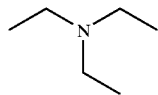   can be also drawn as   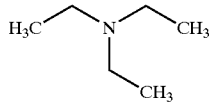   and

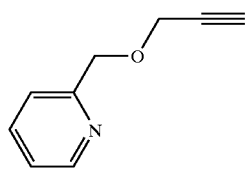   can be also drawn as   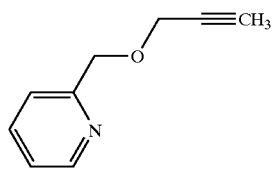

| Comp. No. | Corresponding Formula | m. p. (range) Phys. state |
|---|---|---|
| 1.034 | 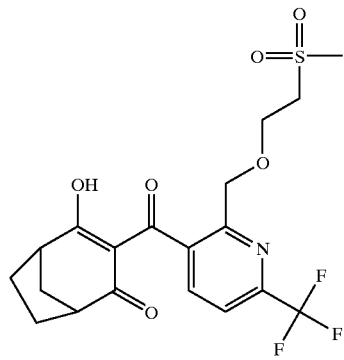 | crystalline |
| 1.035 | 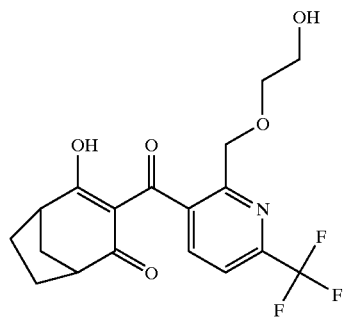 | crystalline |
| 1.036 | 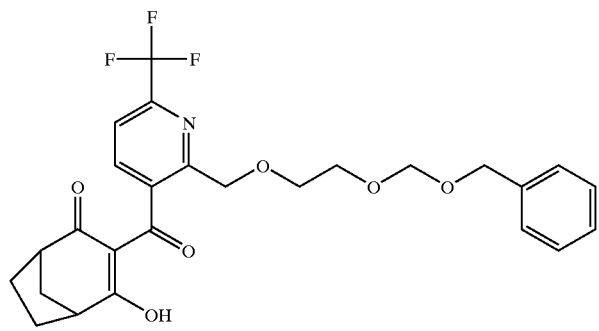 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

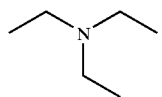   can be also drawn as   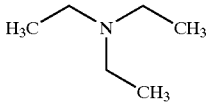   and

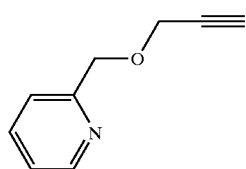   can be also drawn as   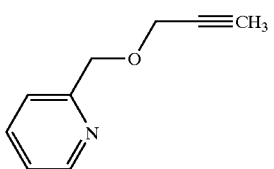

| Comp. No. | Corresponding Formula | m. p. (range) Phys. state |
|---|---|---|
| 1.037 | | resin |
| 1.038 | | solid |
| 1.039 | | resin |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

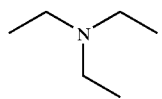 can be also drawn as 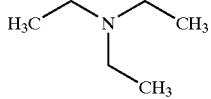 and

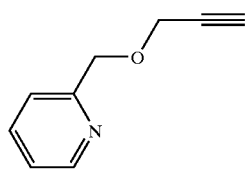 can be also drawn as 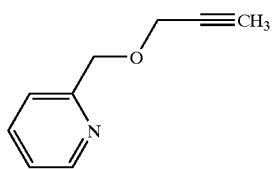

| Comp. No. | Corresponding Formula | m. p. (range) Phys. state |
|---|---|---|
| 1.040 | | crystalline |
| 1.041 | | viscous |
| 1.042 | | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

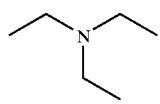   can be also drawn as   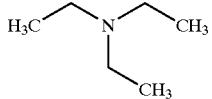   and

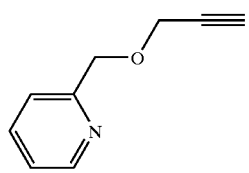   can be also drawn as   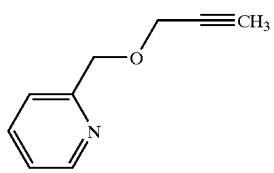

| Comp. No. | Corresponding Formula | m. p. (range) Phys. state |
|---|---|---|
| 1.043 | 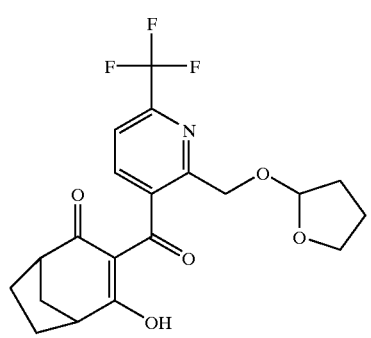 | viscous |
| 1.044 | 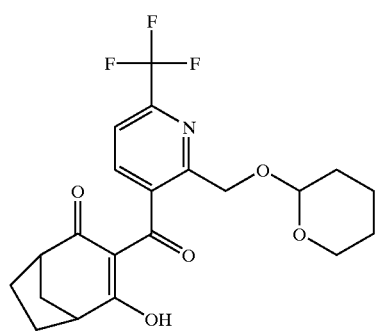 | viscous |
| 1.045 | 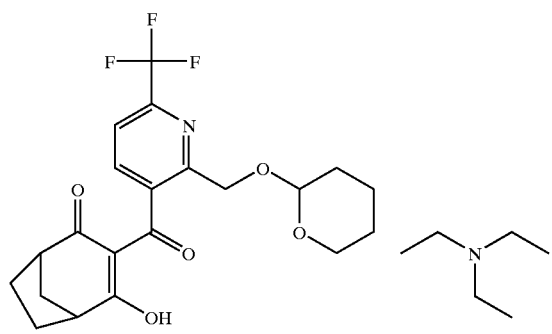 | crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

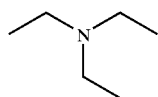   can be also drawn as   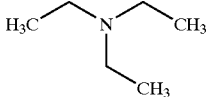   and

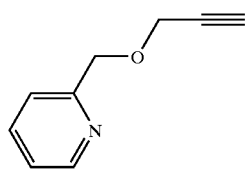   can be also drawn as   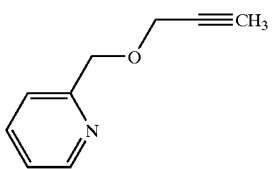

| Comp. No. | Corresponding Formula | m. p. (range) Phys. state |
|---|---|---|
| 1.046 | 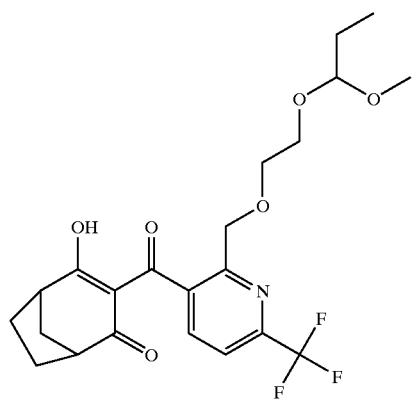 | viscous |
| 1.047 | 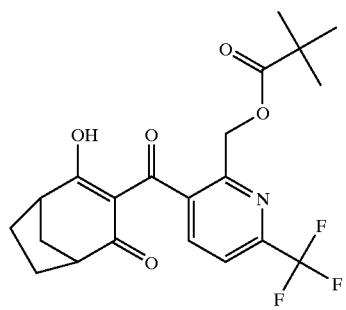 | viscous |
| 1.048 | 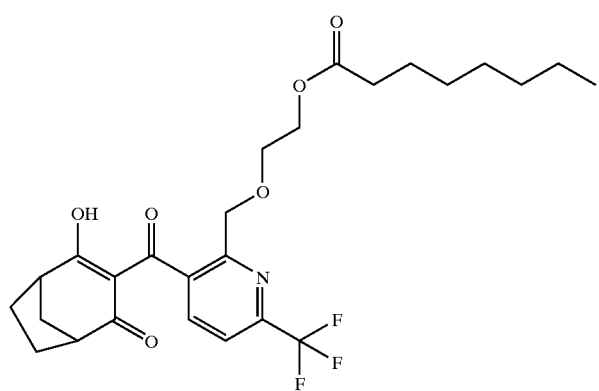 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

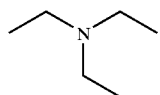   can be also drawn as   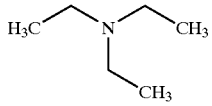   and

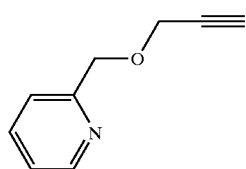   can be also drawn as   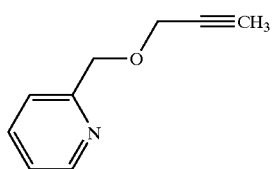

| Comp. No. | Corresponding Formula | m. p. (range) Phys. state |
|---|---|---|
| 1.049 | 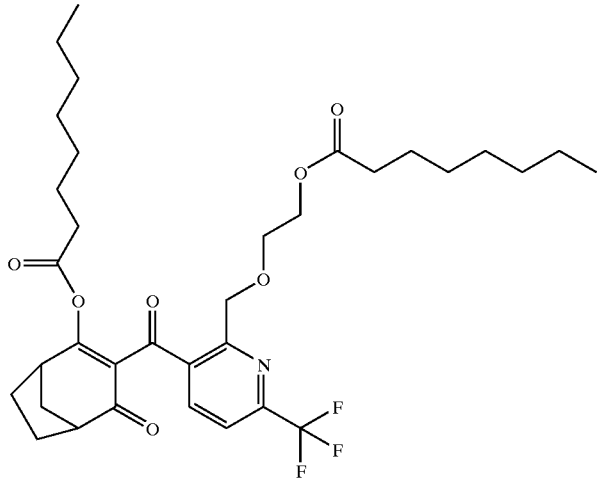 | viscous |
| 1.050 | 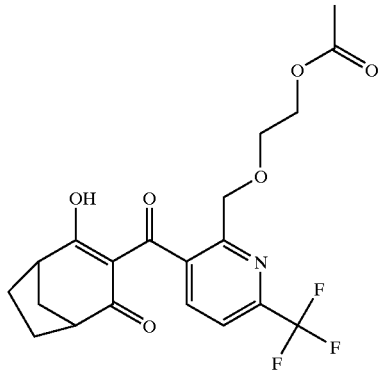 | 90–93 |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

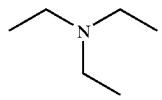  can be also drawn as  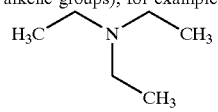  and

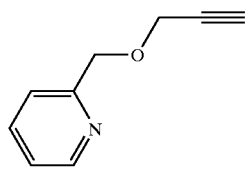  can be also drawn as  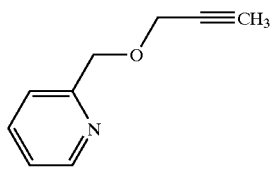

| Comp. No. | Corresponding Formula | m. p. (range) Phys. state |
|---|---|---|
| 1.051 | 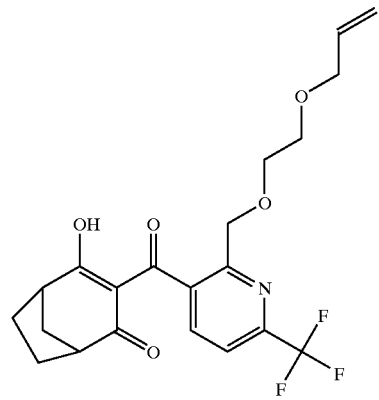 | oil |
| 1.052 | 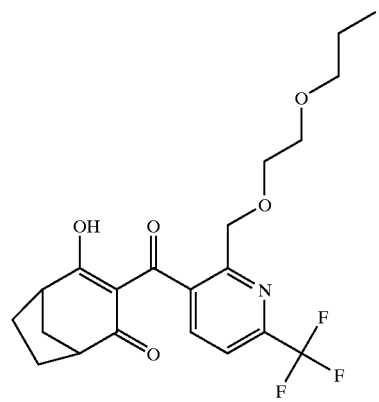 | 41–43 |
| 1.053 | 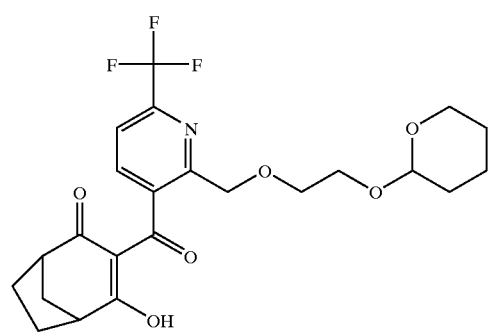 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

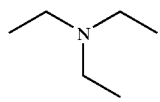  can be also drawn as  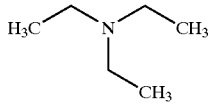  and

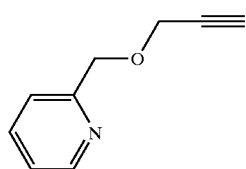  can be also drawn as  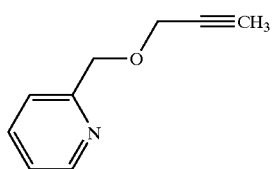

| Comp. No. | Corresponding Formula | m. p. (range) Phys. state |
|---|---|---|
| 1.054 | 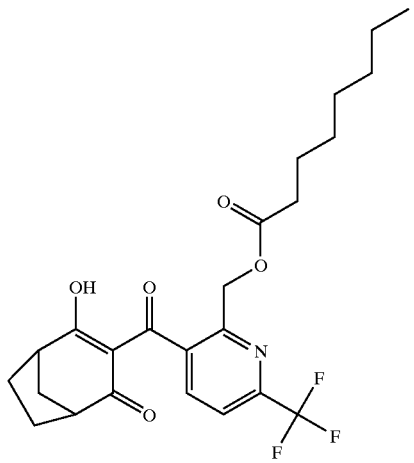 | viscous |
| 1.055 | 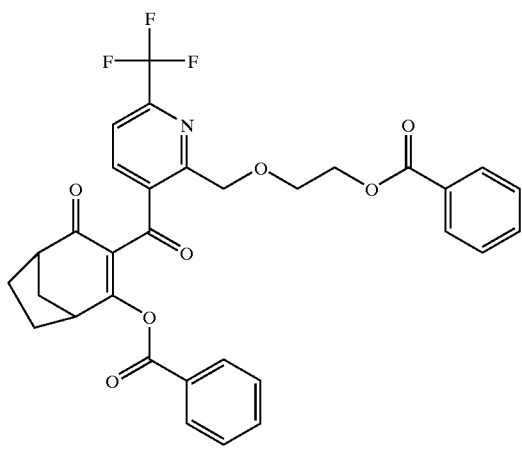 | 96–98 |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

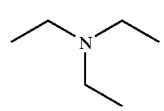 can be also drawn as 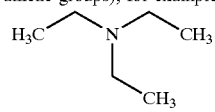 and

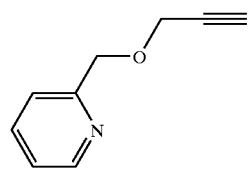 can be also drawn as 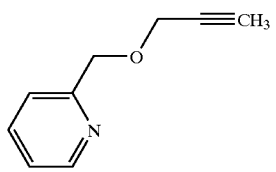

| Comp. No. | Corresponding Formula | m. p. (range) Phys. state |
|---|---|---|
| 1.056 | 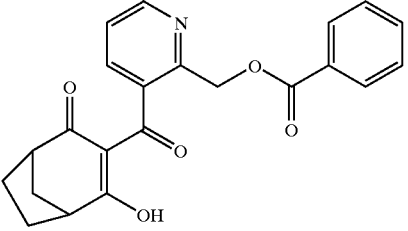 | viscous |
| 1.057 | 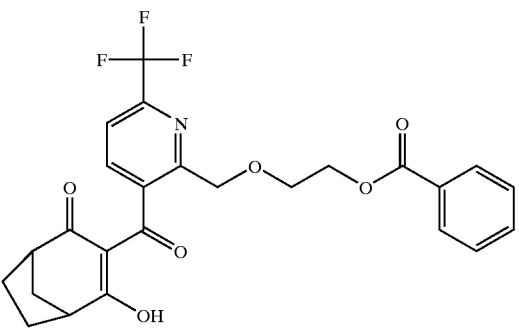 | viscous |
| 1.058 | 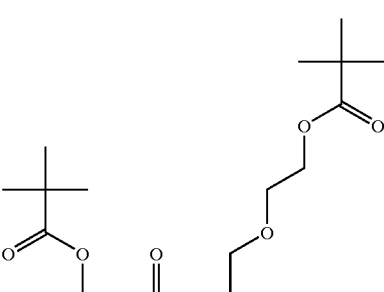 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

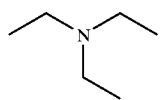  can be also drawn as  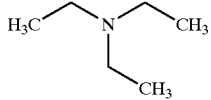  and

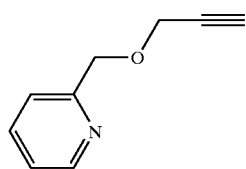  can be also drawn as  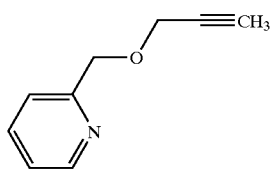

| Comp. No. | Corresponding Formula | m. p. (range) Phys. state |
|---|---|---|
| 1.059 | 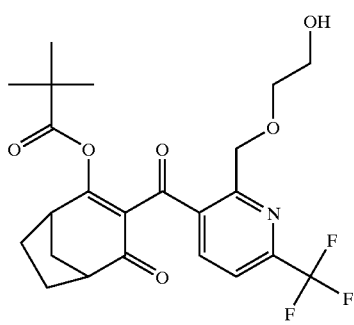 | 79–81 |
| 1.060 | 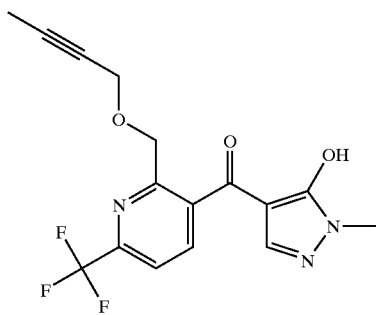 | viscous |
| 1.061 | 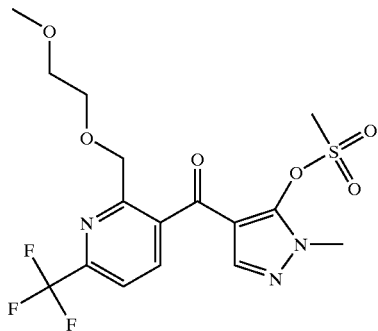 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

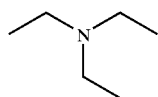   can be also drawn as   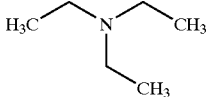   and

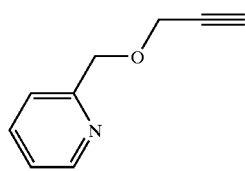   can be also drawn as   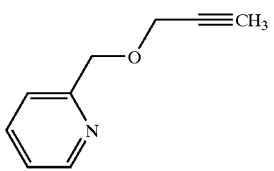

| Comp. No. | Corresponding Formula | m. p. (range) Phys. state |
|---|---|---|
| 1.062 | 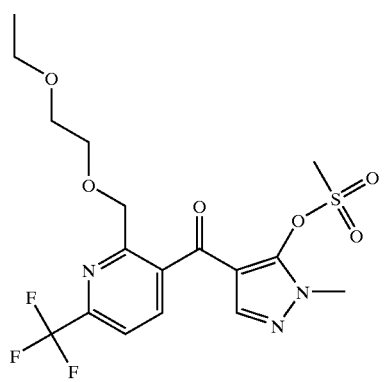 | resin |
| 1.063 | 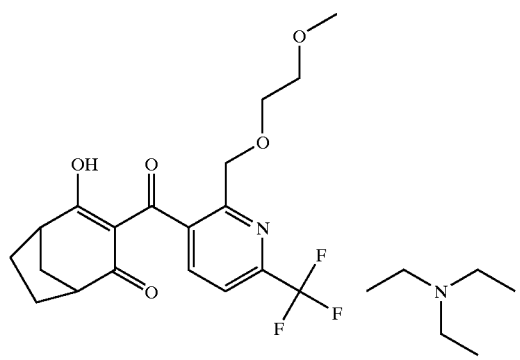 | crystalline |
| 1.064 | 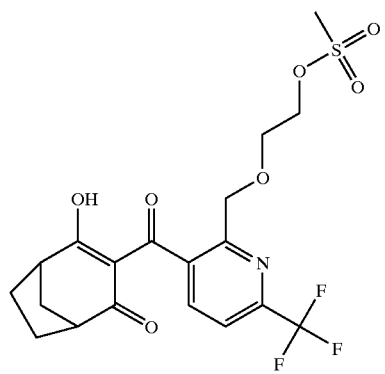 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

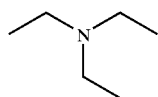 can be also drawn as 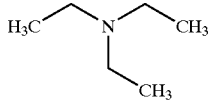 and

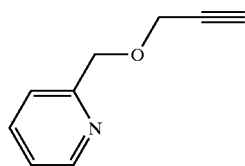 can be also drawn as 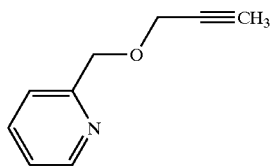

| Comp. No. | Corresponding Formula | m. p. (range) Phys. state |
|---|---|---|
| 1.065 | | 102–105 crystalline |
| 1.066 | | 40–44 crystalline |
| 1.067 | | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

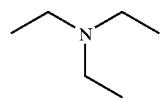   can be also drawn as   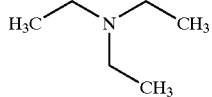   and

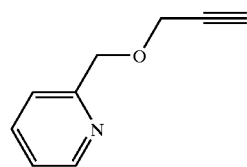   can be also drawn as   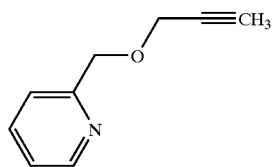

| Comp. No. | Corresponding Formula | m. p. (range) Phys. state |
|---|---|---|
| 1.068 | 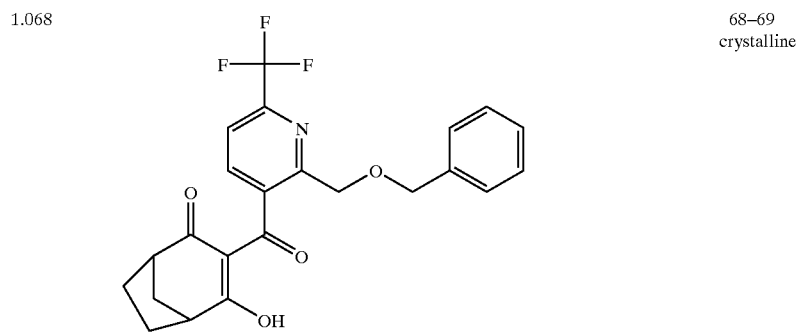 | 68–69 crystalline |
| 1.069 | 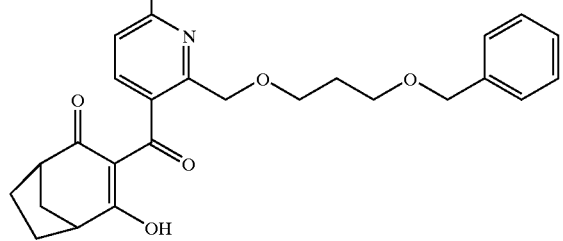 | 78–80 crystalline |
| 1.070 | 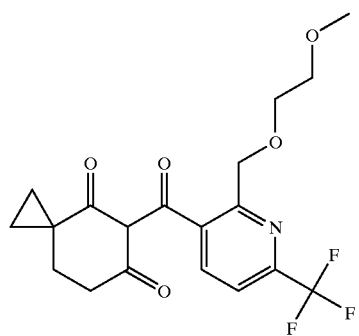 | 40–42 |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

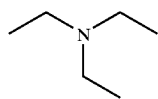   can be also drawn as   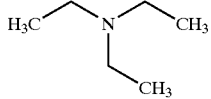   and

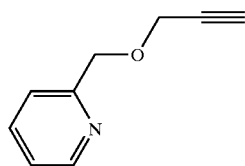   can be also drawn as   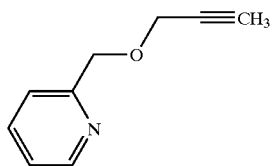

| Comp. No. | Corresponding Formula | m. p. (range) Phys. state |
|---|---|---|
| 1.071 | 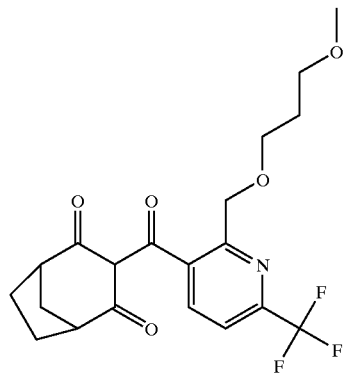 | crystalline |
| 1.072 | 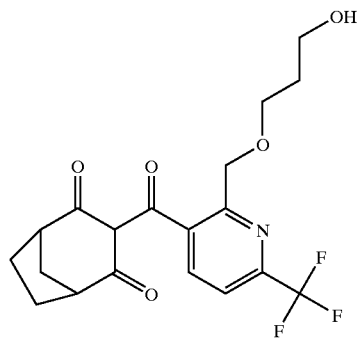 | viscous |
| 1.073 | 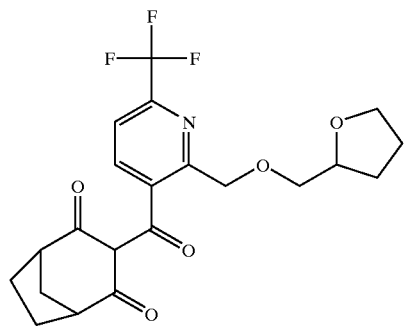 | 46–47 crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

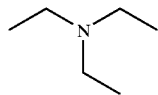   can be also drawn as   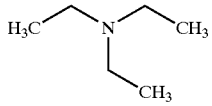   and

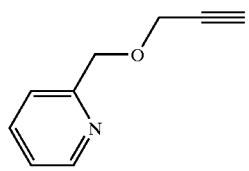   can be also drawn as   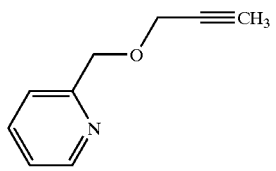

| Comp. No. | Corresponding Formula | m. p. (range) Phys. state |
|---|---|---|
| 1.074 | 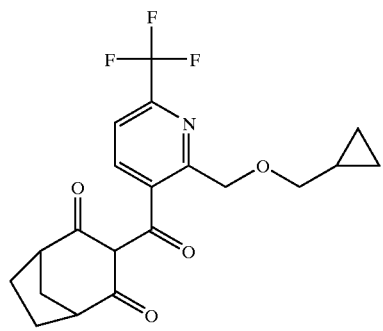 | vitreous |
| 1.075 | 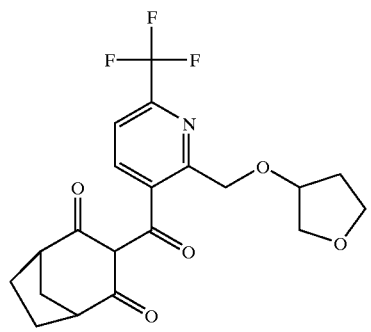 | vitreous |
| 1.076 | 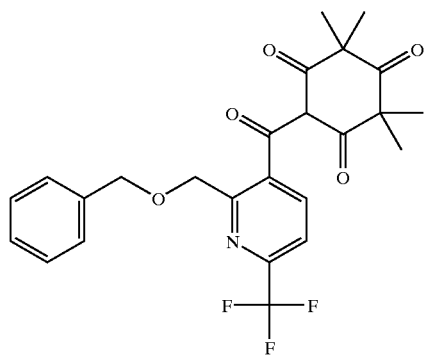 | 75–76 |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

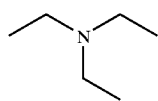     can be also drawn as     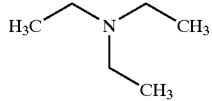     and

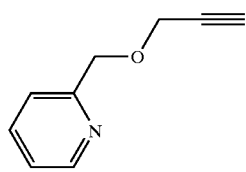     can be also drawn as     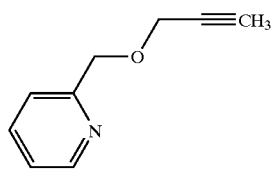

| Comp. No. | Corresponding Formula | m. p. (range) Phys. state |
|---|---|---|
| 1.077 | | viscous |
| 1.078 | | viscous |
| 1.079 | | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

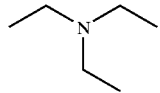 can be also drawn as 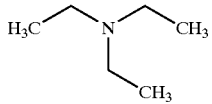 and

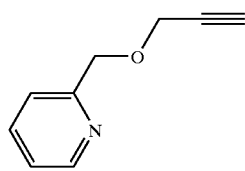 can be also drawn as 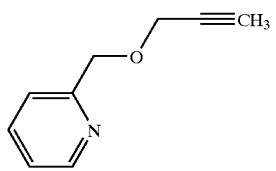

| Comp. No. | Corresponding Formula | m. p. (range) Phys. state |
|---|---|---|
| 1.080 | 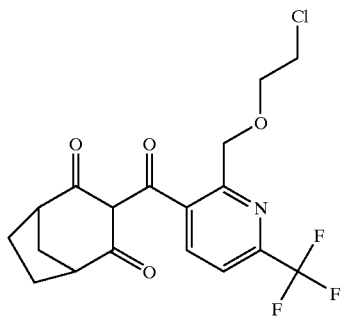 | 63–64 crystalline |
| 1.081 | 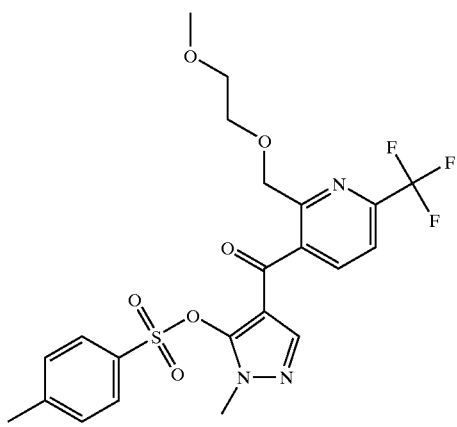 | resin |
| 1.082 | 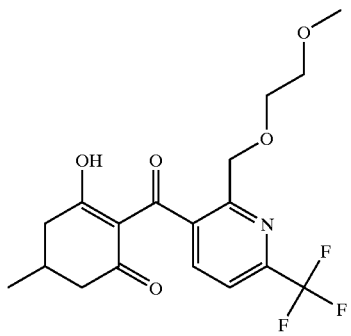 | 76–78 crystalline |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

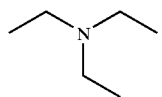   can be also drawn as   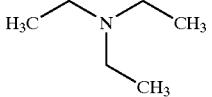   and

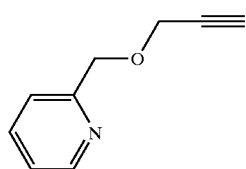   can be also drawn as   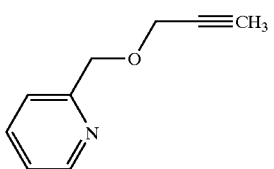

| Comp. No. | Corresponding Formula | m. p. (range) Phys. state |
|---|---|---|
| 1.083 | 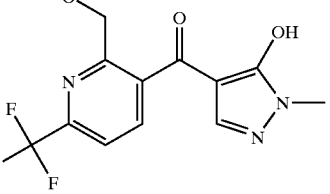 | resin |
| 1.084 | 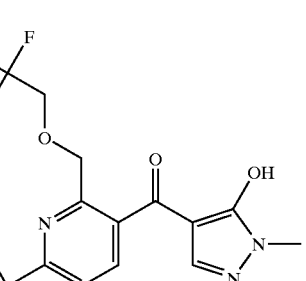 | resin |
| 1.085 | 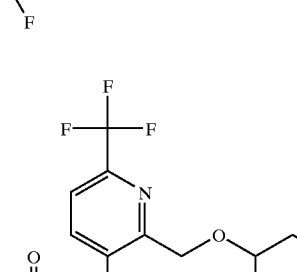 | vitreous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

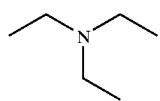 can be also drawn as 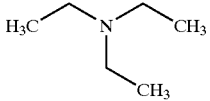 and

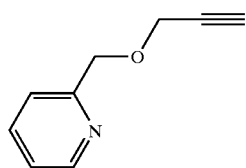 can be also drawn as 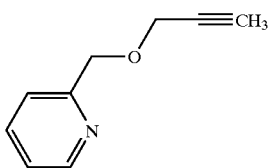

| Comp. No. | Corresponding Formula | m. p. (range) Phys. state |
|---|---|---|
| 1.086 | 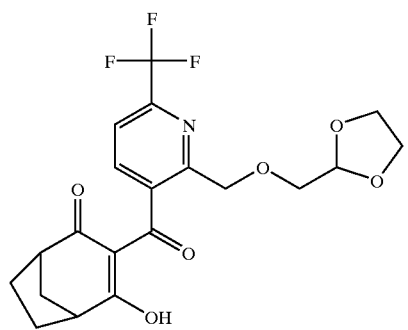 | viscous |
| 1.087 | 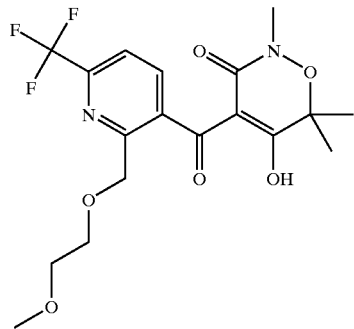 | oil |
| 1.088 | 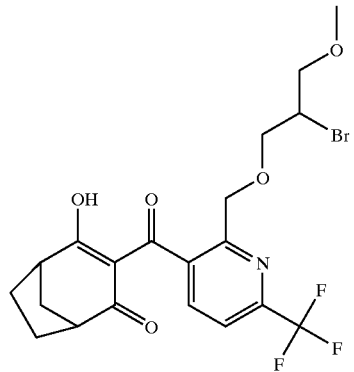 | viscous |

TABLE 19-continued

Physical data for the compounds of the formula 1 given in the tables above:
(the melting points given in ° C.):
In the following formulas, end-standing valences denote methyl groups
(in all cases except alkyne or alkene groups)
or hydrogen (in the case of alkyne or alkene groups), for example

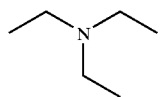   can be also drawn as   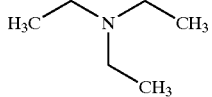   and

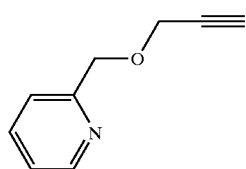   can be also drawn as   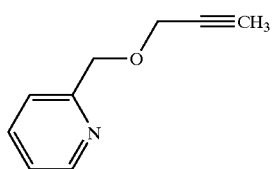

| Comp. No. | Corresponding Formula | m. p. (range) Phys. state |
|---|---|---|
| 1.089 | | oil |
| 1.090 | | 149–150 crystalline |
| 1.091 | | 110–112 crystalline |

TABLE 19-continued

Physical data for the compounds of the formula 1 given in the tables above:
(the melting points given in °C.):
In the following formulas, end-standing valences denote methyl groups
(in all cases except alkyne or alkene groups)
or hydrogen (in the case of alkyne or alkene groups), for example

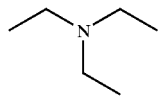 can be also drawn as 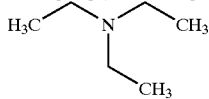 and

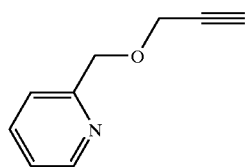 can be also drawn as 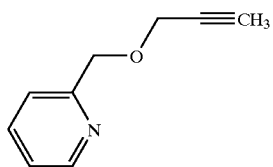

| Comp. No. | Corresponding Formula | m. p. (range) Phys. state |
|---|---|---|
| 1.092 | ![structure] | crystalline |

Biological Examples

Example B1

Herbicidal Action Before Emergence of the Plants (Pre-emergence Action)

Monocotyledonous and dicotyledonous test plants are sown in standard soil in pots. Immediately after sowing, the test substances are sprayed on at an optimum dosage (500 l of water/ha) as an aqueous suspension (prepared from a wettable powder (example F3, b) according to WO 97/34485) or emulsion (prepared from an emulsion concentrate (example F1, c) according to WO 97134485). The test plants are then grown under optimum conditions in a greenhouse.

After a test period of 4 weeks, the test is evaluated using a 9-level scale of ratings (1=complete damage, 9=no effect). Ratings of 1 to 4 (in particular 1 to 3) mean good to very good herbicidal action.

TABLE B1

Pre-emergence action: ("NT" means "not tested"):

| Compound | g/ha | Panicum | Digitaria | Echino. | Abutilon | Amarantnus | Chenop. |
|---|---|---|---|---|---|---|---|
| A10-B1 | 250 | 2 | 2 | 2 | 1 | 1 | 1 |
| A10-B52, (H3) | 250 | 1 | 1 | 1 | 1 | 1 | 1 |
| A830-B52 | 250 | 4 | 9 | 3 | 5 | 4 | 4 |
| A1-C2 | 250 | 6 | 3 | 3 | 4 | 3 | 1 |
| A833-B52 (K+) | 250 | 1 | 2 | 2 | 1 | 2 | 1 |
| A833-B52, (H4) | 250 | 1 | 1 | 1 | 1 | 1 | 1 |
| A10-B1 | 250 | 2 | 2 | 2 | 1 | 1 | 1 |
| A10-B3 | 250 | 1 | 1 | 1 | 1 | 1 | 1 |
| A10-B14 | 250 | 3 | 6 | 3 | 1 | 1 | 1 |
| A10-B39 | 250 | 1 | 1 | 1 | 1 | 1 | 1 |
| A736-B52 | 250 | 1 | 4 | 2 | 1 | 1 | 1 |
| A10-C2 (H6) | 250 | 3 | 3 | 3 | 1 | 2 | 1 |
| A57-B52 (H5) | 250 | 1 | 1 | 1 | 1 | 1 | 1 |
| A18-B52 | 250 | 1 | 1 | 1 | 2 | 2 | NT |
| A8-B52 | 250 | 1 | 1 | 1 | 1 | 1 | NT |
| A19-B52 | 250 | 1 | 1 | 1 | 1 | 2 | NT |
| A1-C5 | 250 | 2 | 2 | 1 | 2 | 2 | 1 |

TABLE B1-continued

Pre-emergence action: ("NT" means "not tested"):

| Compound | g/ha | Panicum | Digitaria | Echino. | Abutilon | Amarantnus | Chenop. |
|---|---|---|---|---|---|---|---|
| A2-C5 | 250 | 1 | 2 | 2 | 1 | 1 | 1 |
| A10-C5 | 250 | 2 | 3 | 1 | 1 | 1 | 1 |
| A11-C5 | 250 | 1 | 2 | 1 | 1 | 1 | 1 |
| A11-B52 | 250 | 1 | 1 | 1 | 1 | 2 | 1 |
| A834-B52 | 250 | 1 | 1 | 1 | 1 | 2 | 1 |
| A835-B52 | 250 | 1 | 2 | 1 | 2 | 1 | 2 |
| A556-B52 | 250 | 1 | 1 | 1 | 1 | 2 | 1 |
| A646-B52 | 250 | 1 | 1 | 1 | 1 | 2 | 1 |
| A819-B52 | 250 | 7 | 9 | 7 | 1 | 2 | 1 |
| A63-B52 | 250 | 2 | 3 | 1 | 5 | 3 | NT |
| A20-B52 | 250 | 1 | 1 | 1 | 3 | 3 | NT |
| A836-B52 | 250 | 1 | 2 | 1 | 5 | 2 | 3 |
| A837-B52 | 250 | 1 | 2 | 2 | 1 | 2 | NT |
| A28-B52 | 250 | 1 | 2 | 2 | 2 | 3 | NT |
| A28-B52 (Et3NH+) | 250 | 1 | 2 | 2 | 3 | 1 | NT |
| A838-B52 | 250 | 1 | 3 | 2 | 1 | 1 | 1 |
| A839-B52 | 250 | 1 | 3 | 2 | 1 | 1 | 1 |
| A840-B52 | 250 | 1 | 2 | 2 | 2 | 2 | 1 |
| A841-B52 | 250 | 1 | 2 | 1 | 1 | 1 | 1 |
| A842-B52 | 250 | 1 | 6 | 2 | 2 | 2 | 1 |
| A843-B52 | 250 | 1 | 2 | 2 | 1 | 1 | 1 |
| A844-B52 | 250 | 1 | 2 | 2 | 1 | 1 | 1 |
| A20-C5 | 250 | 1 | 2 | 2 | 1 | 1 | 1 |
| A10-C28 | 250 | 1 | 3 | 2 | 1 | 1 | 1 |
| A11-C28 | 250 | 2 | 2 | 1 | 2 | 1 | 1 |
| A10-B52 (Et3NH+) | 250 | 1 | 1 | 2 | 1 | 1 | 1 |
| A24-B52 | 250 | 1 | 1 | 1 | 1 | 1 | 1 |
| A845-B52 | 250 | 1 | 1 | 1 | 1 | 1 | 1 |
| A837-B52 (Et3NH+) | 250 | 1 | 1 | 2 | 1 | 1 | 1 |
| A67-B52 | 250 | 1 | 2 | 2 | 3 | 2 | 1 |
| A10-B17 | 250 | 1 | 1 | 1 | 4 | 2 | 1 |
| A846-B52 | 250 | 1 | 1 | 1 | 2 | 1 | 1 |
| A847-B52 | 250 | 1 | 3 | 2 | 4 | 1 | 4 |
| A848-B52 | 250 | 1 | 1 | 1 | 7 | 1 | 1 |
| A56-B52 | 250 | 1 | 2 | 1 | 3 | 1 | 1 |
| A26-B52 | 250 | 1 | 1 | 1 | 1 | 1 | 1 |
| A849-B52 | 250 | 1 | 2 | 2 | 2 | 1 | 1 |
| A10-B4 | 250 | 2 | 3 | 1 | 3 | 1 | 1 |
| A850-B52 | 250 | 1 | 2 | 1 | 1 | 2 | 1 |
| A10-C29 | 250 | 2 | 2 | 1 | 1 | 1 | NT |
| A10-B111 | 250 | 1 | 1 | 1 | 1 | 1 | NT |
| A3-C5 | 250 | 1 | 2 | 2 | 1 | 1 | NT |
| A834-C5 | 250 | 1 | 3 | 1 | 1 | 2 | NT |
| A851-B52 | 250 | 1 | 1 | 1 | 1 | 1 | 1 |
| A852-B52 | 250 | 1 | 1 | 1 | 4 | 1 | 2 |
| A10-B25 | 250 | 1 | 1 | 2 | 1 | 1 | 1 |
| A853-B52 | 250 | 1 | 1 | 2 | 1 | 1 | 2 |
| A27-B52 | 250 | 1 | 2 | 3 | 4 | 1 | 3 |

The same results are obtained when the compounds of the formula I are formulated according to the other examples of WO 97/34485.

Example B2

Post-emergence Herbicidal Action

Monocotyledonous and dicotyledonous test plants are grown in standard soil in pots. At the 2- to 3-leaf stage of the test plants, the test substances are sprayed at optimum dosage (500 l of water/ha) as an aqueous suspension (prepared from a wettable powder (example F3, b) according to WO 97/34485) or emulsion (prepared from an emulsion concentrate (example F1, c) according to WO 97134485). The test plants are then grown further under optimum conditions in a greenhouse.

After a test period of 2 to 3 weeks, the test is evaluated using a 9-level scale of rating (1=complete damage, 9=no effect). Ratings of 1 to 4 (in particular 1 to 3) mean good to very good herbicidal action.

TABLE B2

| | | Post-emergence action: | | | | | | | |
|---|---|---|---|---|---|---|---|---|---|
| Compound | g/ha | Panicum | Digitaria | Echino. | Abutilon | Xanth. | Ipopur. | Amaranth | Chenop. |
| A10-B1 | 250 | 2 | 2 | 2 | 2 | 2 | 2 | 2 | 1 |
| A10-B52, (H3) | 250 | 1 | 1 | 2 | 1 | 2 | 2 | 2 | 1 |

TABLE B2-continued

| Compound | g/ha | Panicum | Digitaria | Echino. | Abutilon | Xanth. | Ipopur. | Amaranth | Chenop. |
|---|---|---|---|---|---|---|---|---|---|
| A830-B52 | 250 | 4 | 9 | 3 | 5 | 4 | 5 | 4 | 4 |
| A829-B52 | 250 | 2 | 6 | 4 | 3 | 6 | 4 | 2 | 2 |
| A829-B1 | 250 | 7 | 9 | 7 | 7 | 4 | 6 | 2 | 2 |
| A1-C2 | 250 | 7 | 8 | 4 | 3 | 4 | 3 | 2 | 4 |
| A833-B52 (K+) | 250 | 3 | 3 | 4 | 3 | 2 | 3 | 3 | 3 |
| A833-B52, (H4) | 250 | 3 | 3 | 4 | 3 | 1 | 2 | 2 | 3 |
| A10-B3 | 250 | 1 | 1 | 3 | 1 | 1 | 2 | 1 | 1 |
| A10-B14 | 250 | 2 | 2 | 3 | 2 | 2 | 2 | 2 | 1 |
| A10-B39 | 250 | 1 | 3 | 3 | 1 | 2 | 2 | 1 | 1 |
| A736-B52 | 250 | 1 | 1 | 2 | 1 | 2 | 2 | 1 | 1 |
| A10-C2 (H6) | 250 | 2 | 4 | 3 | 2 | 1 | 3 | 1 | 1 |
| A57-B52 (H5) | 250 | 1 | 1 | 2 | 1 | 2 | 2 | 1 | 1 |
| A18-B52 | 250 | 1 | 1 | 2 | 1 | 2 | 2 | 1 | 1 |
| A8-B52 | 250 | 1 | 1 | 1 | 1 | 2 | 1 | 1 | 1 |
| A19-B52 | 250 | 1 | 1 | 2 | 1 | 2 | 1 | 1 | 1 |
| A1-C5 | 250 | 4 | 2 | 2 | 2 | 4 | 2 | 2 | 1 |
| A2-C5 | 250 | 1 | 2 | 2 | 2 | 2 | 2 | 1 | 1 |
| A10-C5 | 250 | 2 | 2 | 2 | 2 | 2 | 2 | 1 | 1 |
| A11-C5 | 250 | 1 | 2 | 2 | 2 | 2 | 2 | 2 | 1 |
| A11-B52 | 250 | 1 | 1 | 2 | 2 | 2 | 2 | 1 | 1 |
| A834-B52 | 250 | 1 | 1 | 2 | 2 | 2 | 2 | 1 | 1 |
| A835-B52 | 250 | 1 | 1 | 2 | 2 | 3 | 2 | 2 | 1 |
| A854-B52 | 250 | 1 | 2 | 2 | 2 | 2 | 2 | 1 | 1 |
| A90-B52 | 250 | 2 | 2 | 3 | 2 | 3 | 4 | 3 | 1 |
| A33-B52 | 250 | 2 | 2 | 2 | 2 | 3 | 2 | 2 | 1 |
| A556-B52 | 250 | 1 | 2 | 2 | 1 | 2 | 2 | 2 | 1 |
| A646-B52 | 250 | 1 | 2 | 2 | 2 | 2 | 2 | 2 | 1 |
| A855-B52 | 250 | 2 | 2 | 2 | 2 | 2 | 2 | 2 | 1 |
| A817-B52 | 250 | 1 | 2 | 2 | 2 | 2 | 2 | 2 | 1 |
| A819-B52 | 250 | 2 | 3 | 2 | 2 | 2 | 2 | 2 | 1 |
| A856-B52 | 250 | 2 | 2 | 2 | 2 | 2 | 1 | 2 | 1 |
| A857-B52 | 250 | 2 | 2 | 2 | 2 | 2 | 2 | 2 | 1 |
| A63-B52 | 250 | 1 | 2 | 2 | 2 | 2 | 2 | 2 | 2 |
| A20-B52 | 250 | 1 | 2 | 2 | 2 | 2 | 2 | 2 | 1 |
| A858-B52 | 250 | 2 | 2 | 2 | 2 | 2 | 2 | 1 | 2 |
| A836-B52 | 250 | 2 | 2 | 2 | 2 | 3 | 3 | 2 | 1 |
| A859-B52 | 250 | 1 | 2 | 2 | 2 | 2 | 2 | 2 | 1 |
| A818-B52 | 250 | 2 | 2 | 3 | 2 | 2 | 2 | 2 | 1 |
| A837-B52 | 250 | 1 | 2 | 2 | 2 | 2 | 2 | 1 | 1 |
| A28-B52 | 250 | 1 | 2 | 2 | 2 | 3 | 4 | 1 | 1 |
| A28-B52 (Et3NH+) | 250 | 1 | 2 | 2 | 2 | 3 | 2 | 2 | 1 |
| A838-B52 | 250 | 2 | 2 | 3 | 1 | 2 | 2 | 2 | 1 |
| A839-B52 | 250 | 2 | 2 | 2 | 2 | 2 | 2 | 2 | 1 |
| A860-B52 | 250 | 2 | 1 | 2 | 2 | 2 | 2 | 2 | 1 |
| A861-B52 | 250 | 2 | 3 | 5 | 3 | 2 | 2 | 2 | 1 |
| A840-B52 | 250 | 2 | 3 | 4 | 3 | 3 | 3 | 2 | 1 |
| A841-B52 | 250 | 2 | 4 | 4 | 3 | 3 | 3 | 1 | 1 |
| A842-B52 | 250 | 3 | 3 | 5 | 3 | 3 | 3 | 2 | 1 |
| A843-B52 | 250 | 2 | 3 | 3 | 3 | 3 | 6 | 3 | 1 |
| A844-B52 | 250 | 2 | 3 | 4 | 3 | 3 | 3 | 3 | 1 |
| A856-B112 | 250 | 3 | 3 | 5 | 2 | 3 | 3 | 3 | 1 |
| A20-C5 | 250 | 2 | 3 | 4 | 3 | 3 | 3 | 2 | 1 |
| A10-C28 | 250 | 4 | 4 | 4 | 3 | 3 | 3 | 2 | 1 |
| A11-C28 | 250 | 3 | 4 | 4 | 3 | 3 | 3 | 2 | 1 |
| A10-B52 (Et3NH+) | 250 | 2 | 2 | 2 | 2 | 2 | 2 | 2 | 1 |
| A862-B52 | 250 | 2 | 2 | 3 | 3 | 2 | 5 | 2 | 1 |
| A24-B52 | 250 | 2 | 2 | 2 | 2 | 2 | 2 | 2 | 1 |
| A845-B52 | 250 | 2 | 2 | 2 | 2 | 2 | 2 | 2 | 1 |
| A837-B52 (Et3NH+) | 250 | 2 | 2 | 2 | 2 | 2 | 2 | 2 | 1 |
| A67-B52 | 250 | 2 | 2 | 2 | 2 | 2 | 3 | 2 | 1 |
| A863-B52 | 250 | 2 | 2 | 3 | 2 | 2 | 3 | 2 | 1 |
| A10-B17 | 250 | 2 | 1 | 2 | 2 | 2 | 2 | 2 | 1 |
| A846-B52 | 250 | 1 | 2 | 2 | 2 | 2 | 1 | 2 | 2 |
| A847-B52 | 250 | 1 | 2 | 1 | 2 | 2 | 4 | 3 | 1 |
| A848-B52 | 250 | 2 | 2 | 2 | 2 | 2 | 2 | 1 | 1 |
| A56-B52 | 250 | 1 | 2 | 2 | 2 | 2 | 2 | 1 | 1 |
| A26-B52 | 250 | 2 | 2 | 2 | 2 | 2 | 2 | 2 | 1 |
| A849-B52 | 250 | 2 | 2 | 3 | 2 | 2 | 2 | 2 | 2 |
| A10-B4 | 250 | 1 | 1 | 2 | 1 | 2 | 1 | 2 | 1 |
| A850-B52 | 250 | 2 | 2 | 2 | 2 | 2 | 2 | 2 | 1 |
| A10-C29 | 250 | 2 | 3 | 3 | 2 | 2 | 1 | 2 | 1 |
| A10-B111 | 250 | 2 | 2 | 3 | 3 | 3 | 3 | 2 | 1 |
| A3-C5 | 250 | 3 | 4 | 3 | 3 | 3 | 3 | 3 | 1 |
| A851-B52 | 250 | 3 | 3 | 4 | 3 | 3 | 3 | 2 | 1 |
| A852-B52 | 250 | 3 | 4 | 4 | 3 | 3 | 3 | 3 | 1 |

TABLE B2-continued

| Compound | g/ha | Panicum | Digitaria | Echino. | Abutilon | Xanth. | Ipopur. | Amaranth | Chenop. |
|---|---|---|---|---|---|---|---|---|---|
| | | | | Post-emergence action: | | | | | |
| A10-B25 | 250 | 3 | 4 | 4 | 3 | 3 | 3 | 2 | 1 |
| A27-B52 | 250 | 1 | 2 | 2 | 3 | 2 | 4 | 2 | 5 |
| A864-C5 | 250 | 1 | 2 | 2 | 2 | 2 | 2 | 1 | 1 |
| A864-B52 | 250 | 2 | 2 | 2 | 2 | 2 | 2 | 2 | 1 |

The same results are obtained when the compounds of the formula I are formulated according to the other examples of WO 97/34485.

What is claimed is:
1. A compound of the formula I

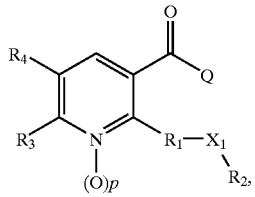

(I)

in which
p is 0 or 1;
$R_1$ is a $C_1$–$C_6$alkyene, $C_3$–$C_6$alkenylene or $C_3$–$C_6$alkynylene chain which may be mono- or polysubstituted by halogen or $R_5$, where the unsaturated bonds of the chain are not attached directly to the substituent $X_1$;
$X_1$ is oxygen, thio, sulfinyl, sulfonyl;
$R_2$ is a $C_1$–$C_6$alkyl, $C_3$–$C_6$alkenyl or $C_3$–$C_6$alkynyl group which is mono- or polysubstituted by halogen, hydroxyl, amino, formyl, nitro, cyano, mercapto, carbamoyl, $C_1$–$C_6$alkoxy, $C_1$–$C_6$alkoxycarbonyl, $C_2$–$C_6$alkenyl, $C_2$–$C_6$haloalkeny, $C_2$–$C_6$alkynyl, $C_2$–$C_6$haloalkynyl, $C_3$–$C_6$cycloalkyl, by halogen-substituted $C_3$–$C_6$cycloalkyl, or by $C_3$–$C_6$alkenyloxy, $C_3$–$C_6$alkynyloxy, $C_1$–$C_6$haloalkoxy, $C_3$–$C_6$haloalkenyloxy, cyano-$C_1$–$C_6$alkoxy, $C_1$–$C_6$alkoxy-$C_1$–$C_6$alkoxy, $C_1$–$C_6$alkoxy-$C_1$–$C_6$alkoxy-$C_1$–$C_6$alkoxy, $C_1$–$C_6$alkylthio-$C_1$–$C_6$alkoxy, $C_1$–$C_6$alkylsulfinyl-$C_1$–$C_6$alkoxy, $C_1$–$C_6$alkylsulfonyl-$C_1$–$C_6$alkoxy, $C_1$–$C_6$alkoxycarbonyl-$C_1$–$C_6$alkoxy, $C_1$–$C_6$alkoxycarbonyl, $C_1$–$C_6$alkylcarbonyl, $C_1$–$C_6$alkylthio, $C_1$–$C_6$alkylsulfinyl, $C_1$–$C_6$alkylsulfonyl, $C_1$–$C_6$haloalkylthio, $C_1$–$C_6$haloalkylsulfinyl, $C_1$–$C_6$haloalkylsulfonyl, oxiranyl, which for its part may be substituted by $C_1$–$C_6$alkyl, or by (3-oxetanyl)oxy, which for its part may be substitued by $C_1$–$C_6$alkyl, or by benzylthio, benzylsulfinyl, benzylsulfonyl, $C_1$–$C_6$alkylamino, di($C_1$–$C_6$alkyl)amino, $R_9S(O)_2O$, $R_{10}N(R_{11})SO_2$—, thiocyanato, phenyl, phenoxy, phenylthio, phenylsulfinyl or phenylsulfonyl;
where the phenyl- or benzyl-containing groups for their part may be substituted by one or more $C_1$–$C_6$alkyl, $C_1$–$C_6$haloalkyl, $C_1$–$C_6$alkoxy, $C_1$–$C_6$haloalkoxy, halogen, cyano, hydroxyl or nitro groups, $R_3$ is $C_1$–$C_3$haloalkyl;
$R_4$ is hydrogen, halogen, $C_1$–$C_3$alkyl, $C_1$–$C_3$haloalkyl, $C_1$–$C_3$alkoxy, $C_1$–$C_3$alkoxy-$C_1$–$C_3$alkyl or $C_1$–$C_3$alkoxy-$C_1$–$C_3$alkoxy;
$R_5$ is hydroxyl, $C_1$–$C_6$alkoxy, $C_3$–$C_6$cycloalkyloxy, $C_1$–$C_6$alkoxy-$C_1$–$C_6$alkoxy, $C_1$–$C_6$alkoxy-$C_1$–$C_6$alkoxy or $C_1$–$C_2$alkylsulfonyloxy;
$R_9$, $R_{10}$, and $R_{11}$ independently of one another are hydrogen, $C_1$–$C_6$alkyl, $C_1$–$C_6$haloalkyl, $C_1$–$C_6$alkoxycarbonyl, $C_1$–$C_6$alkylcarbonyl, $C_1$–$C_6$alkoxy-$C_1$–$C_6$alkyl, $C_1$–$C_6$alkoxy-$C_1$–$C_6$alkyl substituted by $C_1$–$C_6$alkoxy, benzyl or phenyl, where phenyl and benzyl for their part may be mono- or polysubstituted by $C_1$–$C_4$alkyl, $C_1$–$C_6$haloalkyl, $C_1$–$C_6$alkoxy, $C_1$–$C_6$haloalkoxy, halogen, cyano, hydroxyl or nitro;
Q is $Q_1$

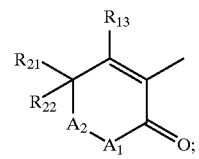

($Q_1$)

in which
$A_1$ is $C(R_{14}R_{15})$, $NR_{16}$ or oxygen;
$A_2$ is $C(R_{17}R_{18})$, $C(O)$, —C=N—O—$R_{19}$, oxygen, thio, sulfinyl, sulfonyl, —$NR_{20}$ or ethylene; with the provisos that $A_1$ is different from oxygen if $A_2$ is oxygen, $C(O)$, thio, sulfinyl, —C=N—O—$R_{19}$, $NR_{20}$ or $C(R_{17}R_{18})$, where $R_{17}$ and $R_{18}$ independently of one another are $C_1$–$C_4$alkoxy, $C_1$–$C_4$alkylthio, $C_1$–$C_4$alkylsulfinyl, $C_1$–$C_4$alkylsulfonyl; and $A_1$ is different from $NR_{16}$ if $A_2$ is thio, sulfinyl or $C(R_{17}R_{18})$, where $R_{17}$ and $R_{18}$ independently of one another are $C_{1-4}$alkoxy, $C_1$–$C_4$alkylthio, $C_1$–$C_4$alkylsulfinyl, $C_1$–$C_4$alkylsulfonyl; $R_{14}$ and $R_{22}$ independently of one another are hydrogen, $C_1$–$C_4$alkyl, $C_1$–$C_4$haloalkyl, $C_3$–$C_4$alkenyl, $C_3$–$C_4$alkynyl, $C_1$–$C_4$alkylthio, $C_1$–$C_4$alkylsulfinyl, $C_1$–$C_4$alkylsulfonyl, $C_1$–$C_4$alkylsulfonyloxy, $C_1$–$C_4$alkoxy, $C_1$–$C_4$alkoxycarbonyl or $C_1$–$C_4$alkylcarbonyl;
$R_{15}$ and $R_{21}$ independently of one another are hydrogen, $C_1$–$C_4$alkyl, $C_1$–$C_4$haloalkyl, $C_3$–$C_4$alkenyl or $C_3$–$C_4$alkynyl;
$R_{17}$ is hydrogen, $C_1$–$C_4$alkyl, $C_1$–$C_4$haloalkyl, $C_1$–$C_4$alkoxy, $C_1$–$C_4$alkylthio, $C_1$–$C_4$alkylsulfinyl or $C_1$–$C_4$alkylsulfonyl;
$R_{18}$ is hydrogen, $C_1$–$C_4$alkyl, $C_1$–$C_4$haloalkyl, $C_3$–$C_4$alkenyl, $C_3$–$C_4$alkynyl, $C_1$–$C_4$alkoxy, $C_1$–$C_4$alkylthio, $C_1$–$C_4$alkylsulfinyl, $C_1$–$C_4$alkylsufonyl or $C_1$–$C_4$dialkoxyalkyl-$C_1$–$C_4$alkyl;
$R_{20}$ is $C_1$–$C_4$alkyl, $C_3$–$C_6$cycoalkyl, $C_3$–$C_4$alkenyl, $C_3$–$C_4$alkynyl, $C_1$–$C_4$alkylcarbonyl, $C_1$–$C_4$alkylcarbonyloxy, di($C_1$–$C_4$alkyl)

aminocarbonyl or benzyl, where the phenyl group may be mono- or polysubstituted by $C_1-C_6$alkyl, $C_1-C_6$haloalkyl, $C_1-C_6$alkoxy, $C_1-C_6$haloalkoxy, halogen, cyano, hydroxyl or nitro;

$R_{19}$ and $R_{16}$ independently of one another are hydrogen, $C_1-C_4$alkyl, $C_3-C_6$cycloalkyl, $C_3-C_4$alkenyl, $C_3-C_4$alkynyl, benzyl or phenyl, where phenyl and benzyl for their part may be mono- or polysubstituted by $C_1-C_6$alkyl, $C_1-C_6$haloalkyl, $C_1-C_6$alkoxy, $C_1-C_6$haloalkoxy, halogen, cyano, hydroxyl or nitro;

or $R_{14}$ and $R_{22}$ together form a $C_2-C_3$alkylene chain;

or $R_{14}$ and $R_{15}$ together and/or $R_{17}$ and $R_{18}$ together and/or $R_{21}$ and $R_{22}$ together form a $C_2-C_4$alkylene chain which may be interrupted by oxygen and/or carbonyl and/or sulfur, with the proviso that the oxygen and sulfur atoms are separated by at least one methylene group;

or $R_{14}$ and $R_{18}$ together form a $C_2-C_4$alkylene chain; or $R_{22}$ and $R_{18}$ together form a $C_1-C_4$alkylene chain;

or $R_{18}$ together with $R_{22}$ or $R_{14}$ forms a direct bond;

or $R_{16}$ and $R_{18}$ together form a $C_2-C_4$alkylene chain;

$R_{13}$ is hydroxyl, $O^-M^+$, where $M^+$ is an alkali metal cation or ammonium cation, halogen, $C_1-C_{12}$alkylsulfonyloxy, amino, $C_1-C_4$alkylthio, $C_1-C_{12}$alkylsulfinyl, $C_1-C_{12}$alkylsulfonyl, $C_1-C_{12}$haloalkylthio, $C_1-C_{12}$haloalkylsulfinyl, $C_1-C_{12}$haloalkylsufonyl, $C_1-C_6$alkoxy-$C_1-C_6$alkylthio, $C_1-C_6$alkoxy-$C_1-C_6$alkylsulfinyl, $C_1-C_6$alkoxy-$C_1-C_6$alkylsulfonyl, $C_3-C_{12}$alkenylthio, $C_3-C_{12}$alkenylsulfinyl, $C_3-C_{12}$alkenylsulfonyl, $C_3-C_{12}$alkynylthio, $C_3-C_{12}$alkynylsulfinyl, $C_3-C_{12}$alkynylsulfonyl, $C_1-C_4$alkoxycarbonyl-$C_1-C_4$alkylthio, $C_1-C_4$alkoxycarbonyl-$C_1-C_4$alkylsulfinyl, $C_1-C_4$alkoxycarbonyl-$C_1-C_4$alkylsulfonyl, $(C_1-C_4$alkoxy$)_2$P(O)O, $C_1-C_4$alkyl-$(C_1-C_4$alkoxy)P(O)O, H$(C_1-C_4$alkoxy)P(O)O, $R_{23}R_{24}NR_{25}R_{26}N$, NH, $R_{27}R_{28}NC(O)O-$, $R_{29}R_{30}NC(O)NH-$, $C_1-C_{18}$alkylcarbonyloxy, $C_2-C_{18}$alkenylcarbonyloxy, $C_2-C_{18}$alkynylcarbonyloxy, $C_3-C_6$cycloalkylcarbonyloxy, $C_1-C_{12}$alkoxycarbonyloxy, $C_1-C_{12}$alkythiocarbonyloxy, $C_1-C_{12}$alkylthiocarbamoyl, where the alkyl, alkenyl and alkynyl groups may be substituted by halogen, $C_1-C_6$alkoxy, $C_1-C_6$alkylthio, $C_1-C_6$alkylsulfinyl, $C_1-C_6$alkylsulfonyl or cyano;

or $R_{13}$ is phenoxy, phenylthio, phenylsulfinyl, phenylsulfonyl, phenylsulfonylamino, phenylsulfonyloxy or benzoyloxy, where the phenyl groups for their part may be substituted by one or more halogen, nitro, cyano, $C_1-C_4$alkyl, $C_1-C_4$haloalkyl, $C_1-C_4$alkoxy or $C_1-C_4$haloalkoxy groups;

or $R_{13}$ is a group $Het_1$-thio, $Het_2$-sulfinyl, $Het_3$-sulfonyl, $Het_4$-(CO)O or $Het_5$-N$(R_{33})$; in which $Het_1$, $Het_2$, $Het_3$, $Het_4$ and $Het_5$ independently of one another are a five- to ten-membered monocyclic or fused bicyclic ring system which may be aromatic or partially saturated and may contain 1 to 4 heteroatoms selected from the group consisting of nitrogen, oxygen and sulfur, and where each ring system may not contain more than 2 oxygen atoms and not more than 2 sulfur atoms, and where the ring system itself can be substituted by $C_1-C_6$akyl, $C_1C_6$haloalkyl, $C_1-C_6$alkoxy, $C_1-C_6$haloalkoxy, $C_1-C_6$alkylthio, $C_1-C_6$alkylsulfinyl, $C_1-C_6$alkylsulfonyl, di$(C_1-C_4$alkyl)aminosulfonyl, di$(C_1-C_4$alkyl)amino, halogen, cyano, nitro or phenyl, and where the substituents on the nitrogen in the heterocyclic ring are different from halogen;

$R_{23}$, $R_{24}$, $R_{25}$, $R_{26}$, $R_{27}$, $R_{28}$, $R_{29}$, $R_{30}$ and $R_{33}$ independently of one another are hydrogen or $C_1-C_6$alkyl;

or $R_{23}$ and $R_{24}$ together or $R_{25}$ and $R_{26}$ together or $R_{27}$ and $R_{28}$ together or $R_{29}$ and $R_{30}$ together are pyrolidino, piperidino, morpholino, thiomorpholino, which may be mono- or polysubstitted by methyl groups.

2. A process for preparing compounds of the formula I as claimed in claim 1, which comprises, to prepare compounds of the formula I, in which $R_1$, $R_2$, $R_3$, $R_4$ and $X_1$ are as defined under formula I and Q is a group $Q_1$, either a) reacting a compound of the formula Ia

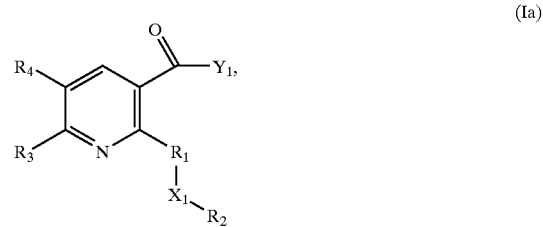

(Ia)

in which $R_1$, $R_2$, $R_3$, $R_4$ and $X_1$ are as defined under formula I and $Y_1$ is a leaving group, in an inert organic solvent in the presence of a base with a compound of the formula II

(II)

in which $R_{22}$, $R_{21}$, $A_2$ and $A_1$ are as defined under formula I, to give the compounds of the formulae IIIa and IIIb

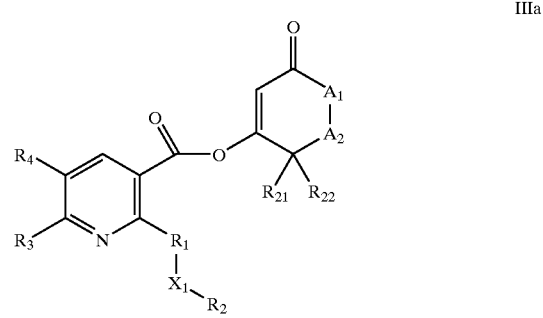

IIIa

IIIb

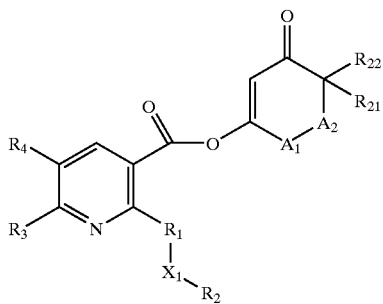

and then isomerizing these in the presence of a base and a catalytic amount of dimethylamimopyddine (DMAP) or a source of cyanide, for example acetone cyanohydrin; or b) reacting a compound of the formnula Ib

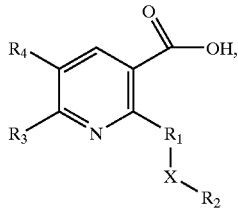
(Ib)

in which $R_1$, $R_2$, $R_3$, $R_4$ and $X_1$ are as defined under formula I, with a compound of the formula II

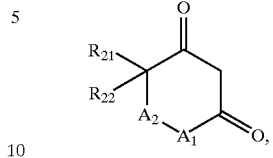
(II)

in which $R_{22}$, $R_{21}$, $A_1$ and $A_2$ are as defined under formula I, in an inert organic solvent in the presence of a base and a coupling agent to give the compound of the formula IIIa or IIIb, and then isomerizing these as described under route a).

3. A herbicidal and plant-growth-inhibiting composition, which contains a herbicdally effective amount of a compound of the formula I as claimed in claim 1 on an inert carrier.

4. A method for controlling undesirable plant growth wherein a herbicidally effective amount of an active compound of the formula I as claimed in claim 1 or a composition which contains this active compound is applied to the plants or their habitat.

5. A method for inhibitng plant growth, wherein a herbicidally effective amount of an active conmpound of the formula I as claimed in claim 1 or a composition which contains this active compound is applied to the plants or their habitat.

* * * * *